United States Patent
Wilson

(10) Patent No.: US 10,221,213 B2
(45) Date of Patent: Mar. 5, 2019

(54) PHARMACEUTICALLY RELEVANT AROMATIC-CATIONIC PEPTIDES

(71) Applicant: Stealth BioTherapeutics Corp., Monaco (MC)

(72) Inventor: D. Travis Wilson, Newton, MA (US)

(73) Assignee: STEALTH BIOTHERAPEUTICS CORP, Monaco (MC)

( * ) Notice: Subject to any disclaimer, the term of this patent is extended or adjusted under 35 U.S.C. 154(b) by 115 days.

(21) Appl. No.: 15/108,004

(22) PCT Filed: Dec. 23, 2014

(86) PCT No.: PCT/US2014/072264
§ 371 (c)(1),
(2) Date: Jun. 24, 2016

(87) PCT Pub. No.: WO2015/100376
PCT Pub. Date: Jul. 2, 2015

(65) Prior Publication Data
US 2016/0340389 A1 Nov. 24, 2016

Related U.S. Application Data

(60) Provisional application No. 61/947,261, filed on Mar. 3, 2014, provisional application No. 61/921,376, filed on Dec. 27, 2013.

(51) Int. Cl.
*C07K 1/02* (2006.01)
*C07K 5/11* (2006.01)

(52) U.S. Cl.
CPC ............. *C07K 5/1019* (2013.01); *C07K 1/02* (2013.01)

(58) Field of Classification Search
None
See application file for complete search history.

(56) References Cited

U.S. PATENT DOCUMENTS

| 6,248,716 B1 * | 6/2001 | Deigin | C07K 5/1016 514/17.5 |
| 2003/0069231 A1 * | 4/2003 | Rudolf | A61K 31/4745 514/223.2 |
| 2007/0225261 A1 | 9/2007 | Miller | |
| 2007/0275903 A1 | 11/2007 | Bebbington et al. | |
| 2009/0215986 A1 | 8/2009 | Epstein et al. | |
| 2013/0059784 A1 | 3/2013 | Wilson | |
| 2013/0303436 A1 | 11/2013 | Wilson | |

FOREIGN PATENT DOCUMENTS

| JP | 2001-503011 A | 3/2001 |
| WO | WO-96/02267 | 1/1996 |
| WO | WO-2012/174117 A2 | 12/2012 |
| WO | WO-2013/126597 | 8/2013 |
| WO | WO-2015/134096 | 9/2015 |

OTHER PUBLICATIONS

Harrison et al., 2,6-Dimethyltyrosine Analogues of a Stereodiversified Ligand Library: Highly Potent, Selective, Non-Peptidic u Opioid Receptor Agonists, J. Med. Chem., 2003, pp. 677-680.*
Soloshonok et al., "Large-scale asymmetric synthesis of novel sterically constrained 2',6'-dimethyl- and a,2',6'-trimethyltyrosine and -phenylalanine derivatives via alkylation of chiral equivalents of nucleophilic glycine and alanine", Tetrahedron, 2001, pp. 6375-6382 (Year: 2001).*
Gowda, "Removal of some commonly used protecting groups in peptide syntheses by catalytic transfer hydrogenation with formic acid and 10% palladium on carbon", Indian Journal of Chemistry, 2002, pp. 1064-1067 (Year: 2002).*
Extended European Search Report issued on EP Application 14874049.1, dated Aug. 25, 2017.
International Search Report and Written Opinion of the International Searching Authority dated Mar. 25, 2015, 10 pages.
Still, W. Clark et al., "Rapid Chromatographic Technique for Preparative Separations with Moderate Resolution," J. Org. Chem., (1978), vol. 43, No. 14, pp. 2923-2925.
Tsuda et al., "Amino acid coupling chemistry, solution-phase peptide synthesis," Peptide and Proteins in Organic Chemistry, pp. 203-252 (Jan. 31, 2011).

* cited by examiner

*Primary Examiner* — Lianko G Garyu
(74) *Attorney, Agent, or Firm* — Foley & Lardner LLP; James P. McParland; Joseph P. Meara

(57) ABSTRACT

The present technology provides peptides, methods of generating the peptides, and pharmaceutically acceptable salts of the peptides. In some embodiments, the peptide is D-Arg-2'6'-Dmt-Lys-Phe-NH$_2$.

17 Claims, No Drawings

PHARMACEUTICALLY RELEVANT AROMATIC-CATIONIC PEPTIDES

CROSS-REFERENCE TO RELATED APPLICATIONS

This application is a U.S. national phase application under 35 U.S.C § 371 of International Application No. PCT/US2014/072264, filed on Dec. 27, 2013, which claims priority to U.S. Provisional Application No. 61/921,376, filed Dec. 27, 2013, and U.S. Provisional Application No. 61/947,261, filed Mar. 3, 2014, each of which are incorporated herein by reference in their entireties for any and all purposes.

FIELD OF TECHNOLOGY

The present technology relates generally to peptides, pharmaceutically acceptable salts including the peptides, and methods of generating the peptides.

SUMMARY

In an aspect, a process is provided involving combining a compound of formula VIII

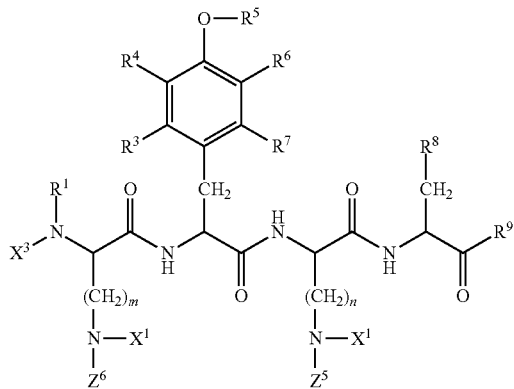

(VIII)

with a hydrogen source and a transition metal catalyst to form a compound of formula I

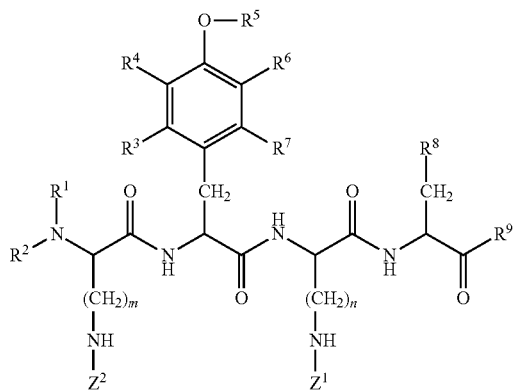

(I)

or a pharmaceutically acceptable salt thereof, wherein $R^1$ and $R^2$ are each independently
(i) hydrogen;
(ii) substituted or unsubstituted $C_1$-$C_6$ alkyl;
(iii) substituted or unsubstituted aralkyl;
(iv) substituted or unsubstituted cycloalkylalkyl;
(v) substituted or unsubstituted $C_2$-$C_6$ alkenyl;
(vi) an amino protecting group;
or $R^1$ and $R^2$ together form a 3, 4, 5, 6, 7, or 8 membered substituted or unsubstituted heterocyclyl ring;
$R^3$, $R^4$, $R^6$, and $R^7$ are each independently hydrogen, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted; $R^5$ is selected from hydrogen, $C_1$-$C_6$ alkyl, aralkyl, —C(O)-alkyl, —C(O)-aryl, or —C(O)-aralkyl, wherein each alkyl, aryl or aralkyl group is substituted or unsubstituted; $R^8$ is

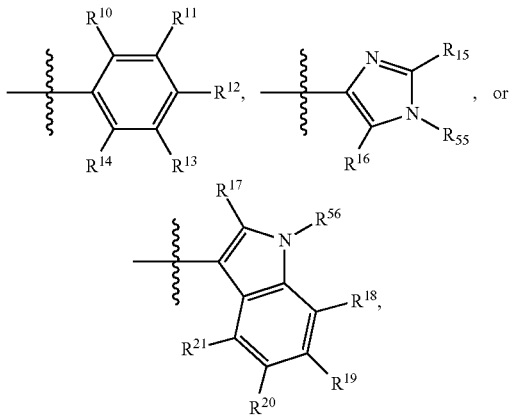

where $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted; $R^{55}$ and $R^{56}$ are each independently selected from H, or a $C_1$-$C_6$ alkyl, $C_1$-$C_6$ alkoxy, amino, $C_1$-$C_4$ alkylamino, $C_1$-$C_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted; $R^9$ is OR' or NR'R"; R' at each occurrence is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; R" is a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group; n is 1, 2, 3, 4, or 5; m is 1, 2, 3, 4, or 5; $X^1$ at each occurrence is independently hydrogen or an amino protecting group resistant to acid-mediated removal and susceptible to hydrogen-mediated removal; $X^2$ at each occurrence is independently hydrogen or an amino protecting group resistant to acid-mediated removal and susceptible to hydrogen-mediated removal; $X^3$ is $X^1$ or $R^2$; $Z^1$ and $Z^2$ are each independently hydrogen, —C(NH)—$NH_2$ or a substituted or unsubstituted alkyl, aryl, or aralkyl group; and $Z^5$ and $Z^6$ are each independently hydrogen, —C(N—$X^4$)—

NH—X² or a substituted or unsubstituted alkyl, aryl, or aralkyl group; wherein X⁴ at each occurrence is independently hydrogen or an amino protecting group resistant to acid-mediated removal and susceptible to hydrogen-mediated removal; wherein at least one of $X^1$, $X^2$, $X^3$ and $X^4$ is an amino protecting group resistant to acid-mediated removal and susceptible to hydrogen-mediated removal. In some embodiments $X^3$ and at least one of $X^1$, $X^2$ and $X^4$ are independently an amino protecting group resistant to acid-mediated removal and susceptible to hydrogen-mediated removal. In other embodiments, $X^3$ and at least two of $X^1$, $X^2$ and $X^4$ are independently an amino protecting group resistant to acid-mediated removal and susceptible to hydrogen-mediated removal.

In any of the above embodiments, the compound of formula VIII may be formed by a process involving combining a compound of formula VI

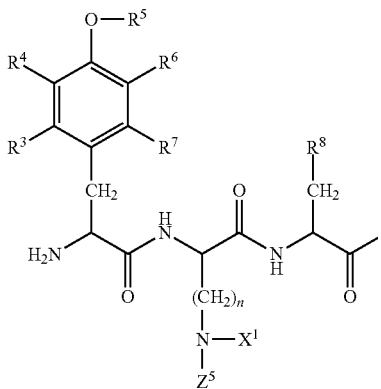

(VI)

with a compound of formula VII

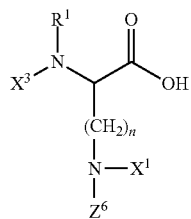

(VII)

under conditions to form the compound of formula VIII.

In any of the above embodiments, it may be that forming a compound of formula VI involves combining a compound of formula III

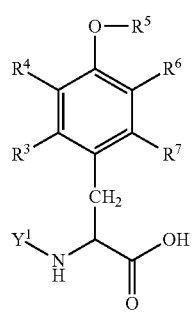

(III)

with a compound of formula IV

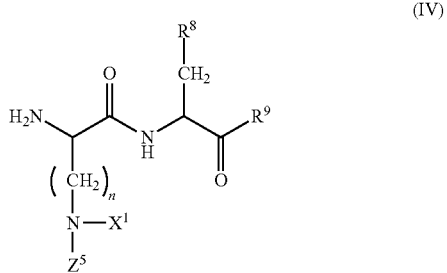

(IV)

under conditions to form a compound of formula V,

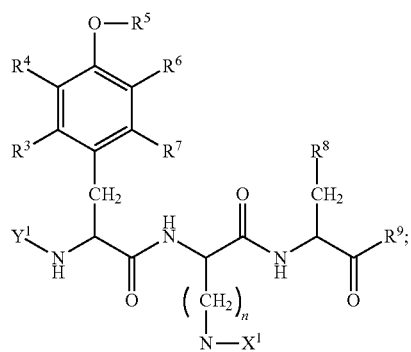

(V)

and combining the compound of formula V

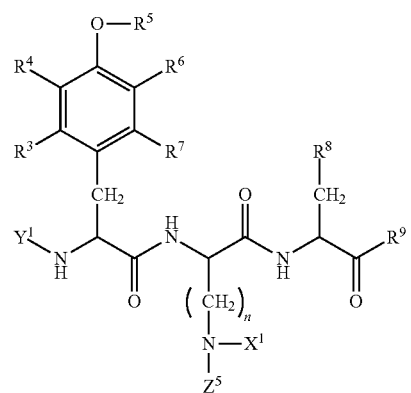

(V)

with a cleaving acid to produce a compound of formula VI

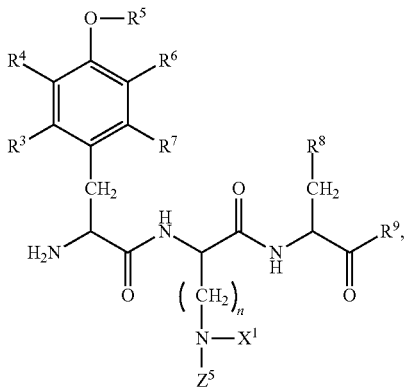

(VI)

where $Y^1$ is an amino protecting group susceptible to acid-mediated removal.

In any of the above embodiments, it may be that $Y^1$ is tert-butyloxycarbonyl (Boc); $X^1$ at each occurrence is independently hydrogen, allyloxycarbonyl, benzyloxycarbonyl (Cbz), or 2-chlorobenzyloxycarbonyl; $X^2$ at each occurrence is independently hydrogen, allyloxycarbonyl, benzyloxycarbonyl (Cbz), or 2-chlorobenzyloxycarbonyl; and $X^4$ at each occurrence is independently hydrogen, nitro, allyloxycarbonyl, benzyloxycarbonyl (Cbz), or 2-chlorobenzyloxycarbonyl.

In any of the above embodiments, it may be that $R^4$, $R^5$, and $R^6$ are each hydrogen; $R^3$ and $R^7$ are methyl; $R^8$ is

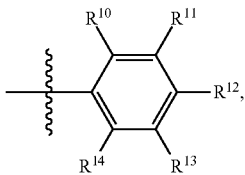

where $R^{10}$, $R_{11}$, $R^{12}$, $R^{13}$, and $R_{14}$ are all hydrogen; $Z^1$ and $Z^5$ are hydrogen; $Z^2$ is —C(NH)—NH$_2$; $Z^6$ is —C(N—$X^4$)—NH—$X^2$ wherein at least one of $X^2$ and $X^4$ is not H; n is 4; and m is 3.

In any of the above embodiments, it may be that $R^4$, $R^5$, and $R^6$ are each hydrogen; $R^3$ and $R^7$ are methyl; $R^8$ is

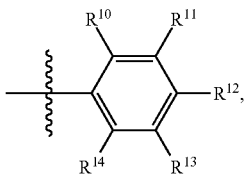

where $R^{10}$, $R^{11}$, $R^{12}$, $R^{13}$, and $R^{14}$ are all hydrogen; $X^2$ is not H; $X^4$ is not H; $Z^1$ and $Z^5$ are hydrogen; $Z^2$ is —C(NH)—NH$_2$; $Z^6$ is C(N—$X^4$)—NH—$X^2$; n is 4; and m is 3.

In any of the above embodiments, it may be that the hydrogen source includes hydrogen gas, diimide, cyclohexene, cyclohexadiene, formic acid, formate salts, or combinations of any two or more thereof; and the transition metal catalyst comprises Co, Ir, Mo, Ni, Pt, Pd, Rh, Ru, W, or combinations of any two or more thereof. In any of the above embodiments, it may be that the transition metal catalyst includes a support material. In any of the above embodiments, it may be that the support material comprises carbon, carbonate salts, silica, silicon, silicates, alumina, clay, or mixtures of any two or more thereof. In any of the above embodiments, it may be that the transition metal catalyst is Pd on carbon or Pd on silicon. In any of the above embodiments, it may be that a solvent is further included with the transition metal catalyst and the hydrogen source. Such solvents include, but are not limited to, alcohols (e.g., methanol (CH$_3$OH), ethanol (EtOH), isopropanol (iPrOH), trifluorethanol (TFE), butanol (BuOH)), halogenated sovlents (e.g., methylene chloride (CH$_2$Cl$_2$), chloroform (CHCl$_3$), benzotrifluoride (BTF; PhCF$_3$)), ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), amides (e.g., dimethylformamide (DMF), dimethylacetamide (DMA)), nitriles (e.g., acetonitrile (CH$_3$CN), proprionitrile (CH$_3$CH$_2$CN), benzonitrile (PhCN)), sulfoxides (e.g., dimethyl sulfoxide), sulfones (e.g., sulfolane), water, or mixtures of any two or more thereof. In such embodiments, it may be that the solvent includes methanol (CH$_3$OH), ethanol (EtOH), isopropanol (iPrOH), trifluorethanol (TFE), butanol (BuOH), methylene chloride (CH$_2$Cl$_2$), chloroform (CHCl$_3$), benzotrifluoride (BTF; PhCF$_3$), tetrahydrofuran (THF), 2-methyltetrahydrofuran (2Me-THF), dimethoxyethane (DME), dioxane, ethyl acetate, isopropyl acetate, acetone, methylethyl ketone, methyl isobutyl ketone, dimethylformamide (DMF), dimethylacetamide (DMA), acetonitrile (CH$_3$CN), proprionitrile (CH$_3$CH$_2$CN), benzonitrile (PhCN), dimethyl sulfoxide, sulfolane, water, or mixtures of any two or more thereof. In any of the above embodiments, it may be that the solvent further includes an acid. The acid may be present in a suitable amount, including a catalytic amount. Such acids include, but are not limited to, mineral acid (e.g., HCl, HBr, HF, H$_2$SO$_4$, H$_3$PO$_4$, HClO$_4$), a carboxylic acid (e.g., formic acid, acetic acid, propanoic acid, butanoic acid, pentanoic acid, lauric acid, stearic acid, deoxycholic acid, glutamic acid, glucuronic acid), boronic acid, a sulfinic acid, a sulfamic acid, or mixtures of any two or more thereof. In any of the above embodiments, it may be that the solvent further includes HCl, HBr, HF, H$_2$SO$_4$, H$_3$PO$_4$, HClO$_4$, formic acid, acetic acid, propanoic acid, butanoic acid, pentanoic acid, lauric acid, stearic acid, deoxycholic acid, glutamic acid, glucuronic acid, boronic acid, a sulfinic acid, a sulfamic acid, or mixtures of any two or more thereof. In any of the above embodiments, it may be that the combination of the compound of formula VIII, the hydrogen source, and the transition metal catalyst is subjected to a temperature from about −20° C. to about 150° C.

In any of the above embodiments, it may be that the conditions to form the compound of formula VIII include a coupling agent. Such coupling agents as used in any of the aspects and embodiments described herein may include water soluble carbodiimides such as 1-ethyl-3-(3-dimethylaminopropyl)carbodiimide (EDC) or the hydrochloride salt of EDC (EDC-HCl). The coupling agent may be (7-azabenzotriazol-1-yloxy)tripyrrolidinophosphonium hexafluorophosphate (PyAOP), O-benzotriazol-1-yl-N,N,N',N'-bis(pentamethylene)uronium hexafluorophosphate, O-(benzotriazol-1-yl)-N,N,N',N'-bis(tetramethylene)uronium hexafluorophosphate, (benzotriazol-1-yloxy)dipiperidinocarbenium hexafluorophosphate, (benzotriazol-1-yloxy)tripyrrolidinophosphonium hexafluorophosphate (PyBOP), (benzotriazol-1-yloxy)tris(dimethylamino)phosphonium hexafluorophosphate (BOP), O-(benzotriazol-1-yl)-N,N,N',N'-tetramethyluronium tetrafluoroborate (TBTU), bromotripyrrolidinophosphonium hexafluorophosphate, Bromotris(dimethylamino)phosphonium hexafluorophosphate, O-(6-chlorobenzotriazol-1-yl)-N,N,N',N'-tetramethyluronium tetrafluoroborate (TCTU), O-(6-chlorobenzotriazol-1-yl)-N,N,N',N'-tetramethyluronium hexafluorophosphate (HCTU), 2-chloro-1,3-dimethylimidazolidinium hexafluorophosphate, 2-chloro-1,3-dimethylimidazolidinium tetrafluoroborate, 2-chloro-1,3-dimethylimidazolidinium chloride, chlorodipyrrolidinocarbenium hexafluorophosphate, chloro-N,N,N',N'-tetramethylformamidinium hexafluorophosphate, chlorotripyrrolidinophosphonium hexafluorophosphate, (1-cyano-2-ethoxy-2-oxoethylidenaminooxy)dimethylamino-morpholino-carbenium hexafluorophosphate (COMU), dipyrrolidino(N-succinimidyloxy)carbenium hexafluorophosphate, O-[(ethoxycarbonyl)cyanomethylenamino]-N,N,N',N'-tetramethyluronium hexafluorophosphate, fluoro-N,N,N',N'-bis(tetramethylene) formamidinium hexafluorophosphate, fluoro-N,N,N',N'-bis(tetramethylene)formamidinium hexafluorophosphate, 1-hydroxybenzotriazole (HOBT), 1-hydroxy-7-azabenzotriazole (HOAT), 1-[bis(dimethylamino)methylene]-1H-1,2,3-triazolo[4,5-b]pyridinium 3-oxid hexafluorophosphate (HATU), N,N,N',N'-tetramethyl-O-(1H-benzotriazol-1-yl)uronium hexafluorophosphate (HBTU), 1-[(dimethylamino)(morpholino)methylene]-1H-[1,2,3]triazolo[4,5-b]pyridine-1-ium 3-oxide hexafluorophosphate (HDMA), O-(5-norbornene-2,3-dicarboximido)-N,N,N',N'-tetramethyluronium tetrafluoroborate, S-(1-oxido-2-pyridyl)-N,N,N',N'-tetramethylthiuronium hexafluorophosphate, 0-(2-oxo-1(2H)pyridyl)-N,N,N',N'-tetramethyluronium tetrafluoroborate, N,N,N',N'-tetramethyl-O—(N-succinimidyl)uronium hexafluorophosphate, N,N'-dicyclohexylcarbodiimide (DCC), N,N'-diisopropylcarbodiimide, 1-ethyl-3-(3-dimethylaminopropyl)carbodiimide (EDC), 1-[3-(dimethylamino)propyl]-3-ethylcarbodiimide methiodide (EDC-MeI), propane phosphonic acid anhydride (T3P), N,N'-di-tert-butylcarbodiimide, N-cyclohexyl-N'-(2-morpholinoethyl)carbodiimide methyl-p-toluenesulfonate, 2-ethoxy-1-ethoxycarbonyl-1,2-dihydroquinoline, 1,1'-carbonyldiimidazole, 1,1'-carbonyldi(1,2,4-triazole), bis(4-nitrophenyl) carbonate, 4-nitrophenyl chloroformate, di(N-succinimidyl) carbonate, 1-(2-mesitylenesulfonyl)-3-nitro-1H-1,2,4-triazole, or combinations of any two or more thereof. In any of the above embodiments, it may be that the conditions to form the compound of formula VIII further include a solvent. Such solvents include, but are not limited to, alcohols (e.g., methanol (CH$_3$OH), ethanol (EtOH), isopropanol (iPrOH), trifluorethanol (TFE), butanol (BuOH)), halogenated sovlents (e.g., methylene chloride (CH$_2$Cl$_2$), chloroform (CHCl$_3$), benzotrifluoride (BTF; PhCF$_3$)), ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), amides (e.g., dimethylformamide (DMF), dimethylacetamide (DMA)), nitriles (e.g., acetonitrile (CH$_3$CN), proprionitrile (CH$_3$CH$_2$CN), benzonitrile (PhCN)), sulfoxides (e.g., dimethyl sulfoxide), sulfones (e.g., sulfolane), water, or mixtures of any two or more thereof. In such embodiments, the solvent may include methanol (CH$_3$OH), ethanol (EtOH), isopropanol (iPrOH), trifluorethanol (TFE), butanol (BuOH), methylene chloride (CH$_2$Cl$_2$), chloroform (CHCl$_3$), benzotrifluoride (BTF; PhCF$_3$), tetrahydrofuran (THF), 2-methyltetrahydrofuran (2Me-THF), dimethoxyethane (DME), dioxane, ethyl acetate, isopropyl acetate, acetone, methylethyl ketone, methyl isobutyl ketone, dimethylformamide (DMF), dimethylacetamide (DMA), acetonitrile (CH$_3$CN), proprionitrile (CH$_3$CH$_2$CN), benzonitrile (PhCN), dimethyl sulfoxide, sulfolane, water, or a mixture of any two or more thereof. In any of the above embodiments, it may be that the conditions to form the compound of formula VIII further include a base. In any of the above embodiments, it may be that the conditions to form the compound of formula VIII occur at a temperature from about −40° C. to about 150° C. In any of the above embodiments, it may be that the conditions to form the compound of formula V include a coupling agent, where the coupling agent may be any one or more of the previously described coupling agents. In any of the above embodiments, it may be that the conditions to form the compound of formula VIII include EDC and HOBT, EDC-HCl and HOBT, BOP and HOBT, or HATU and HOAT.

In any of the above embodiments, it may be that the conditions to form the compound of formula VIII further include a solvent. Such solvents include, but are not limited to, alcohols (e.g., methanol (CH$_3$OH), ethanol (EtOH), isopropanol (iPrOH), trifluorethanol (TFE), butanol (BuOH)), halogenated sovlents (e.g., methylene chloride (CH$_2$Cl$_2$), chloroform (CHCl$_3$), benzotrifluoride (BTF; PhCF$_3$)), ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), amides (e.g., dimethylformamide (DMF), dimethylacetamide (DMA)), nitriles (e.g., acetonitrile (CH$_3$CN), proprionitrile (CH$_3$CH$_2$CN), benzonitrile (PhCN)), sulfoxides (e.g., dimethyl sulfoxide), sulfones (e.g., sulfolane), water, or mixtures of any two or more thereof. In such embodiments, the solvent may include methanol (CH$_3$OH), ethanol (EtOH), isopropanol (iPrOH), trifluorethanol (TFE), butanol (BuOH), methylene chloride (CH$_2$Cl$_2$), chloroform (CHCl$_3$), benzotrifluoride (BTF; PhCF$_3$), tetrahydrofuran (THF), 2-methyltetrahydrofuran (2Me-THF), dimethoxyethane (DME), dioxane, ethyl acetate, isopropyl acetate, acetone, methylethyl ketone, methyl isobutyl ketone, dimethylformamide (DMF), dimethylacetamide (DMA), acetonitrile (CH$_3$CN), proprionitrile (CH$_3$CH$_2$CN), benzonitrile (PhCN), dimethyl sulfoxide, sulfolane, water, or a mixture of any two or more thereof. In any of the above embodiments, it may be that the conditions to form the compound of formula VIII further include a base.

In any of the above embodiments, it may be that the cleaving acid used to produce a compound of formula VI comprises a halogen acid, a carboxylic acid, a phosphonic acid, a phosphoric acid, a sulfinic acid, a sulfonic acid, a sulfuric acid, a sulfamic acid, a boric acid, a boronic acid, an acid resin, or combinations of any two or more thereof. In any of the above embodiments, it may be that the cleaving acid used to produce a compound of formula VI includes hydrofluoric acid, hydrochloric acid (HCl), hydrobromic acid, hydroiodic acid, acetic acid (AcOH), fluoroacetic acid, trifluoroacetic acid (TFA), chloroacetic acid, benzoic acid, phosphoric acid, methanesulfonic acid, benzenesulfonic acid, p-toluene sulfonic acid, trifluoromethanesulfonic acid, sulfuric acid, or combinations of any two or more thereof. In any of the above embodiments, it may be that combining with the cleaving acid occurs at a temperature from about −40° C. to about 150° C.

In any of the above embodiments, it may be that combining with the cleaving acid further includes a protic solvent, a polar aprotic solvent, or a mixture of the two. Protic solvents as used herein include, but are not limited to, alcohols (e.g., methanol (CH₃OH), ethanol (EtOH), isopropanol (iPrOH), trifluorethanol (TFE), butanol (BuOH)), carboxylic acids (e.g., formic acid, acetic acid, propanoic acid, butanoic acid, pentanoic acid, lauric acid, stearic acid, deoxycholic acid, glutamic acid, glucuronic acid), water, or mixtures of any two or more thereof. Polar aprotic solvents as used herein include halogenated sovlents (e.g., methylene chloride (CH₂Cl₂), chloroform (CHCl₃), benzotrifluoride (BTF; PhCF₃)), ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), amides (e.g., dimethylformamide (DMF), dimethylacetamide (DMA)), nitriles (e.g., acetonitrile (CH₃CN), proprionitrile (CH₃CH₂CN), benzonitrile (PhCN)), sulfoxides (e.g., dimethyl sulfoxide), sulfones (e.g., sulfolane), or mixtures of any two or more thereof. In any of the above embodiments, it may be that combining with the cleaving acid further includes methanol (CH₃OH), ethanol (EtOH), isopropanol (iPrOH), trifluorethanol (TFE), butanol (BuOH), methylene chloride (CH₂Cl₂), chloroform (CHCl₃), benzotrifluoride (BTF; PhCF₃), tetrahydrofuran (THF), 2-methyltetrahydrofuran (2Me-THF), dimethoxyethane (DME), dioxane, ethyl acetate, isopropyl acetate, acetone, methylethyl ketone, methyl isobutyl ketone, dimethylformamide (DMF), dimethylacetamide (DMA), acetonitrile (CH₃CN), proprionitrile (CH₃CH₂CN), benzonitrile (PhCN), dimethyl sulfoxide, sulfolane, water, or mixtures of any two or more thereof.

In any of the above embodiments, it may be that forming the compound of formula III involves converting a compound of formula XV

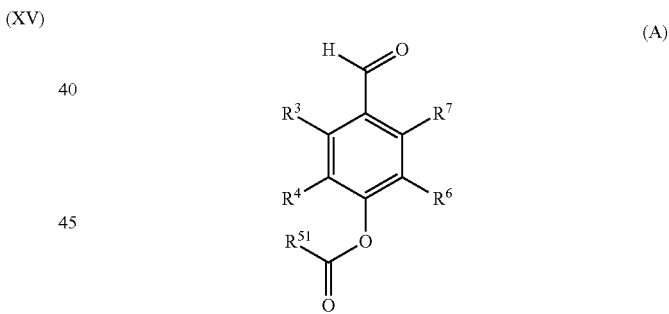

to a compound of formula III, wherein $R^{50}$ and $R^{51}$ are each independently hydrogen or a substituted or unsubstituted $C_1$-$C_6$ alkyl, aryl, or cycloalkyl group. In any of the above embodiments, it may be that $R^3$ and $R^7$ are methyl. In any of the above embodiments, it may be that $R^{50}$ and $R^{51}$ are methyl. In any of the above embodiments, it may be that $R^4$ and $R^6$ are each hydrogen. In any of the above embodiments, it may be that converting of the compound of formula XV to the compound of formula III involves combining the compound of formula XV with $Y^1$-Lv, an organic base, and an appropriate solvent to produce a product; and subjecting the product to ester hydrolysis conditions; wherein Lv is a halogen, —O—$Y^1$, or —O—C(O)Cl. In any of the above embodiments, it may be that $Y^1$ is Boc and $Y^1$-Lv is Boc₂O.

In any of the above embodiments, it may be that the ester hydrolysis conditions include an aqueous solution of an alkali metal hydroxide or an alkaline earth metal hydroxide. In any of the above embodiments, it may be that the ester hydrolysis conditions include an aqueous solution of NaOH.

In any of the above embodiments, it may be that the compound of formula XV is prepared by converting a compound of formula XIV

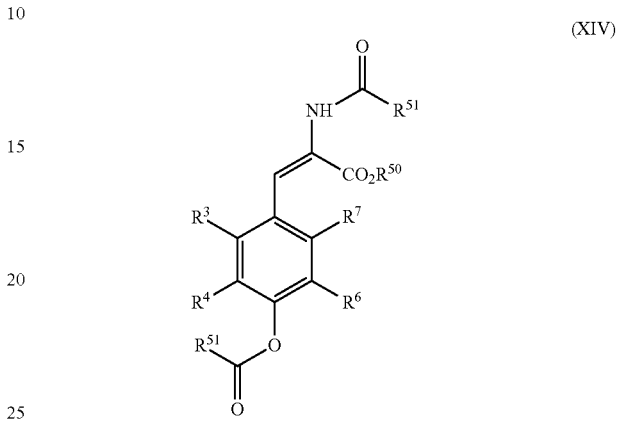

under conditions to form the compound of formula XV. In such embodiments, it may be that the conditions include a hydrogen source, a transition metal source, a chiral ligand and an appropriate solvent. In such embodiments, it may be that the conditions include H₂, Rh(I)(COD)₂BF₄, (S)-Me-BoPhos and THF.

In any of the above embodiments, it may be that forming the compound of formula XIV involves combining a compound of formula A

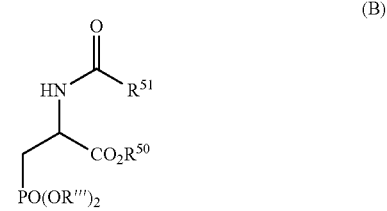

with a compound of formula B or a salt thereof (B)

under conditions to form the compound of formula XIV, where R''' at each occurrence is independently a substituted or unsubstituted alkyl, alkenyl, cycloalkyl, cycloalkylalkyl, aryl, aralkyl, heteroaryl, heteroarylalkyl, heterocyclyl, or heterocyclylalkyl group.

In any of the above embodiments, it may be that the conditions to form the compound of formula XIV involve a one pot synthesis. In any of the above embodiments, it may be that the one-pot synthesis involves combining the compound of formula A with the compound of formula B and further combining an organic base. In any of the above embodiments, it may be that the organic base is DBU or DIPEA. In any of the above embodiments, it may be that R'" is methyl. In any of the above embodiments, it may be that $R^3$, $R^7$, $R^{50}$ and $R^{51}$ are each methyl and $R^4$ and $R^6$ are each hydrogen.

In any of the above embodiments, it may be that forming the compound of formula XIV involves combining a compound of formula XII

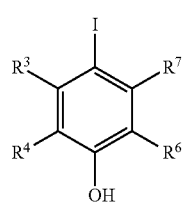

(XII)

with a compound of formula XIII or a salt thereof

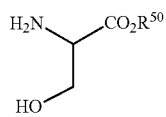

(XIII)

under conditions to form the compound of formula XIV.

In any of the above embodiments, it may be that the conditions to form the compound of formula XIV involve a one pot synthesis. In any of the above embodiments, it may be that the one-pot synthesis involves (a) combining the compound of formula XII and the compound of formula XIII with $(R^{51}CO)_2O$ in the presence of an organic base to form a mixture; and (b) adding a transition metal source and $PR^{52}_3$ to the mixture of (a); wherein each $R^{52}$ is independently substituted or unsubstituted $C_1$-$C_6$ alkyl group, unsubstituted phenyl, or phenyl substituted with 1 to 5 substituted or unsubstituted $C_1$-$C_6$ alkyl groups. In any of the above embodiments, it may be that the organic base is $Et_3N$. In any of the above embodiments, it may be that $PR^{52}_3$ is $P(tolyl)_3$. In any of the above embodiments, it may be that the transition metal source is $Pd(OAc)_2$. In any of the above embodiments, it may be that $R^3$, $R^7$, $R^{50}$ and $R^{51}$ are each methyl and $R^4$ and $R^6$ are each hydrogen.

DETAILED DESCRIPTION

Definitions

The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a", "an" and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the invention. Procedures for inserting such labels into the compounds of the invention will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyl; alkoxy, alkenoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Cycloalkyl groups may be substituted or unsubstituted. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Cycloalkylalkyl groups may be substituted or unsubstituted. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, among others. Alkenyl groups may be substituted or unsubstituted. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, butadienyl, pentadienyl, and hexadienyl. Cycloalkenyl groups may be substituted or unsubstituted.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Alkynyl groups may be substituted or unsubstituted. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. The phrase "aryl groups" includes groups containing fused rings, such as fused aromatic-aliphatic ring systems (e.g., indanyl, tetrahydronaphthyl, and the like). The phrase "aryl groups" also includes substituted aryl groups. Groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above. In some embodiments, the aryl group is phenyl, which can be substituted or unsubstituted. In some embodiments, substituted phenyl groups have one or two substituents. In some embodiments, substituted phenyl groups have one substituent.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Aralkyl groups may be substituted or unsubstituted. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups are non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass partially unsaturated and saturated ring systems, such as, for example, imidazolinyl and imidazolidinyl groups. The phrase also includes bridged polycyclic ring systems containing a heteroatom such as, but not limited to, quinuclidyl. The phrase also includes heterocyclyl groups that have other groups, such as alkyl, oxo or halo groups, bonded to one of the ring members, referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, pyrrolinyl, piperidyl, piperazinyl, morpholinyl, thiomorpholinyl, tetrahydropyranyl, and tetrahydrothiopyranyl groups. Representative substituted heterocyclyl groups may be mono-substituted or substituted more than once, such as, but not limited to, morpholinyl groups, which are 2-, 3-, 4-, 5-, or 6-substituted, or disubstituted with various substituents such as those listed above. The heteroatom(s) can also be in oxidized form, if chemically possible.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. The phrase "heteroaryl groups" includes fused ring compounds and also includes heteroaryl groups that have other groups bonded to one of the ring members, such as alkyl groups, referred to as "substituted heteroaryl groups." Representative substituted heteroaryl groups may be substituted one or more times with various substituents such as those listed above. The heteroatom(s) can also be in oxidized form, if chemically possible.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, and tetrahydrofuran-2-yl-ethyl. Representative substituted heterocyclylalkyl groups may be substituted one or more times with substituents such as those listed above. The heteroatom(s) can also be in oxidized form, if chemically possible.

Heteroaralkyl groups are alkyl groups as defined above in which a hydrogen or carbon bond of an alkyl group is replaced with a bond to a heteroaryl group as defined above. Heteroaralkyl may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above. The heteroatom(s) can also be in oxidized form, if chemically possible.

Groups described herein having two or more points of attachment (i.e., divalent, trivalent, or polyvalent) within the compound of the invention are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the invention are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Like alkyl groups, alkoxy groups may be linear or branched. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —C(O)OH group or to its ionized form, —C(O)O$^-$.

The term "ester" as used herein refers to —C(O)OR$^{60}$ groups. R$^{60}$ is a substituted or unsubstituted alkyl, cycloalkyl, alkenyl, alkynyl, aryl, aralkyl, heterocyclylalkyl or heterocyclyl group as defined herein. The term ester also refers to —OC(O)R$^{60}$ groups. For example, an ester may be —OC(O)-alkyl, —OC(O)-aryl, or —OC(O)-aralkyl, wherein each alkyl, aryl, or aralkyl group is substituted or unsubstituted.

The term "amide" (or "amido") includes C- and N-amide groups, i.e., —C(O)NR$^{61}$R$^{62}$, and —NR$^{61}$C(O)R$^{62}$ groups, respectively. R$^{61}$ and R$^{62}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{61}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{63}$C(O)OR$^{64}$ and —OC(O)NR$^{63}$R$^{64}$ groups, respectively. R$^{63}$ and R$^{64}$ are independently a substituted or unsubstituted alkyl, alkenyl, alkynyl, cycloalkyl, aryl, aralkyl, heterocyclylalkyl, or heterocyclyl group as defined herein. R$^{63}$ may also be H.

The term "amine" (or "amino") as used herein refers to —NR$^{65}$R$^{66}$ groups, wherein R$^{65}$ and R$^{66}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{68}$R$^{69}$ and —NR$^{68}$SO$_2$R$^{69}$ groups, respectively. R$^{68}$ and R$^{69}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while sulfides include —SR$^{70}$ groups, sulfoxides include —S(O)R$^{71}$ groups, sulfones include —SO$_2$R$^{72}$ groups, and sulfonyls include —SO$_2$OR$^{73}$. R$^{70}$, R$^{71}$, R$^{72}$, and R$^{73}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{74}$—C(O)—NR$^{75}$R$^{76}$ groups. R$^{74}$, R$^{75}$, and R$^{76}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{77}$)NR$^{78}$R$^{79}$ and —NR$^{77}$C(NR$^{78}$)R$^{79}$, wherein R$^{77}$, R$^{78}$, and R$^{79}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{80}$C(NR$^{18}$)NR$^{82}$R$^{83}$, wherein R$^{80}$, R$_{81}$, R$_{82}$ and R$^{83}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{84}$)=C(R$^{85}$)NR$^{86}$R$^{87}$ and —NR$^{84}$C(R$^{85}$)=C(R$^{86}$)R$^{87}$, wherein R$^{84}$, R$^{85}$, R$^{86}$ and R$^{87}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxy" as used herein can refer to —OH or its ionized form, —O$^-$.

The term "imide" refers to —C(O)NR$^{88}$C(O)R$^{89}$, wherein R$^{88}$ and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{90}$(NR$^{71}$) and —N(CR$^{90}$R$^{91}$) groups, wherein R$^{90}$ and R$^{91}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{90}$ and R$^{91}$ are not both simultaneously hydrogen.

The term "nitro" as used herein refers to an —NO$_2$ group.

The term "perhaloalkyl" as used herein refers to an alkyl group as defined above wherein every bond to hydrogen is replaced with a bond to a halogen. An example of a perhaloalkyl group is a trifluoromethyl group. The term "trifluoromethyl" as used herein refers to —CF$_3$.

The term "trifluoromethoxy" as used herein refers to —OCF$_3$.

Those of skill in the art will appreciate that compounds of the invention may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the invention encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, imidazoles may exhibit the following isomeric forms, which are referred to as tautomers of each other:

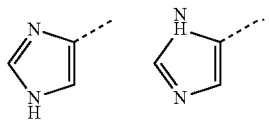

As readily understood by one skilled in the art, a wide variety of functional groups and other structures may exhibit tautomerism, and all tautomers of compounds as described herein are within the scope of the present invention.

Stereoisomers of compounds (also known as optical isomers) include all chiral, diastereomeric, and racemic forms of a structure, unless the specific stereochemistry is expressly indicated. Thus, compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the invention.

The compounds of the invention may exist as solvates, especially hydrates. Hydrates may form during manufacture of the compounds or compositions comprising the compounds, or hydrates may form over time due to the hygroscopic nature of the compounds. Compounds of the invention may exist as organic solvates as well, including amide (e.g., DMF), ether, ester, ketone, nitrile, and alcohol solvates among others. The identification and preparation of any particular solvate is within the skill of the ordinary artisan of synthetic organic or medicinal chemistry.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis,* 3rd Ed. (John Wiley & Sons, Inc., New York). Amino protecting groups include, but are not limited to, mesitylenesulfonyl (Mts), benzyloxycarbonyl (Cbz or Z), 2-chlorobenzyloxycarbonyl, t-butyloxycarbonyl (Boc), t-butyldimethylsilyl (TBS or TBDMS), 9-fluorenylmethyloxycarbonyl (Fmoc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, α-,α-dimethyldimethoxybenzyloxycarbonyl (DDZ), 5-bromo-7-nitroindolinyl, and the like. Amino protecting groups susceptible to acid-mediated removal include but are not limited to Boc and TBDMS. Amino protecting groups resistant to acid-mediated removal and susceptible to hydrogen-mediated removal include but are not limited to allyloxycarbonyl, Cbz, nitro, and 2-chlorobenzyloxycarbonyl. Hydroxyl protecting groups include, but are not limited to, Fmoc, TBS, photolabile protecting groups (such as nitroveratryl oxymethyl ether (Nvom)), Mom (methoxy methyl ether), and Mem (methoxyethoxy methyl ether), NPEOC (4-nitrophenethyloxycarbonyl) and NPEOM (4-nitrophenethyloxymethyloxycarbonyl). Examples and methods to synthesize the above phosphate substituted and/or sulfate substituted RPBQ compounds are disclosed in Published US Patent Application No. 20070225261A1.

As used herein, an "isolated" or "purified" polypeptide or peptide is substantially free of other contaminating polypeptides such as those peptides or polypeptides from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include other proteinaceous and nonproteinaceous solutes.

As used herein, the term "net charge" refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "small molecule" includes organic compounds, organometallic compounds, salts of organic and organometallic compounds, monosaccharides, amino acids, and nucleotides. Small molecules can further include molecules that would otherwise be considered biological molecules, except their molecular weight is not greater than 1,000. Thus, small molecules may be lipids, oligosaccharides, oligopeptides, and oligonucleotides, and their derivatives, having a molecular weight of 1,000 or less.

Peptides and Methods of the Present Technology

In one aspect, peptides (as disclosed herein) also include all stereoisomers and geometric isomers of the peptides, including diastereomers, enantiomers, and cis/trans (E/Z) isomers. In some embodiments, the amino acids of the peptides are D amino acids.

In some embodiments, the peptides are defined by formula I.

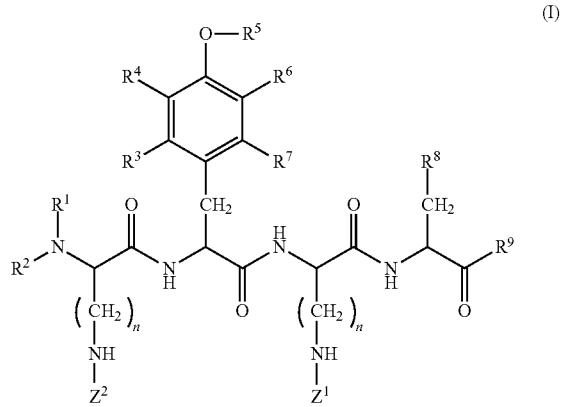

wherein $R^1$ and $R^2$ are each independently selected from
(i) hydrogen;
(ii) substituted or unsubstituted $C_1$-$C_6$ alkyl;
(iii) substituted or unsubstituted aralkyl;
(iv) substituted or unsubstituted cycloalkylalkyl;
(v) substituted or unsubstituted $C_2$-$C_6$ alkenyl;
(vi) an amino protecting group;

or R$^1$ and R$^2$ together form a 3, 4, 5, 6, 7, or 8 membered substituted or unsubstituted heterocyclyl ring;

R$^3$, R$^4$, R$^6$, and R$^7$ are each independently selected from hydrogen, or a C$_1$-C$_6$ alkyl, C$_1$-C$_6$ alkoxy, amino, C$_1$-C$_4$ alkylamino, C$_1$-C$_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

R$^5$ is selected from hydrogen, or a C$_1$-C$_6$ alkyl, aralkyl, —C(O)-alkyl, —C(O)-aryl, or —C(O)— aralkyl group, wherein each alkyl, aryl or aralkyl group is substituted or unsubstituted;

R$^8$ is

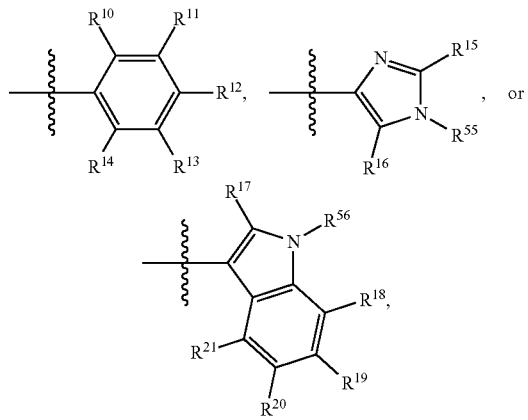

where R$^{10}$, R$^{11}$, R$^{12}$, R$^{13}$, R$^{14}$, R$^{15}$, R$^{16}$, R$^{17}$, R$^{18}$, R$^{19}$, R$^{20}$, and R$^{21}$ are each independently selected from H, or a C$_1$-C$_6$ alkyl, C$_1$-C$_6$ alkoxy, amino, C$_1$-C$_4$ alkylamino, C$_1$-C$_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted; R$^{55}$ and R$^{56}$ are each independently selected from H, or a C$_1$-C$_6$ alkyl, C$_1$-C$_6$ alkoxy, amino, C$_1$-C$_4$ alkylamino, C$_1$-C$_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

R$^9$ is OR' or NR'R'';

R' at each occurrence is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

R'' is a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group Z$^1$ and Z$^2$ are each independently hydrogen, —C(NH)—NH$_2$, or a substituted or unsubstituted alkyl, aryl, or aralkyl group;

n is 1, 2, 3, 4, or 5; and m is 1, 2, 3, 4, or 5.

In some embodiments, R$^1$, R$^2$, R$^4$, R$^5$, and R$^6$ are each hydrogen; R$^3$ and R$^7$ are each methyl; R$^8$ is

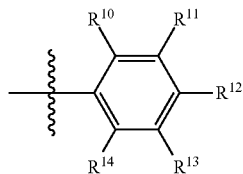

where R$^{10}$, R$^{11}$, R$^{12}$, R$^{13}$, and R$^{14}$ are all hydrogen; R$^9$ is NH$_2$; Z$^1$ is hydrogen, Z$^2$ is —C(NH)—NH$_2$; n is 4; and m is 3.

In some embodiments, the peptide is defined by formula II:

(II)

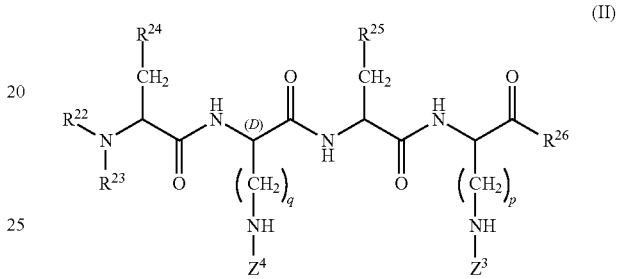

wherein R$^{22}$ and R$^{23}$ are each independently
(i) hydrogen;
(ii) substituted or unsubstituted C$_1$-C$_6$ alkyl;
(iii) substituted or unsubstituted aralkyl;
(iv) substituted or unsubstituted cycloalkylalkyl;
(v) substituted or unsubstituted C$_2$-C$_6$ alkenyl;
(vi) an amino protecting group;
or R$^{22}$ and R$^{23}$ together form a 3, 4, 5, 6, 7, or 8 membered substituted or unsubstituted heterocyclyl ring;

R$^{24}$ and R$^{25}$ are each independently

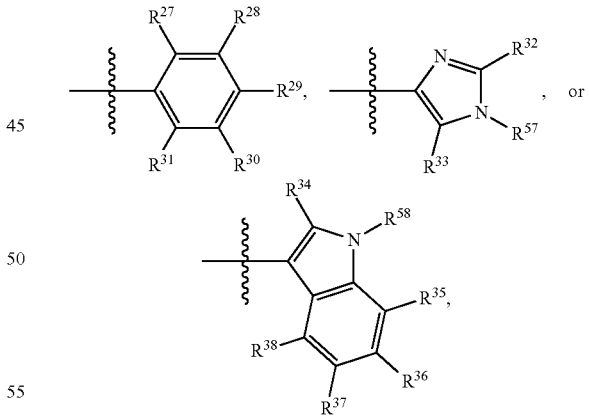

where R$^{27}$, R$^{28}$, R$^{29}$, R$^{30}$, R$^{31}$, R$^{32}$, R$^{33}$, R$^{34}$, R$^{35}$, R$^{36}$, R$^{37}$, and R$^{38}$ are each independently hydrogen, or a C$_1$-C$_6$ alkyl, C$_1$-C$_6$ alkoxy, amino, C$_1$-C$_4$ alkylamino, C$_1$-C$_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted; and R$^{57}$ and R$^{58}$ are each independently hydrogen, or a C$_1$-C$_6$ alkyl, C$_1$-C$_6$ alkoxy, amino, C$_1$-C$_4$ alkylamino, C$_1$-C$_4$ dialkylamino, cyano, —C(O)-alkyl, —C(O)-aryl, —C(O)-aralkyl, carboxylate, ester, amide, nitro, hydroxyl, halogen, or perhaloalkyl group, wherein each alkyl, aryl or aralkyl group is substituted or unsubstituted;

$R^{26}$ is $OR^{39}$ or $NR^{39}R^{40}$;

$R^{39}$ at each occurrence is independently a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

$R^{40}$ is a hydrogen, or a substituted or unsubstituted alkyl, alkenyl, cycloalkyl, cycloalkylalkyl, aryl, aralkyl, heteroaryl, heteroarylalkyl, heterocyclyl, or heterocyclylalkyl group;

$Z^3$ and $Z^4$ are each independently hydrogen, —C(NH)—NH$_2$, or a substituted or unsubstituted alkyl, aryl, or aralkyl group;

p is 1, 2, 3, 4, or 5; and q is 1, 2, 3, 4, or 5.

In a particular embodiment, $R^{22}$ and $R^{23}$ are each hydrogen, $R^{24}$ and $R^{25}$ are each

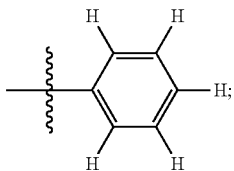

$R^{26}$ is NH$_2$, $Z^3$ is hydrogen, $Z^4$ is —C(NH)—NH$_2$, p is 4, and q is 3. In another embodiment, $R^{22}$ and $R^{23}$ are each hydrogen; $R^{24}$ is

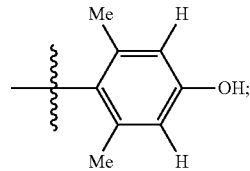

$R^{25}$ is

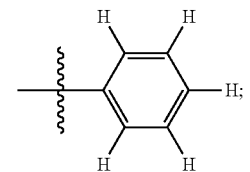

$R^{26}$ is NH$_2$; $Z^3$ is hydrogen; $Z^4$ is —C(NH)—NH$_2$; p is 4; and q is 3.

In some embodiments, the peptide includes one or more of the peptides of Table A:

TABLE A

Phe-Arg-D-His-Asp
Met-Tyr-D-Lys-Phe-Arg
Phe-D-Arg-His
Tyr-D-Arg-Phe-Lys-NH$_2$
2'6'-Dmt-D-Arg-Phe-Lys-NH$_2$
2'6'-Dmt-D-Arg-Phe Orn-NH$_2$
2'6'-Dmt-D-Cit-Phe Lys-NH$_2$
Phe-D-Arg-2'6'-Dmt-Lys-NH$_2$
2'6'-Dmt-D-Arg-Phe-Ahp-NH$_2$
H-Phe-D-Arg-Phe-Lys-Cys-NH$_2$
2'6'-Dmp-D-Arg-2'6'-Dmt-Lys-NH$_2$
2'6'-Dmp-D-Arg-Phe-Lys-NH$_2$
Tyr-Arg-Phe-Lys-Glu-His-Trp-D-Arg
Lys-Gln-Tyr-D-Arg-Phe-Trp
D-Arg-2'6'-Dmt-Lys-Trp-NH$_2$
D-Arg-Trp-Lys-Trp-NH$_2$
D-Arg-2'6'-Dmt-Lys-Phe-Met-NH$_2$
D-Arg-2'6'-Dmt-Lys(N$^\alpha$Me)-Phe-NH$_2$
D-Arg-2'6'-Dmt-Lys-Phe(NMe)-NH$_2$
D-Arg-2'6'-Dmt-Lys(N$^\alpha$Me)-Phe(NMe)-NH$_2$
D-Arg(N$^\alpha$Me)-2'6'-Dmt(NMe)-Lys(N$^\alpha$Me)-Phe(NMe)-NH$_2$
D-Arg-2'6'-Dmt-Lys-Phe-Lys-Trp-NH$_2$
D-Arg-2'6'-Dmt-Lys-2'6'-Dmt-Lys-Trp-NH$_2$
D-Arg-2'6'-Dmt-Lys-Phe-Lys-Met-NH$_2$
D-Arg-2'6'-Dmt-Lys-2'6'-Dmt-Lys-Met-NH$_2$
D-Arg-2'6'-Dmt-Lys-Phe-Sar-Gly-Cys-NH$_2$
D-Arg-Ψ[CH$_2$—NH]2'6'-Dmt-Lys-Phe-NH$_2$
D-Arg-2'6'-Dmt-Ψ[CH$_2$—NH]Lys-Phe-NH$_2$
D-Arg-2'6'-Dmt-LysΨ[CH$_2$—NH]Phe-NH$_2$
D-Arg-2'6'-Dmt-Ψ[CH$_2$—NH]Lys-Ψ[CH$_2$—NH]Phe-NH$_2$
Lys-D-Arg-Tyr-NH$_2$
D-Tyr-Trp-Lys-NH$_2$
Trp-D-Lys-Tyr-Arg-NH$_2$
Tyr-His-D-Gly-Met
Tyr-D-Arg-Phe-Lys-Glu-NH$_2$
Met-Tyr-D-Arg-Phe-Arg-NH$_2$
D-His-Glu-Lys-Tyr-D-Phe-Arg
Lys-D-Gln-Tyr-Arg-D-Phe-Trp-NH$_2$
Phe-D-Arg-Lys-Trp-Tyr-D-Arg-His
Gly-D-Phe-Lys-His-D-Arg-Tyr-NH$_2$
Val-D-Lys-His-Tyr-D-Phe-Ser-Tyr-Arg-NH$_2$
Trp-Lys-Phe-D-Asp-Arg-Tyr-D-His-Lys
Lys-Trp-D-Tyr-Arg-Asn-Phe-Tyr-D-His-NH$_2$
Thr-Gly-Tyr-Arg-D-His-Phe-Trp-D-His-Lys TABLE A-continued Asp-D-Trp-Lys-Tyr-D-His-Phe-Arg-D-Gly-Lys-NH$_2$
D-His-Lys-Tyr-D-Phe-Glu-D-Asp-D-Asp-D-His-D-Lys-Arg-Trp-NH$_2$
Ala-D-Phe-D-Arg-Tyr-Lys-D-Trp-His-D-Tyr-Gly-Phe
Tyr-D-His-Phe-D-Arg-Asp-Lys-D-Arg-His-Trp-D-His-Phe
Phe-Phe-D-Tyr-Arg-Glu-Asp-D-Lys-Arg-D-Arg-His-Phe-NH$_2$
Phe-Tyr-Lys-D-Arg-Trp-His-D-Lys-D-Lys-Glu-Arg-D-Tyr-Thr
Tyr-Asp-D-Lys-Tyr-Phe-D-Lys-D-Arg-Phe-Pro-D-Tyr-His-Lys
Glu-Arg-D-Lys-Tyr-D-Val-Phe-D-His-Trp-Arg-D-Gly-Tyr-Arg-D-Met-NH$_2$
Arg-D-Leu-D-Tyr-Phe-Lys-Glu-D-Lys-Arg-D-Trp-Lys-D-Phe-Tyr-D-Arg-Gly
D-Glu-Asp-Lys-D-Arg-D-His-Phe-Phe-D-Val-Tyr-Arg-Tyr-D-Tyr-Arg-His-Phe-NH$_2$
Asp-Arg-D-Phe-Cys-Phe-D-Arg-D-Lys-Tyr-Arg-D-Tyr-Trp-D-His-Tyr-D-Phe-Lys-Phe
His-Tyr-D-Arg-Trp-Lys-Phe-D-Asp-Ala-Arg-Cys-D-Tyr-His-Phe-D-Lys-Tyr-His-Ser-NH$_2$
Gly-Ala-Lys-Phe-D-Lys-Glu-Arg-Tyr-His-D-Arg-D-Arg-Asp-Tyr-Trp-D-His-Trp-His-D-Lys-Asp
Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$ 2',6'-dimethyltyrosine (2'6'-Dmt or Dmt)
2',6'-dimethylphenylalanine (2'6'-Dmp or Dmp)
In some embodiments, the peptide includes the amino acid sequence 2'6'-Dmt-D-Arg-Phe-Lys-NH$_2$, Phe-D-Arg-Phe-Lys-NH$_2$, or D-Arg-2'6'-Dmt-Lys-Phe-NH$_2$. In some embodiments, the peptide includes the amino acid sequence D-Arg-2'6'-Dmt-Lys-Phe-NH$_2$.

The peptides disclosed herein may be formulated as pharmaceutically acceptable salts. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, alkylammonium, calcium, cupric, cuprous, nickel, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, diisopropylethylamine, ethanolamine, ethylenediamine, N-ethylmorpholine, N-ethylpiperidine, glucamine, glucosamine, histidine, hydrabamine, imidazole, isopropylamine, lysine, methylglucamine, morpholine, N-methylmorpholine, piperazine, piperidine, pyridine, lutidine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, phosphorous, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), fatty acids (lauric, myristic, oleic, stearic, palmitic), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate salt. Additionally or alternatively, in other embodiments, the salt is a trifluoroacetate salt. In some embodiments, the salt is a tartrate salt.

In some embodiments, a pharmaceutical salt is provided comprising the peptides of formulas I and/or II and pharmaceutically acceptable acid. Pharmaceutically acceptable acids include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), and undecylenic acid. In some embodiments, the pharmaceutically acceptable acid is tartaric acid.

In some embodiments, the peptide is of formula I, $R^1$, $R^2$, $R^4$, $R^5$, and $R^6$ are hydrogen; $R^3$ and $R^7$ are methyl; $R^8$ is $R^8$ is

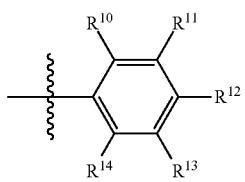

where $R^{10}$, $R^{11}$, $R^{12}$, $R^{13}$, and $R^{14}$ are all hydrogen; $R^9$ is $NH_2$; $Z^1$ is hydrogen, $Z^2$ is —C(NH)—$NH_2$; n is 4; m is 3, and the pharmaceutically acceptable acid is tartaric acid. In a particular embodiment, the peptide is of formula II, $R^{22}$ and $R^{23}$ are each hydrogen, $R^{24}$ and $R^{25}$ are each

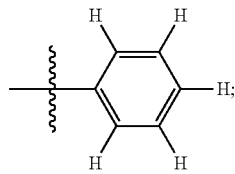

$R^{26}$ is $NH_2$, $Z^3$ is hydrogen, $Z^4$ is —C(NH)—$NH_2$, p is 4, and q is 3, and the pharmaceutically acceptable acid is tartaric acid. In another embodiment, the peptide is of formula II, $R^{22}$ and $R^{23}$ are each hydrogen; $R^{24}$ is

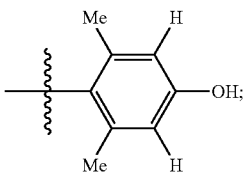 [SMILES: *c1c(C)cc(O)cc1C]

$R^{25}$ is

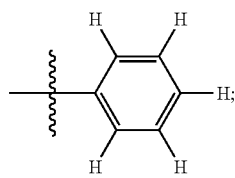

$R^{26}$ is $NH_2$; $Z^3$ is hydrogen; $Z^4$ is —C(NH)—$NH_2$; p is 4; and q is 3; and the pharmaceutically acceptable acid is tartaric acid.

In another aspect, a process is provided for synthesizing the compounds of the present technology. In some embodiments, the process is directed at producing one or more of the intermediates as the end product; in some embodiments, the process is directed at producing the compounds of the present technology as the end product of the process. Each embodiment may be performed independently of any other embodiment, or in combination with other embodiments. In any of the embodiments, it may be that the process is a solution phase process and not a solid phase process. In any of the embodiments, it may be that the purity of the product of the process is at least about 95% as determined by high performance liquid chromatography (HPLC). The purity may be about 98.2%, about 98.4%, about 98.6%, about 98.8%, about 99.0%, about 99.2%, about 99.4%, about 99.6%, about 99.8%, or any range including and between any two of these values or greater than any one of these values. In any of the embodiments, it may be that the product of the process may be at least about 98.0% pure as determined by gas chromatographic analysis. The purity may be about 98.2%, about 98.4%, about 98.6%, about 98.8%, about 99.0%, about 99.2%, about 99.4%, about 99.6%, about 99.8%, or any range including and between any two of these values or greater than any one of these values. In any of the embodiments, it may be the product has less than about 50 ppm heavy metals. The heavy metals may be about 45 ppm, about 40 ppm, about 35 ppm, about 30 ppm, about 25 ppm, about 20 ppm, about 15 ppm, about 10 ppm, about 5 ppm, about 1 ppm, or any range in between and including any two of these values or lower than any one of these values.

Thus, a process of preparing the compound of formula I

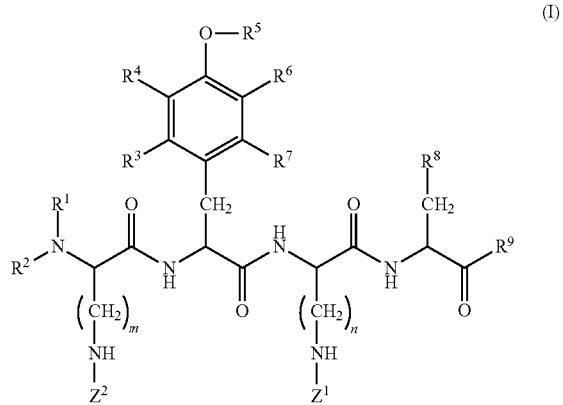

or a pharmaceutically acceptable salt thereof is provided. The process of preparing the compound of formula I may include any one or more of the embodiments and aspects described herein.

In some embodiments, the process includes combining a compound of formula III with a compound of formula IV:

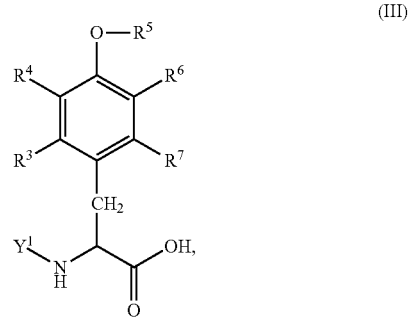

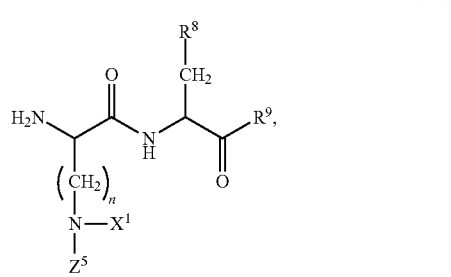

under conditions to form a compound of formula V:

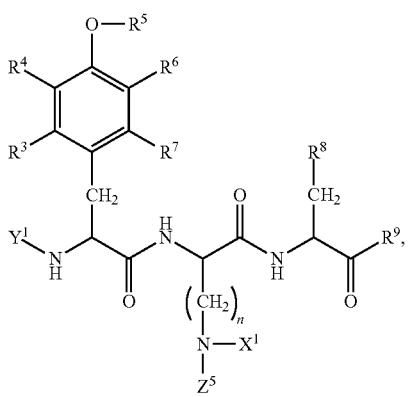

wherein $X^1$ at each occurrence is independently hydrogen or an amino protecting group resistant to acid-mediated removal and susceptible to hydrogen-mediated removal (e.g., molecular hydrogen); $X^2$ and $X^4$ at each occurrence are each independently hydrogen or an amino protecting group resistant to acid-mediated removal and susceptible to hydrogen-mediated removal; $Y^1$ is an amino protecting group susceptible to acid-mediated removal; and $Z^5$ is hydrogen, $-C(N-X^4)-NH-X^2$ or a substituted or unsubstituted alkyl, aryl, or aralkyl group; wherein at least one of $X^1$, $X^2$, $X^3$ and $X^4$ is an amino protecting group resistant to acid-mediated removal and susceptible to hydrogen-mediated removal. In any of the above embodiments, it may be that $Y^1$ is tert-butyloxycarbonyl (Boc); $X^1$ at each occurrence is independently hydrogen, allyloxycarbonyl, benzyloxycarbonyl (Cbz), or 2-chlorobenzyloxycarbonyl; $X^2$ at each occurrence is independently hydrogen, allyloxycarbonyl, benzyloxycarbonyl (Cbz), or 2-chlorobenzyloxycarbonyl; and $X^4$ at each occurrence is independently hydrogen, nitro, allyloxycarbonyl, benzyloxycarbonyl (Cbz), or 2-chlorobenzyloxycarbonyl. In some embodiments, when $Z^5$ is $-C(NH)-NH-X^2$, $X^1$ is hydrogen. In some embodiments, when $Z^5$ is $-C(N-X^4)-NH-X^2$, $X^1$ is hydrogen and at least one of $X^2$ and $X^4$ is not H. In any of the above embodiments, it may be that when $X^2$ is an amino protecting group resistant to acid-mediated removal and susceptible to hydrogen-mediated removal, $X^1$ is hydrogen. In any of the above embodiments, it may be that when $X^1$ is an amino protecting group resistant to acid-mediated removal and susceptible to hydrogen-mediated removal, $X^2$ is hydrogen. In any of the above embodiments, it may be that $R^3$ and $R^7$ are each methyl. In any of the above embodiments, it may be that $R^8$ is

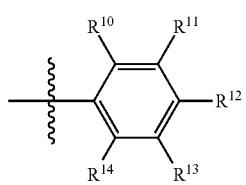

where $R^{10}$, $R^{11}$, $R^{12}$, $R^{13}$, and $R^{14}$ are all hydrogen. In any of the above embodiments, it may be that $R^9$ is $NH_2$. In any of the above embodiments, it may be that $Z^5$ is hydrogen, and n is 4. In any of the above embodiments, it may be that $R^3$ and $R^7$ are each methyl, $R^8$ is

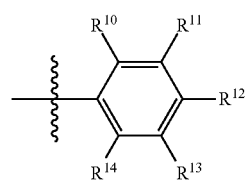

where $R^{10}$, $R^{11}$, $R^{12}$, $R^{13}$, and $R^{14}$ are all hydrogen; $R^9$ is $NH_2$; $Z^5$ is hydrogen; and n is 4. In any of the above embodiments, it may be that the process further includes isolating the compound of formula V.

In some embodiments, the conditions to form the compound of formula V include a coupling agent. The coupling agent of the present technology may be any suitable chemical useful for forming an amide bond from a primary amine and a carboxylic acid. Such coupling agents as used in any of the aspects and embodiments described herein may include water soluble carbodiimides such as 1-ethyl-3-(3-dimethylaminopropyl)carbodiimide (EDC) or the hydrochloride salt of EDC (EDC-HCl). Representative coupling agents include, but are not limited to, (7-azabenzotriazol-1-yloxy)tripyrrolidinophosphonium hexafluorophosphate (PyAOP), O-benzotriazol-1-yl-N,N,N',N'-bis(pentamethylene)uronium hexafluorophosphate, O-(benzotriazol-1-yl)-N,N,N',N'-bis(tetramethylene)uronium hexafluorophosphate, (benzotriazol-1-yloxy)dipiperidinocarbenium hexafluorophosphate, (benzotriazol-1-yloxy)tripyrrolidinophosphonium hexafluorophosphate (PyBOP), (benzotriazol-1-yloxy)tris(dimethylamino)phosphonium hexafluorophosphate (BOP), O-(benzotriazol-1-yl)-N,N,N',N'-tetramethyluronium tetrafluoroborate (TBTU), bromotripyrrolidinophosphonium hexafluorophosphate, Bromotris(dimethylamino)phosphonium hexafluorophosphate, O-(6-chlorobenzotriazol-1-yl)-N,N,N',N'-tetramethyluronium tetrafluoroborate (TCTU), O-(6-chlorobenzotriazol-1-yl)-N,N,N',N'-tetramethyluronium hexafluorophosphate (HCTU), 2-chloro-1,3-dimethylimidazolidinium hexafluorophosphate, 2-chloro-1,3-dimethylimidazolidinium tetrafluoroborate, 2-chloro-1,3-dimethylimidazolidinium chloride, chlorodipyrrolidinocarbenium hexafluorophosphate, chloro-N,N,N',N'-tetramethylformamidinium hexafluorophosphate, chlorotripyrrolidinophosphonium hexafluorophosphate, (1-cyano-2-ethoxy-2-oxoethylidenaminooxy)dimethylamino-morpholino-carbenium hexafluorophosphate (COMU), dipyrrolidino(N-succinimidyloxy)carbenium hexafluorophosphate, O-[(ethoxycarbonyl)cyanomethylenamino]-N,N,N',N'-tetramethyluronium hexafluorophosphate, fluoro-N,N,N',N'-bis(tetramethylene)formamidinium hexafluorophosphate, fluoro-N,N,N',N'-bis(tetramethylene) formamidinium hexafluorophosphate, 1-hydroxybenzotriazole (HOBT), 1-hydroxy-7-azabenzotriazole (HOAT), 1-[bis(dimethylamino)methylene]-1H-1,2,3-triazolo[4,5-b]pyridinium 3-oxide hexafluorophosphate (HATU), N,N,N',N'-tetramethyl-O-(1H-benzotriazol-1-yl)uronium hexafluorophosphate (HBTU), 1-[(dimethylamino)(morpholino)methylene]-1H-[1,2,3]triazolo[4,5-b]pyridine-1-ium 3-oxide hexafluorophosphate (HDMA), O-(5-norbornene-2,3-dicarboximido)-N,N,N',N'-tetramethyluronium tetrafluoroborate, S-(1-oxido-2-pyridyl)-N,N,N',N'-tetramethylthiuronium hexafluorophosphate, O-(2-oxo-1(2H)pyridyl)-N,N,N',N'-tetramethyluronium tetrafluoroborate, N,N,N',N'-tetramethyl-O—(N-succinimidyl)uronium hexafluorophosphate, N,N'-dicyclohexylcarbodiimide (DCC), N,N'-diisopropylcarbodiimide, 1-ethyl-3-(3-dimethylaminopropyl)carbodiimide (EDC), 1-[3-(dimethylamino)

propyl]-3-ethylcarbodiimide methiodide (EDC-MeI), propane phosphonic acid anhydride (T3P), N,N'-di-tert-butylcarbodiimide, N-cyclohexyl-N'-(2-morpholinoethyl) carbodiimide methyl-p-toluenesulfonate, 2-ethoxy-1-ethoxycarbonyl-1,2-dihydroquinoline, 1,1'-carbonyldiimidazole, 1,1'-carbonyldi(1,2,4-triazole), bis(4-nitrophenyl) carbonate, 4-nitrophenyl chloroformate, di(N-succinimidyl) carbonate, and 1-(2-mesitylenesulfonyl)-3-nitro-1H-1,2,4-triazole. In some embodiments, the coupling agent includes DCC, EDC, HATU, HBTU, HCTU, T3P, TBTU, TCTU, PyAOP, BOP, or PyBOP. In any of the above embodiments, it may be that the coupling agent is EDC and the conditions optionally include HOBT. In any of the above embodiments, the coupling agent may include BOP and the conditions optionally include HOBT. In any of the above embodiments, the coupling agent may include HATU and the conditions optionally include HOAT.

In any of the above embodiments, the conditions to form the compound of formula V may further include a suitable solvent. Such solvents include, but are not limited to, alcohols (e.g., methanol ($CH_3OH$), ethanol (EtOH), isopropanol (iPrOH), trifluorethanol (TFE), butanol (BuOH)), halogenated sovlents (e.g., methylene chloride ($CH_2Cl_2$), chloroform ($CHCl_3$), benzotrifluoride (BTF; $PhCF_3$)), ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), amides (e.g., dimethylformamide (DMF), dimethylacetamide (DMA)), nitriles (e.g., acetonitrile ($CH_3CN$), proprionitrile ($CH_3CH_2CN$), benzonitrile (PhCN)), sulfoxides (e.g., dimethyl sulfoxide), sulfones (e.g., sulfolane), water, or mixtures of any two or more thereof. In any of the above embodiments, it may be that the solvent includes $CH_3OH$, EtOH, iPrOH, TFE, BuOH, $CH_2Cl_2$, $CHCl_3$, $PhCF_3$, THF, 2Me-THF, DME, dioxane, ethyl acetate, isopropyl acetate, acetone, methylethyl ketone, methyl isobutyl ketone, DMF, DMA, $CH_3CN$, $CH_3CH_2CN$, PhCN, dimethylsulfoxide, sulfolane, water, or mixtures of any two or more thereof. In some embodiments, the solvent is dimethylformamide (DMF) or $CH_2Cl_2$. In any of the above embodiments, the conditions may further include a base. The base may be an inorganic base, such as $Na_2CO_3$ or $NaHCO_3$, or an organic base such as 1,8-diazabicyclo[5.4.0]undec-7-ene (DBU) or a trialkyl amine. Suitable trialkyl amines include, but are not limited to, trimethyl amine, triethyl amine, dimethylethyl amine, and diisopropylethyl amine. When the base includes an inorganic base, the suitable solvent may further include water.

In any of the above embodiments, it may be that the conditions to form the compound of formula V occur at a temperature from about −40° C. to about 150° C. Such an embodiment may be performed at about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., and any range including and between any two of these values.

In some embodiments, the process includes combining the compound of formula V with a cleaving acid to produce the compound of formula VI:

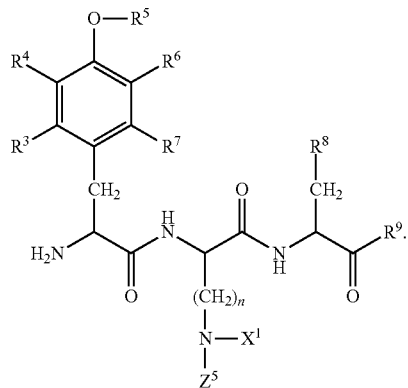

(VI)

In some embodiments, the process further includes isolating the compound of formula V.

Cleaving acids include halogen acids, carboxylic acids, phosphonic acids, phosphoric acids, sulfinic acids, sulfonic acids, sulfuric acids, sulfamic acids, boric acids, boronic acids, an acid resin, or combinations of any two or more thereof. Representative examples include, but are not limited to, hydrofluoric acid, hydrochloric acid (HCl), hydrobromic acid, hydroiodic acid, acetic acid (AcOH), fluoroacetic acid, trifluoroacetic acid (TFA), chloroacetic acid, benzoic acid, phosphoric acid, methanesulfonic acid, benzenesulfonic acid, p-toluene sulfonic acid, trifluoromethanesulfonic acid, and sulfuric acid. In some embodiments, the process includes any two or more of the aforementioned cleaving acids. The combining with the cleaving acid may occur at temperatures from about −40° C. to about 150° C. Such an embodiment may be performed at about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., and any range including and between any two of these values. In any of the above embodiments, it may be that after combining with the cleaving acid the temperature is raised to a temperature of about 10° C., 15° C., 20° C., 25° C., 30° C., 35° C., 40° C., 45° C., 50° C., or any range including and between any two of these values.

In some embodiments, the combining with the cleaving acid includes a protic solvent, a polar aprotic solvent, or a mixture of the two. Protic solvents as used herein include, but are not limited to, alcohols (e.g., methanol ($CH_3OH$), ethanol (EtOH), isopropanol (iPrOH), trifluorethanol (TFE), butanol (BuOH)), carboxylic acids (e.g., formic acid, acetic acid, propanoic acid, butanoic acid, pentanoic acid, lauric acid, stearic acid, deoxycholic acid, glutamic acid, glucuronic acid), water, or mixtures of any two or more thereof. Polar aprotic solvents as used herein include halogenated sovlents (e.g., methylene chloride ($CH_2Cl_2$), chloroform ($CHCl_3$), benzotrifluoride (BTF; $PhCF_3$)), ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), amides (e.g., dimethylformamide (DMF), dimethylacetamide (DMA)), nitriles (e.g., acetonitrile (CH₃CN), proprionitrile (CH₃CH₂CN), benzonitrile (PhCN)), sulfoxides (e.g., dimethyl sulfoxide), sulfones (e.g., sulfolane), or mixtures of any two or more thereof.

In some embodiments, the process includes combining the compound of formula VI with a compound of the formula VII:

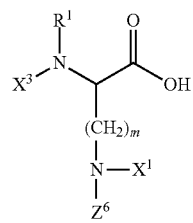

(VII)

under conditions to form a compound of formula VIII:

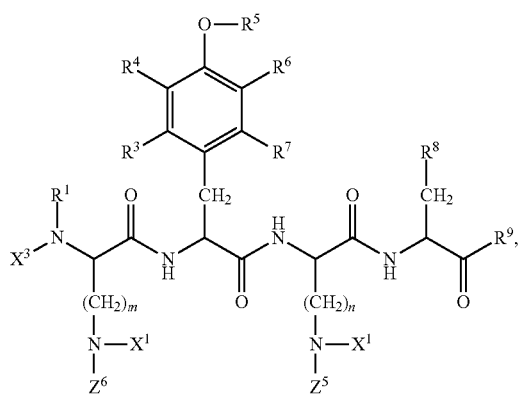

(VIII)

wherein $X^3$ is $X^1$ or $R^2$, and $Z^6$ is hydrogen, —C(N—X⁴)—NH—X² or a substituted or unsubstituted alkyl, aryl, or aralkyl group; wherein at least one of $X^1$, $X^2$, $X^3$ and $X^4$ is an amino protecting group resistant to acid-mediated removal and susceptible to hydrogen-mediated removal. In some embodiments, the process further includes isolating the compound of formula VIII. In some embodiments, if $X^3$ is $R^2$, then $R^1$ is not hydrogen. In some embodiments, if $X^3$ is $R^2$, then neither $R^1$ nor $R^2$ is hydrogen. In some embodiments, when $Z^5$ and/or $Z^6$ is —C(NH)—NH—X², $X^1$ is hydrogen. In some embodiments, when $Z^5$ and/or $Z^6$ is —C(N—X⁴)—NH—X², $X^1$ is hydrogen and at least one of $X^2$ and $X^4$ is not H. In some embodiments, when $X^2$ is an amino protecting group resistant to acid-mediated removal and susceptible to hydrogen-mediated removal, $X^1$ is hydrogen. In some embodiments, when $X^1$ is an amino protecting group resistant to acid-mediated removal and susceptible to hydrogen-mediated removal, $X^2$ is hydrogen. In any of the above embodiments, it may be that $Y^1$ is tert-butyloxycarbonyl (Boc); $X^1$ at each occurrence is independently hydrogen, allyloxycarbonyl, benzyloxycarbonyl (Cbz), or 2-chlorobenzyloxycarbonyl; $X^2$ at each occurrence is independently hydrogen, allyloxycarbonyl, benzyloxycarbonyl (Cbz), or 2-chlorobenzyloxycarbonyl; and $X^4$ at each occurrence is independently hydrogen, nitro, allyloxycarbonyl, benzyloxycarbonyl (Cbz), or 2-chlorobenzyloxycarbonyl. In any of the above embodiments, it may be that the conditions to form the compound of formula VIII further include a suitable solvent. Such solvents include, but are not limited to, alcohols (e.g., methanol (CH₃OH), ethanol (EtOH), isopropanol (iPrOH), trifluorethanol (TFE), butanol (BuOH)), halogenated solvents (e.g., methylene chloride (CH₂Cl₂), chloroform (CHCl₃), benzotrifluoride (BTF; PhCF₃)), ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), amides (e.g., dimethylformamide (DMF), dimethylacetamide (DMA)), nitriles (e.g., acetonitrile (CH₃CN), proprionitrile (CH₃CH₂CN), benzonitrile (PhCN)), sulfoxides (e.g., dimethyl sulfoxide), sulfones (e.g., sulfolane), water, or mixtures of any two or more thereof. In any of the above embodiments, it may be that the solvent includes CH₃OH, EtOH, iPrOH, TFE, BuOH, CH₂Cl₂, CHCl₃, PhCF₃, THF, 2Me-THF, DME, dioxane, ethyl acetate, isopropyl acetate, acetone, methylethyl ketone, methyl isobutyl ketone, DMF, DMA, CH₃CN, CH₃CH₂CN, PhCN, dimethylsulfoxide, sulfolane, water, or mixtures of any two or more thereof. In some embodiments, the suitable solvent includes dimethylformamide (DMF). In some embodiments, the suitable solvent includes dimethylacetamide (DMA). In some embodiments, the suitable solvent includes CH₂Cl₂.

In any of the above embodiments, it may be that the conditions to form the compound of formula VIII include a coupling agent as previously described. In such embodiments, the coupling agent included in the conditions to form the compound of formula VIII may be the same or different than the coupling agent included in the conditions to form the compound of formula V. In some embodiments, the coupling agent is selected from DCC, EDC, HATU, HBTU, HCTU, T3P, TBTU, TCTU, PyAOP, and PyBOP. In some embodiments, the coupling agent is EDC and the conditions optionally include HOBT. In some embodiments, the coupling agent is HATU and the conditions optionally include HOAT.

In any of the above embodiments, it may be that the process includes combining the compound of formula VIII with a hydrogen source and a transition metal catalyst to form the compound of formula I. The term "hydrogen source" means a source for providing two hydrogen atoms. In any of the embodiments and aspects described herein, it may be that the hydrogen source includes molecular hydrogen, formic acid, formate salts, diimide, cyclohexene, or cyclohexadiene. Formate salts include, but are not limited to, NH₄OC(O)H and may also be represented by $(M)_x(OCHO)_y$, where M is a alkali metal or an alkaline earth metal, x is 1, 2, or 3 and where y is 1, 2, or 3. In some embodiments, the hydrogen source is hydrogen gas. In any of the embodiments and aspects described herein, the transition metal catalyst includes cobalt (Co), iridium (Ir), molybdenum (Mo), nickel (Ni), platinum (Pt), palladium (Pd), rhodium (Rh), ruthenium (Ru), tungsten (W), or combinations of any two or more thereof. In some embodiments, the transition metal catalyst includes Pd. In any of the embodiments and aspects described herein, the transition metal catalyst includes a support material. Support materials include, but are not limited to, carbon, carbonate salts, silica, silicon, silicates, alumina, clay, or mixtures of any two or more thereof. For example, in some embodiments, the transition metal catalyst is Pd on carbon (Pd/C). In some embodiments, the transition metal catalyst is Pd on silicon (Pd/Si). In embodiments of the transition metal catalyst that include a support material, the amount of transition metal in the combined transition metal/support material mass may be from about 0.01 wt % to about 80 wt %. The amount of transition metal may be about 0.01 wt %, 0.05 wt %, 0.1 wt %, about 0.5 wt %, about 1 wt %, about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, or any range including and in between any two of these values. In some embodiments, the transition metal catalyst is Pd on carbon, and the amount of transition metal is 5 wt %, i.e., 5% Pd/C. In some embodiments, the transition metal catalyst is Pd on carbon, and the amount of transition metal is 10 wt %, i.e., 10% Pd/C. In some embodiments, the transition metal catalyst is Pd on silicon, and the amount of transition metal is 5 wt %, i.e., 5% Pd/Si. In some embodiments, the transition metal catalyst is Pd on silicon, and the amount of transition metal is 10 wt %, i.e., 10% Pd/Si. In any of the embodiments and aspects described herein, it may be that a solvent is included in addition to the hydrogen source and transition metal catalyst. Representative solvents include, but are not limited to, alcohols, halogenated sovlents, ethers, esters, ketones, amides, nitriles, sulfoxides, sulfones, water, or mixtures of any two or more thereof. In any of the above embodiments, it may be that the solvent includes $CH_3OH$, EtOH, iPrOH, TFE, BuOH, $CH_2Cl_2$, $CHCl_3$, $PhCF_3$, THF, 2Me-THF, DME, dioxane, ethyl acetate, isopropyl acetate, acetone, methylethyl ketone, methyl isobutyl ketone, DMF, DMA, $CH_3CN$, $CH_3CH_2CN$, PhCN, dimethylsulfoxide, sulfolane, water, or mixtures of any two or more thereof. In any of the embodiments and aspects described herein, the solvent may further include an acid. The acid may be present in a suitable amount, including a catalytic amount. Such acids include, but are not limited to, a mineral acid (e.g., HCl, HBr, HF, $H_2SO_4$, $H_3PO_4$, $HClO_4$), a carboxylic acid (e.g., formic acid, acetic acid, propanoic acid, butanoic acid, pentanoic acid, lauric acid, stearic acid, deoxycholic acid, glutamic acid, glucuronic acid), boronic acid, a sulfinic acid, a sulfamic acid, or mixtures of any two or more thereof. In any of the above embodiments, it may be that the solvent further includes, HCl, HBr, HF, $H_2SO_4$, $H_3PO_4$, $HClO_4$, formic acid, acetic acid, propanoic acid, butanoic acid, pentanoic acid, lauric acid, stearic acid, deoxycholic acid, glutamic acid, glucuronic acid, boronic acid, a sulfinic acid, a sulfamic acid, or mixtures of any two or more thereof. It is to be noted that when formic acid is included as the acid, formic acid may also be a hydrogen source. In some embodiments, the process further includes isolating the compound of formula I. In some embodiments, the process includes preparing a pharmaceutically acceptable salt of the compound of formula I.

In any of the above embodiments, it may be that the combination of the compound of formula VIII, the hydrogen source, and the transition metal catalyst is subjected to a temperature from about −20° C. to about 150° C. Such an embodiment may be performed at about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., and any range including and between any two of these values.

In some embodiments, the compound of formula IV is prepared by a process that includes combining a compound of formula IX:

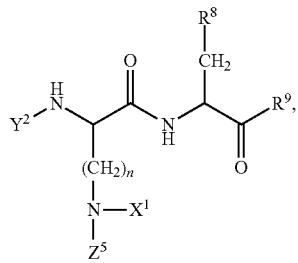

and a cleaving acid described herein to produce the compound of formula IV, wherein $Y^2$ is an amino protecting group susceptible to acid-mediated removal. While cleaving acids have been previously described herein, the cleaving acid for preparing a compound of formula IV may or may not include the cleaving acid(s) utilized in other processes described herein. In some embodiments, $Y^2$ is tert-butyloxycarbonyl (Boc). In any of the above embodiments, it may be that $R^9$ is $NH_2$. In any of the above embodiments, it may be that the process further includes isolating the compound of formula IV.

In any of the above embodiments, it may be that the compound of formula IX is prepared by a process that includes combining a compound of formula X

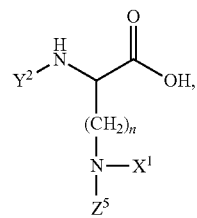

a compound of formula XI

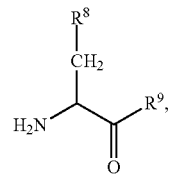

and a coupling agent to produce a compound of formula IX. While coupling agents have been previously described herein, the coupling agent utilized to produce the compound of formula IX may or may not include the coupling agent(s) and combinations utilized in other processes described herein. In some embodiments, $Y^2$ is tert-butyloxycarbonyl (Boc). In some embodiments, $R^9$ is $NH_2$. In some embodiments, the process further includes isolating the compound of formula IX. In any of the above embodiments, it may be that $X^1$ at each occurrence is independently hydrogen, allyloxycarbonyl, benzyloxycarbonyl (Cbz), or 2-chlorobenzyloxycarbonyl; $X^2$ at each occurrence is independently hydrogen, allyloxycarbonyl, benzyloxycarbonyl (Cbz), or 2-chlorobenzyloxycarbonyl; and $X^4$ at each occurrence is independently hydrogen, nitro, allyloxycarbonyl, benzyloxycarbonyl (Cbz), or 2-chlorobenzyloxycarbonyl.

In another aspect, a process for preparing a compound of formula III is provided. The process for preparing a compound of formula III includes combining a compound of formula XII

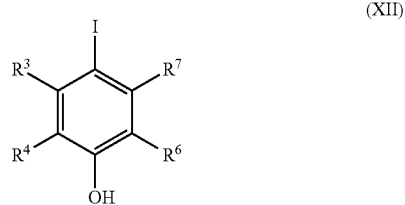

with a compound of formula XIII or a salt thereof (e.g., the HCl salt)

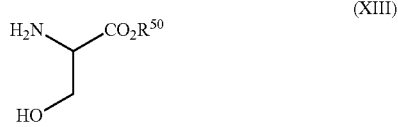

under conditions to form a compound of formula XIV

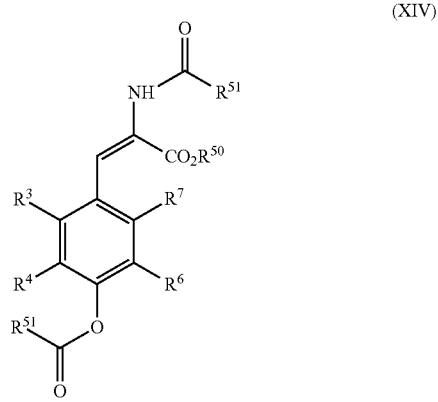

wherein $R^{50}$ and $R^{51}$ are each independently hydrogen or a substituted or unsubstituted $C_1$-$C_6$ alkyl, aryl, or cycloalkyl group. In some embodiments, $R^4$ and $R^6$ are each hydrogen. In some embodiments, $R^3$, $R^7$, $R^{50}$ and $R^{51}$ are each methyl. In some embodiments, the process further includes isolating the compound of formula XIV.

In some embodiments, the conditions to form the compound of formula XIV include a one-pot synthesis. One-pot synthesis refers to a process wherein a series of successive chemical reactions are performed in one reaction container without isolating intermediate product(s) formed in the series of reactions before the last reaction. In some embodiments, the conditions to form the compound of formula XIV include a one-pot synthesis that includes (1) combining the compound of formula XII and the compound of formula XIII with $(R^{51}CO)_2O$ (such as acetic anhydride), and an organic base (such as triethylamine ($Et_3N$), diisopropylethylamine (DIPEA), pyridine and 4-dimethylaminopyridine (DMAP)) to form a mixture, and (2) adding a transition metal source and $PR^{52}_3$ to the mixture of (1), wherein each $R^{52}$ is independently $C_1$-$C_6$ alkyl, unsubstituted phenyl, or phenyl substituted with 1 to 5 $C_1$-$C_6$ alkyl groups. In some embodiments, the one-pot synthesis includes an appropriate solvent. Appropriate solvents herein include solvents which dissolve or suspend one or more reactants, permitting the reaction to take place. Such solvents include, but are not limited to, methylene chloride ($CH_2Cl_2$), chloroform ($CHCl_3$), tetrahydrofuran (THF), 2-methyltetrahydrofuran, dimethoxyethane (DME), dioxane or mixtures of any two or more thereof. In some embodiments, $PR^{52}_3$ is tritolylphosphine ($P(tolyl)_3$). The transition metal source includes a transition metal and may or may not include other elements or compounds. In some embodiments, the transition metal source is a Pd compound, such as $Pd(OAc)_2$.

In some embodiments, the conditions to form the compound of formula XIV include a temperature of no more than about 60° C. In some embodiments, the temperature is from about 0° C. to about 60° C. The temperature may be about 0° C., about 5° C., about 10° C., about 15° C., about 20° C., about 25° C., about 30° C., about 35° C., about 40° C., about 45° C., about 50° C., about 55° C., about 60° C., or any range including and between any two such values or below any one of these values. In some embodiments, the temperature is from about 50° C. to about 60° C. In some embodiments, the temperature is about 55° C.

It is surprising that the compound of formula XIV can be prepared from the compound of formula XII and compound of formula XIII in one pot as such a preparation includes three conversion steps. It is further surprising that the three conversion steps can be accomplished in a one-pot reaction to provide the compound of formula XIV with a high yield. In some embodiments, the yield is at least about 50%, or at least about 60%, or at least about 70%, or at least about 75%, or at least about 80%. In some embodiments, the compound of formula XIV is isolated in a purity of at least about 90%, or at least about 95%, or at least about 98%, or at least about 99%. In some embodiments, the compound of formula XIV is isolated (a) in a purity of at least about 90%, or at least about 95%, or at least about 98%, or at least about 99%, and (b) in a yield of at least about 50%, or at least about 60%, or at least about 70%, or at least about 75%, or at least about 80%.

In an alternative aspect, it may be that forming the compound of formula XIV involves combining a compound of formula A

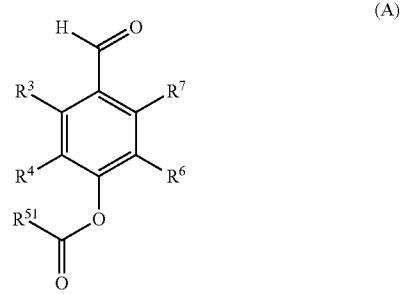

with a compound of formula B or a salt thereof

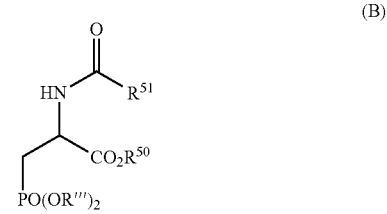

under conditions to form the compound of formula XIV, where R'" at each occurrence is independently a substituted or unsubstituted alkyl, alkenyl, cycloalkyl, cycloalkylalkyl, aryl, aralkyl, heteroaryl, heteroarylalkyl, heterocyclyl, or heterocyclylalkyl group.

In any of the above embodiments, it may be that the conditions to form the compound of formula XIV involve a one pot synthesis. In any of the above embodiments, it may be that the one-pot synthesis involves combining the compound of formula A with the compound of formula B or salt thereof and further combining an base. The base may include any one or more of the previously described organic or inorganic bases. In any of the above embodiments, the base may include an organic base. In any of the above embodiments, it may be that the organic base is triethylamine ($Et_3N$), 1,8-diazabicyclo[5.4.0]undec-7-ene (DBU), diisopropylethylamine (DIPEA), pyridine, 4-dimethylaminopyridine (DMAP), or a combination of any two or more thereof. In any of the above embodiments, it may be that the organic base is DBU or DIPEA. In any of the above embodiments, it may be that R'" is methyl. In any of the above embodiments of formula B, it may be that $R^{51}$ is methyl. In any of the above embodiments, it may be that $R^3$, $R^7$, $R^{50}$ and $R^{51}$ are each methyl and $R^4$ and $R^6$ are each hydrogen. In any of the above embodiments, it may be that combining the compound of formula A with the compound of formula B or salt thereof further involves a suitable solvent. Such solvents include, but are not limited to, alcohols (e.g., methanol ($CH_3OH$), ethanol (EtOH), isopropanol (iPrOH), trifluorethanol (TFE), butanol (BuOH)), halogenated sovlents (e.g., methylene chloride ($CH_2Cl_2$), chloroform ($CHCl_3$), benzotrifluoride (BTF; $PhCF_3$)), ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), amides (e.g., dimethylformamide (DMF), dimethylacetamide (DMA)), nitriles (e.g., acetonitrile ($CH_3CN$), proprionitrile ($CH_3CH_2CN$), benzonitrile (PhCN)), sulfoxides (e.g., dimethyl sulfoxide), sulfones (e.g., sulfolane), water, or mixtures of any two or more thereof. In any of the above embodiments, it may be that the solvent includes $CH_3OH$, EtOH, iPrOH, TFE, BuOH, $CH_2Cl_2$, $CHCl_3$, $PhCF_3$, THF, 2Me-THF, DME, dioxane, ethyl acetate, isopropyl acetate, acetone, methylethyl ketone, methyl isobutyl ketone, DMF, DMA, $CH_3CN$, $CH_3CH_2CN$, PhCN, dimethylsulfoxide, sulfolane, water, or mixtures of any two or more thereof.

In any of the above embodiments, it may be that combining the compound of formula A with the compound of formula B or salt thereof involves a temperature from about −40° C. to about 150° C. Such an embodiment may be performed at about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., and any range including and between any two of these values.

In any of the above embodiments, it may be that the compound of formula XIV is a compound of formula XIV-A:

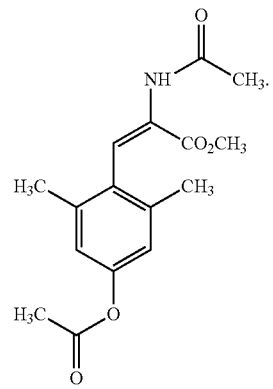

(XIV-A)

In some embodiments, the process of preparing a compound of formula III further includes converting the compound of formula XIV to a compound of formula XV:

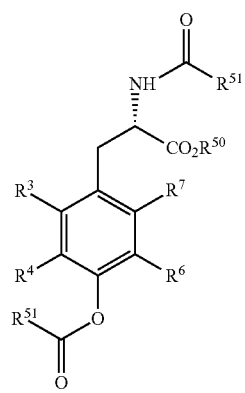

(XIV)

In some embodiments, the compound of formula XIV is converted to the compound of formula XV under conditions comprising a hydrogen source, such as hydrogen gas ($H_2$), diimide, formic acid, formate salts, cyclohexene, or cyclohexadiene, a transition metal source, a chiral ligand and an appropriate solvent. Such solvents include, but are not limited to, alcohols (e.g., methanol ($CH_3OH$), ethanol (EtOH), isopropanol (iPrOH), trifluorethanol (TFE), butanol (BuOH)), halogenated sovlents (e.g., methylene chloride ($CH_2Cl_2$), chloroform ($CHCl_3$), benzotrifluoride (BTF; $PhCF_3$)), ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), amides (e.g., dimethylformamide (DMF), dimethylacetamide (DMA)), nitriles (e.g., acetonitrile ($CH_3CN$), proprionitrile ($CH_3CH_2CN$), benzonitrile (PhCN)), sulfoxides (e.g., dimethyl sulfoxide), sulfones (e.g., sulfolane), water, or mixtures of any two or more thereof. In any of the above embodiments, it may be the solvent includes $CH_3OH$, EtOH, iPrOH, TFE, BuOH, $CH_2Cl_2$, $CHCl_3$, $PhCF_3$, THF, 2Me-THF, DME, dioxane, ethyl acetate, isopropyl acetate, acetone, methylethyl ketone, methyl isobutyl ketone, DMF, DMA, $CH_3CN$, $CH_3CH_2CN$, PhCN, dimethylsulfoxide, sulfolane, water, or mixtures of any two or more thereof. The transition metal source includes a transition metal and may or may not include other elements or compounds. Transition metals include, but are not limited to, cobalt (Co), iridium (Ir), molybdenum (Mo), nickel (Ni), platinum (Pt), palladium (Pd), rhodium (Rh), ruthenium (Ru), tungsten (W), or a combination of any two or more thereof. In some embodiments, the transition metal is Rh. In some embodiments, the transition metal source is Rh(I)(COD)$_2$BF$_4$. In some embodiments, the chiral ligand is a chiral organo ferrocenyl compound, such as (S)-MeBoPhos. In some embodiments, the compound of formula XIV is converted to a compound of formula XV under conditions that include H$_2$, Rh(I)(COD)$_2$BF$_4$, (S)-MeBoPhos and THF.

In some embodiments, the yield of converting the compound of formula XIV to the compound of formula XV is at least about 50%, or at least about 60%, or at least about 70%, or at least about 80%, or at least about 90%, or at least about 95%. In some embodiments, the compound of formula XV is isolated in a purity of at least about 90%, or at least about 95%, or at least about 98%, or least about 99% in a yield of at least about 50%, or at least about 60% or at least about 70%, or at least about 80%, or at least about 90%, or at least about 95%. In some embodiments, the process further includes isolating the compound of formula XV.

The process provides the compound of formula XV with a high enantioselectivity over its corresponding isomer at the stereocenter illustrated. In some embodiments, the compound of formula XV is provided in a % enantiomeric excess (% ee) of at least 50%, or at least about 60%, or at least about 70%, or at least about 80%, or at least about 90%, or at least about 95%, or at least about 99%. In some embodiments, the compound of formula XV is isolated in a purity of at least about 90%, or at least about 95%, or at least about 98%, or least about 99% in a yield of at least about 50%, or at least about 60% or at least about 70%, or at least about 80%, or at least about 90%, or at least about 95%.

In some embodiments, the compound of formula XV is a compound of formula XV-A:

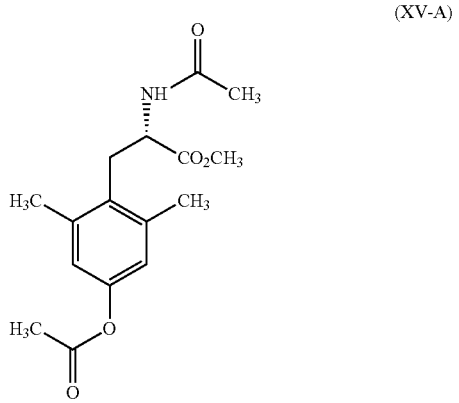 [SMILES: COC(=O)[C@H](Cc1c(C)cc(OC(C)=O)cc1C)NC(C)=O]

(XV-A)

In some embodiments, the process of preparing a compound of formula III further includes converting the compound of formula XV to a compound of formula III. In some embodiments, the compound of formula XV is converted to the compound of formula III under conditions including (1) combining the compound of formula XV with Y$^1$-Lv, an organic base, and an appropriate solvent, wherein Lv is a leaving group such as halo, —O—Y', or —O—C(O)Cl, and (2) ester hydrolysis conditions. In some embodiments, Y$^1$ is Boc and Y$^1$-Lv is Boc$_2$O. In some embodiments, the base is triethylamine (Et$_3$N), 1,8-diazabicyclo[5.4.0]undec-7-ene (DBU), diisopropylethylamine (DIPEA), pyridine or 4-dimethylaminopyridine (DMAP), or a combination of any two or more thereof. In some embodiments, the base is DMAP. The solvent may include an alcohol, a halogenated solvent, an ether, an ester, a ketone, an amide, a nitrile, a sulfoxide, a sulfone, water, or mixtures of any two or more thereof. In any of the above embodiments, it may be that the solvent includes CH$_3$OH, EtOH, iPrOH, TFE, BuOH, CH$_2$Cl$_2$, CHCl$_3$, PhCF$_3$, THF, 2Me-THF, DME, dioxane, ethyl acetate, isopropyl acetate, acetone, methylethyl ketone, methyl isobutyl ketone, DMF, DMA, CH$_3$CN, CH$_3$CH$_2$CN, PhCN, dimethylsulfoxide, sulfolane, water, or mixtures of any two or more thereof. In some embodiments, the solvent is methylene chloride (CH$_2$Cl$_2$), chloroform (CHCl$_3$), tetrahydrofuran (THF), 2-methyltetrahydrofuran, dimethoxyethane (DME), dioxane or a mixture of any two or more thereof. In some embodiments, the solvent is methylene chloride. Ester hydrolysis conditions are conditions under which an ester is hydrolyzed to a carboxylic acid and an alcohol. Such conditions are generally known in the art. In some embodiments, the ester hydrolysis conditions include an aqueous solution of an alkali metal hydroxide (e.g., LiOH, NaOH or KOH) or an alkaline earth metal hydroxide (e.g., Ca(OH)$_2$ or Mg(OH)$_2$). In some embodiments, the ester hydrolysis conditions include an aqueous solution of NaOH. In some embodiments, the process further includes isolating the compound of formula III.

In some embodiments, the yield of converting the compound of formula XV to the compound of formula III is at least about 50%, or at least about 60%, or at least about 70%, or at least about 80%, or at least about 90%, or at least about 95%. In some embodiments, the compound of formula III is isolated in a purity of at least about 90%, or at least about 95%, or at least about 97%, or at least about 99% in a yield of at least about 50%, or at least about 60% or at least about 70%, or at least about 80%, or at least about 90%, or at least about 95%.

In some embodiments, the compound of formula III is a compound of formula III-A.

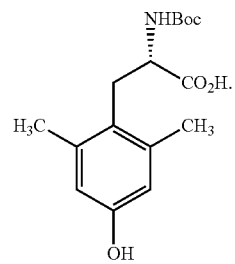

(III-A)

In another aspect that may be present in any of the aspects and embodiments described herein, the preparation of a peptide by use of the compound of formula III where R$^5$ is hydrogen is provided. The compound of formula III where R$^5$ is hydrogen is shown below as formula XVI.

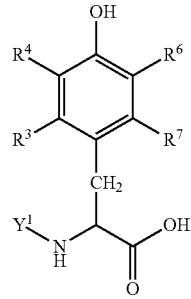

(XVI)

It is surprising that such a compound can be incorporated in a peptide without protecting the hydroxyl group on the phenol. In some embodiments, the use of the compound of formula XVI includes coupling the compound of formula XVI with an amino compound to form a coupling product having an amide bond. In some embodiments, the amino compound is an amino acid derivative wherein the acid group is protected with an appropriate protecting group. Such acid protecting groups are generally known in the art, such as those described in T. W. Greene and P. G. M. Wuts, Protecting Groups in Organic Synthesis, Third Edition, Wiley, New York, 1999. Non-limiting examples of acid protecting groups include alkyl ester such as methyl ester, ethyl ester or t-butyl ester, or a benzyl ester. In some embodiments, the amino acid is a peptide having a free amino terminus. In some embodiments, the compound of formula XVI is used in the preparation of the compound of formula I or any one of the compounds of formulas IV, V, VI, or VIII as described herein.

EXAMPLES

The present technology is further illustrated by the following examples, which should not be construed as limiting in any way. For each of the examples below, any aromatic-cationic peptide described herein could be used. By way of example, but not by limitation, the aromatic-cationic peptide used in the example below could be 2'6'-Dmt-D-Arg-Phe-Lys-NH$_2$, Phe-D-Arg-Phe-Lys-NH$_2$, or D-Arg-2'6'-Dmt-Lys-Phe-NH$_2$. In one embodiment, the aromatic-cationic peptide is a pharmaceutical salt for example, but not limited to, e.g., a tartrate salt, acetate salt, or trifluoroacetate salt.

Terms and abbreviations:
ACN=acetonitrile,
Atm=atmosphere,
BOC=Boc=tert-butoxycarbonyl,
BOP reagent=Benzotriazol-1-yloxytris(dimethylamino)phosphonium hexafluorophosphate,
Bn=benzyl,
br=broad,
t-BuOH=tert-butyl alcohol,
Cat.=catalytic,
Conc.=conc=concentrated,
d=doublet,
dd=doublet of doublets,
ddd=doublet of doublet of doublets,
dt=doublet of triplets,
DCM=dichloromethane (CH$_2$Cl$_2$),
Dess-Martin periodinane=1,1,1-Tris(acetyloxy)-1,1-dihydro-1,2-benziodoxol-3-(1H)-one
DIAD=diisopropyl azodicarboxylate,
DIPEA=N,N-diisopropylethylamine,
DMF=N,N-dimethylforamide,
DMSO=dimethyl sulfoxide,
EDC=N-ethyl-N'-(3-dimethylaminopropyl)carbodiimide hydrochloride
Et$_2$O=diethyl ether,
Et$_3$N=triethylamine,
EtOAc=ethyl acetate,
EtOH=ethyl alcohol,
equiv.=equivalent(s),
h=hour(s),
HATU=N,N,N',N'-tetramethyl-O-(7-azabenzotriazol-1-yl)uronium hexafluorophosphate
H$_2$O=water,
HCl=hydrochloric acid
HPLC=high performance liquid chromatography,
HOAc=acetic acid,
HOBt=1-hydroxybenzotriazole
IPA=isopropyl alcohol,
ISCO=normal phase silica gel cartridges supplied by Teledyne ISCO,
K$_2$CO$_3$=potassium carbonate,
LiBH$_4$=lithium tetrahydroborate,
LiBr=lithium bromide,
LiCl=lithium chloride,
LAH=lithium tetrahydroaluminate,
m=multiplet,
min.=min=minute(s)
MgCl$_2$=magnesium chloride
MeOH=methanol,
2-MeTHF=2-methyltetrahydrofuran,
MsCl=methanesulfonyl chloride,
MTBE=methyl tert-butyl ether,
NaHCO$_3$=sodium bicarbonate,
Na$_2$SO$_4$=sodium sulfate,
NH$_4$OH=ammonium hydroxide,
NH$_4$OAc=ammonium acetate,
NH$_4$Cl=ammonium chloride,
NMR=nuclear magnetic resonance,
NMP=N-methylpyrrolidinone,
Pd—C=palladium on activated carbon
p=pentet,
PMB=p-methoxybenzyl,
PMBCl=p-methoxybenzyl chloride,
ret=retention
rt=room temperature,
s=singlet,
sat=saturated,
t=triplet,
TFA=trifluoroacetic acid,
TBDPS=t-butyldiphenylsilyl,
TBS=t-butyldimethylsilyl,
THF=tetrahydrofuran,
TLC=thin layer chromatography Example 1

Preparation of Boc-DMT-OH in 100 g Scale

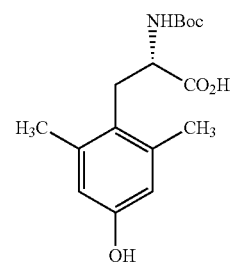

Boc-DMT-OH was prepared according to Scheme I:

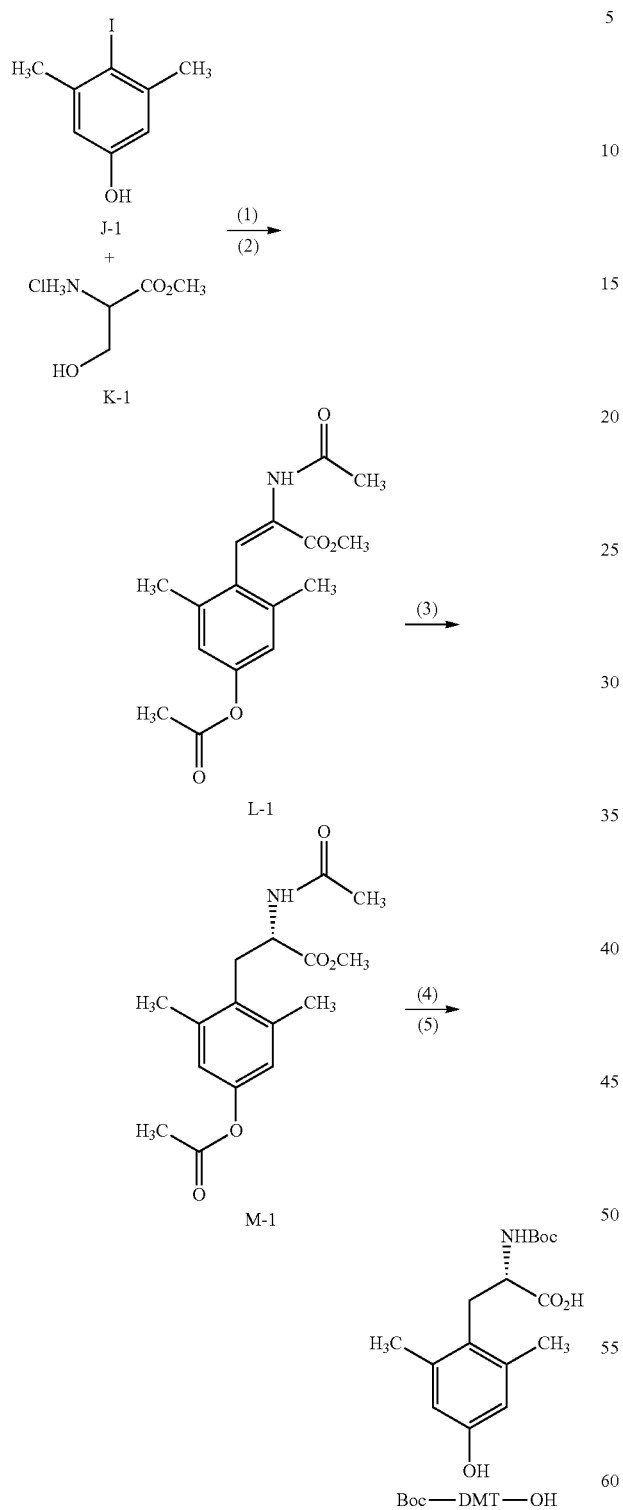

The following reagents were used in the steps of Scheme I:

Step (1): acetic anhydride (Ac$_2$O), triethylamine (NEt$_3$), and acetonitrile (ACN);

Step (2): palladium(II) acetate (Pd(OAc)$_2$), tri(o-tolyl)phosphine (P(tolyl)$_3$), and triethylamine (NEt$_3$);

Step (3): bis(cycloocta-1,5-diene)rhodium(I) tetrafluoroborate (Rh(I)(COD)$_2$BF$_4$), 1-(S)—N-methyl-N-(diphenylphosphino)-1-[(R)-(diphenylphosphino)-ferrocenyl]ethylamine (S-MeBoPhos), H$_2$, and tetrahydrofuran (THF);

Step (4): Boc anhydride (Boc$_2$O), 4-dimethylaminopyridine (DMAP), and dichloromethane (CH$_2$Cl$_2$); and Step (5): aqueous sodium hydroxide (NaOH).

The process described in Scheme I provides several advantages.

Steps (1) and (2) were accomplished in a one pot synthesis including three conversion steps and provided compound L-1 with a high HPLC purity of 99.2% and isolated yield (after precipitation) of 74%. One side product detected through stability experiments, by prolonged heating at over 60° C. (ca 4% after 12 hours, not identified) can be prevented by keeping reaction temperature at 55° C.

Step (3) provided compound M-1 in a high HPLC purity of 99.2%, a high % ee of 99.6% by analytical chiral HPLC, and an isolated yield of 95%. Compound M-1 can be provided without color by including a filtration step through neutral Alox.

Step (4) was accomplished with retention of chiral purity in small scale stress experiments. Purity before precipitation is 97.6%. Ca. An impurity which is the corresponding N-acetyl product due to incomplete bocylation has been detected at 0.8%.

No protecting group is needed on the phenol OH for the coupling reactions.

Example 2

Liquid Phase Peptide Synthesis on a 1 g Scale

Tetrapeptide (D)Arg-DMT-Lys-Phe-NH$_2$ can be prepared according to Scheme II:

Scheme II
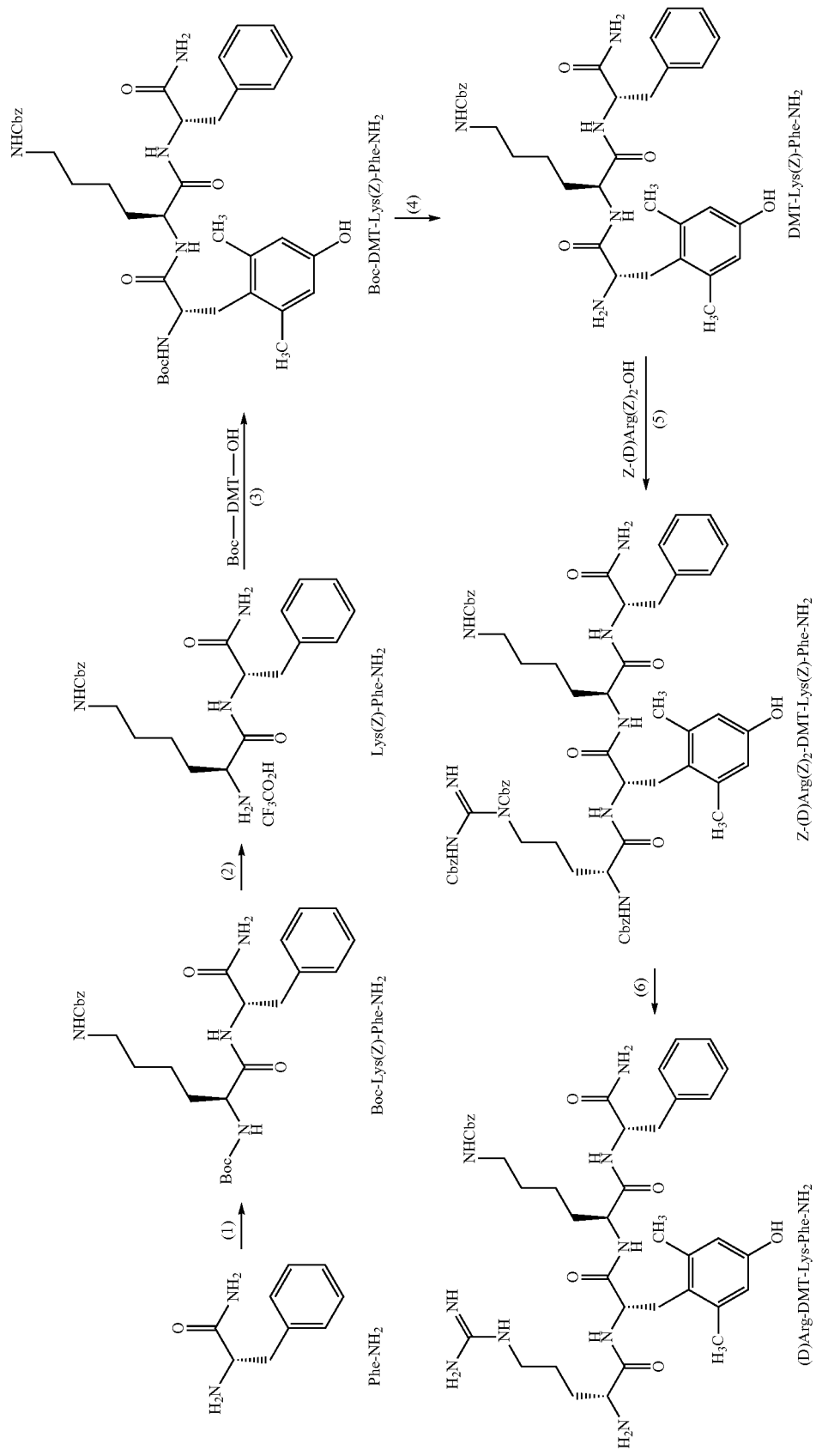

In the above scheme: (1) EDC, HOBT, DMF, (2) TFA, CH$_2$Cl$_2$, (3) EDC, HOBT, DMF, (4) TFA, CH$_2$Cl$_2$, (5) EDC, HOBT, DMF, (6) H$_2$, 5% Pd/C, HOAc, CH$_3$OH. No benzyl protecting group at the phenol OH group of the DMT building block was needed. The tetramer before deprotection was formed in 76% isolated yield as a solid in 90% HPLC purity with one impurity present in 7%.

Example 3

Further Routes to D-arginyl-2,6-dimethyl-L-tyrosyl-L-lysyl-L-phenylalaninamide

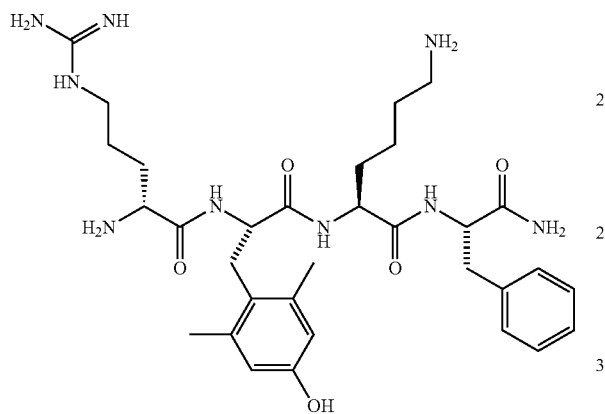

For the routes described below, temperatures are given in degrees Celsius (° C.). Unless otherwise stated, operations are carried out at room or ambient temperature, that is, at a temperature in the range of 18-25° C. under an inert atmosphere with the exclusion of moisture. Chromatography means flash chromatography on silica gel as described in Still, W. C, Kahn, M.; Mitra, A. *J. Org. Chem.* 1978, 43, 2923; thin layer chromatography (TLC) is carried out on silica gel plates. NMR data is given in parts per million (ppm) relative to the deuterium lock signal of the deuterated solvent utilized. Conventional abbreviations for signal shape are used. No distinction is made between a multiplet arising from a complex pattern for a single proton or a multiplet arising from the overlap of multiple protons or spin systems. For mass spectra (MS), the lowest mass major ion is reported for molecules where isotope splitting results in multiple mass spectral peaks. Solvent mixture compositions are given as volume percentages or volume ratios.

Analytical HPLC: Agilent 1100 HPLC, Zorbax Eclipse XDB-C18 50×4.6 mm column, column temperature of 30° C., 1.5 mL/min, Solvent A—Water (0.1% TFA), Solvent B—Acetonitrile (0.07% TFA), Gradient: 6 min 95% A to 90% B; 1 min. hold; then recycle (to 95% A over 1 min), UV Detection @ 210 and 254 nm.

All isolated products were ≥95% purity by HPLC unless otherwise specified.

Route 1A

Step 1. Preparation of N$^6$-{[(benzyl)oxy]carbonyl}-L-lysyl-L-phenylalaninamide

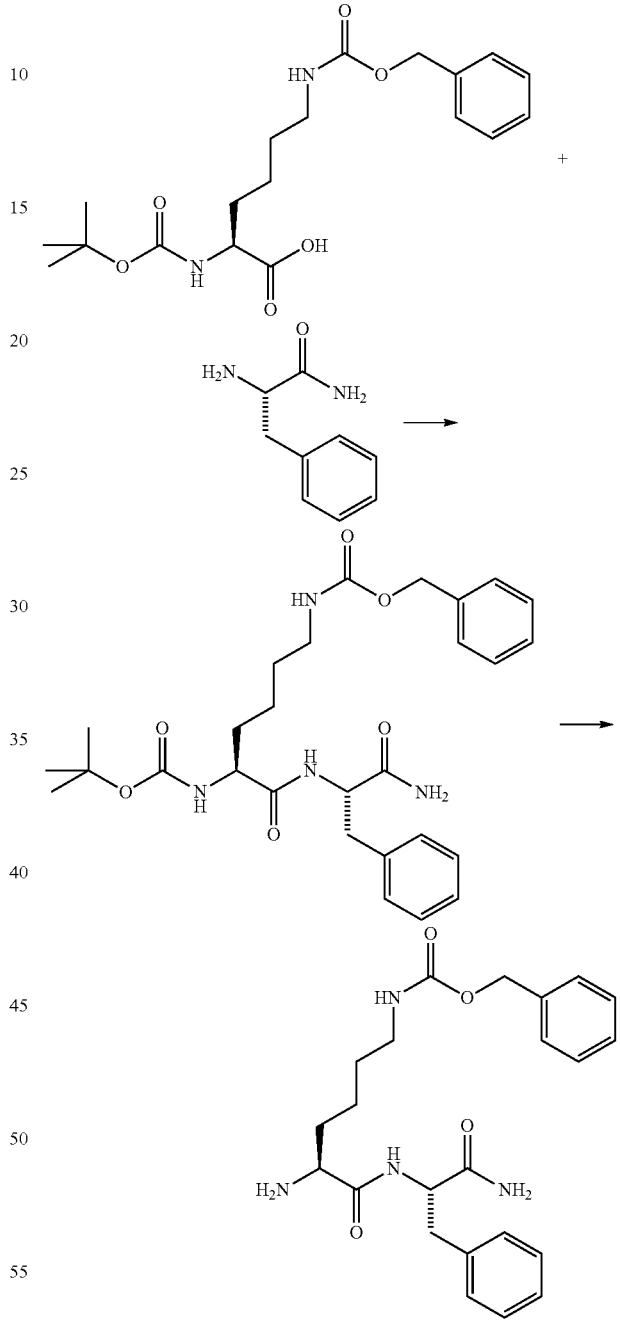

To a mixture of L-phenylalaninamide (0.640 g, 3.90 mmol), N$^6$-[(benzyloxy)carbonyl]-N$^2$-(tert-butoxycarbonyl)-L-lysine (1.810 g, 4.76 mmol) and HOBt monohydrate (0.913 g, 5.96 mmol) in DCM (20 mL) was added EDC (1.130 g, 5.88 mmol). After 90 min, aqueous Na$_2$CO$_3$ (10% w/w, 2.5 ml) was added and the mixture stirred at 37° C. for 10 min. The layers were separated and the organic layer washed with water (9.75 mL). The organic layer was separated and methanesulfonic acid (1.00 mL, 15.5 mmol) added. After 4 h, aqueous Na$_2$CO$_3$ (10% w/w, 17.55 ml) was added and the mixture stirred for 10 min. Concentration under reduced pressure afforded a solid that was isolated by filtration, washed with water (2×10 mL), and dried in vacuo to afford the title compound (1.43 g, 86%) as a white amorphous solid. $^1$H NMR (400 MHz, DMSO-d$_6$) δ 1.07-1.43 (m, 6 H), 1.56-1.90 (v br m, 2 H), 2.82 (dd, J=13, 9 Hz, 1 H), 2.92 (q, J=7 Hz, 2 H), 2.97-3.10 (m, 2 H), 4.43-4.50 (m, 1 H), 5.00 (s, 2 H), 7.08-7.28 (m, 7 H), 7.28-7.41 (m, 5 H), 7.46 (br s, 1 H), 7.96 (br d, J=8 Hz, 1 H); MS (ESI+) for C$_{23}$H$_{30}$N$_4$O$_4$ m/z 427.1 (M+H)$^+$; HPLC retention time=2.92 min.

Step 2. Preparation of N$^2$-[(benzyloxy)carbonyl]-N$^5$-[{[(benzyloxy)carbonyl]amino}{[(benzyloxy)carbonyl]imino}methyl]-D-ornithyl-2,6-dimethyl-L-tyrosyl-N$^6$-{[(benzyl)oxy]carbonyl}-L-lysyl-L-phenylalaninamide

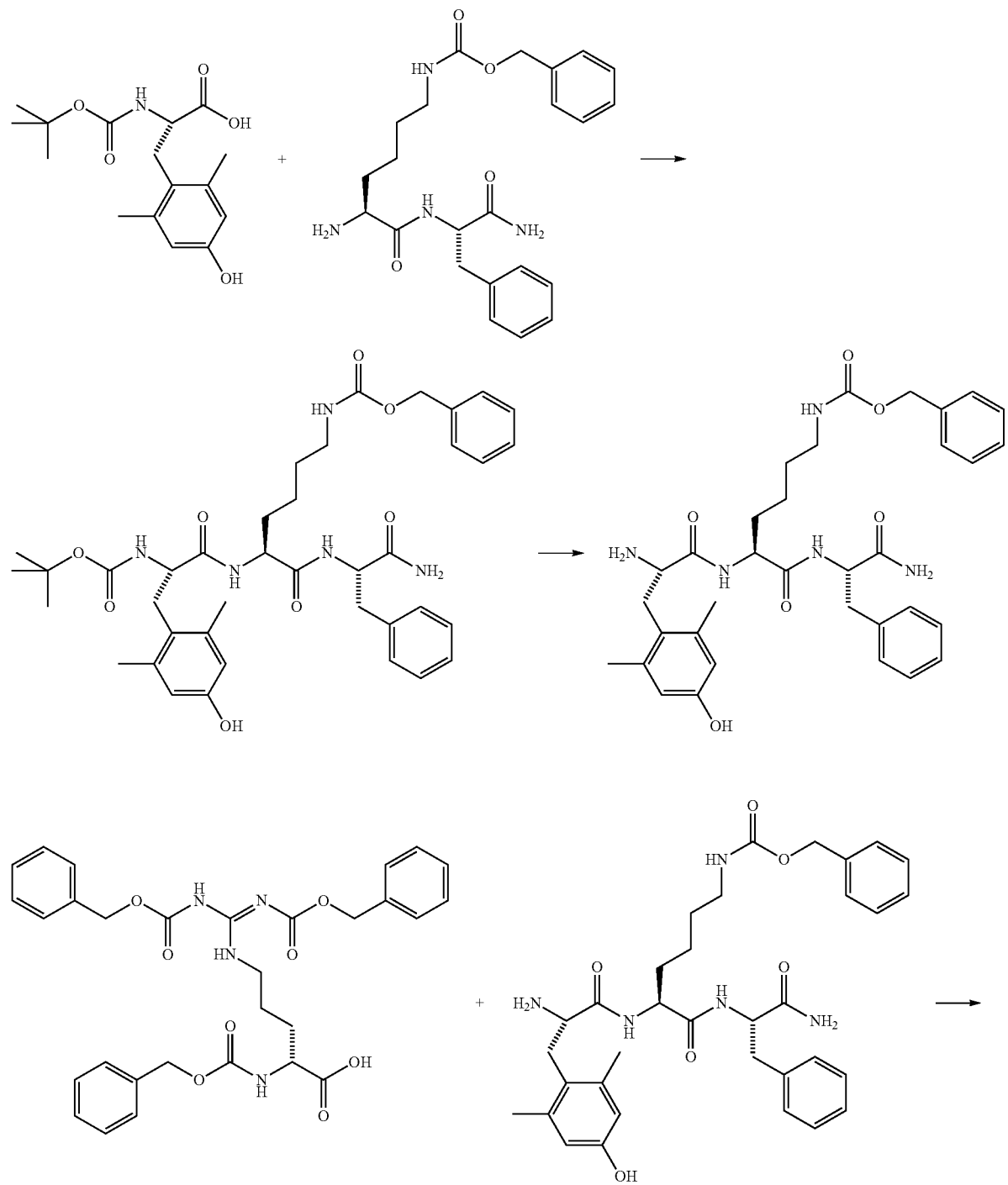

-continued

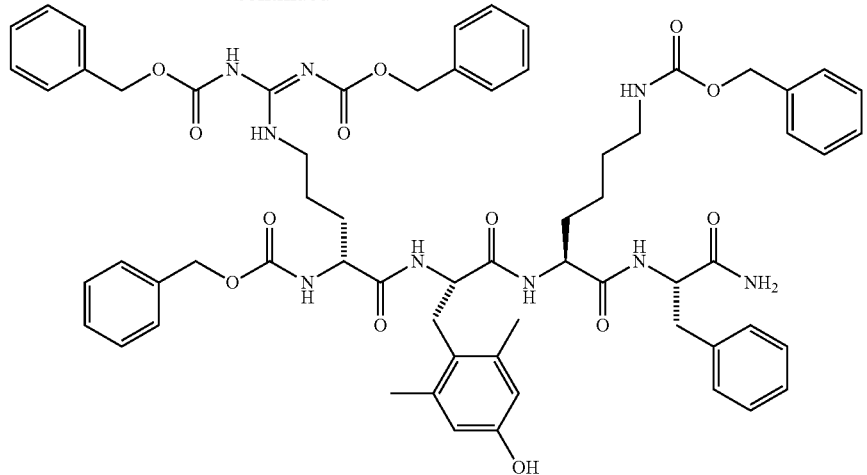

To a mixture of N-(tert-butoxycarbonyl)-2,6-dimethyl-L-tyrosine (0.400 g, 1.29 mmol), $N^6$-[(benzyloxy)carbonyl]-L-lysyl-L-phenylalaninamide (0.552 g, 1.29 mmol) and HOBt monohydrate (0.238 g, 1.55 mmol) in THF/2-MeTHF (1:1, 13 mL) was added EDC (0.297 g, 1.55 mmol). After 4 h, aqueous $KHSO_4$ (5% w/w, 1.6 mL) was added and the resulting mixture stirred for 3 h. The layers were separated and the organic layer washed with aqueous $Na_2CO_3$ (1.6 mL) and water (1.6 mL) then concentrated. The residue was dissolved in THF (6.5 mL) and methanesulfonic acid (0.671 mL, 10.34 mmol) added. After 16 h, triethylamine (1.530 mL, 10.99 mmol) was added followed by HOBt monohydrate (0.240 g, 1.56 mmol), $N^2$-[(benzyloxy)carbonyl]-$N^5$-[{[(benzyloxy)carbonyl]amino}{[(benzyloxy)carbonyl]imino}methyl]-D-ornithine (0.746 g, 1.29 mmol) and EDC (0.300 g, 1.56 mmol). After 2.5 h, aqueous $Na_2CO_3$ (5% w/w, 12.9 ml) was added and mixture stirred for 20 min. The solids were isolated by filtration, washed with water (2×10 mL) and dried (50° C. in vacuo) to provide 1.420 g of a solid (HPLC purity of 66 area % at 210 nm). Purification of 0.900 g of the solid by flash chromatography (1-3% methanol in DCM) afforded the title compound (0.560 g, adjusted yield of 58%) as a white amorphous solid. $^1$H NMR (400 MHz, DMSO-$d_6$) δ 1.11-1.62 (m, 10 H), 2.12 (s, 6 H), 2.62-2.71 (m, 1 H), 2.76-3.06 (m, 5 H), 3.75-3.85 (m, 2 H), 3.92-4.00 (m, 1 H), 4.09-4.18 (m, 1H), 4.33-4.43 (m, 1 H), 4.46-4.55 (m, 1 H), 4.89-5.08 (m, 6 H), 5.21 (s, 2 H), 6.30 (s, 2 H), 7.05-7.43 (m, 29 H), 7.75 (br d, J=8 Hz, 1 H), 7.89 (br d, J=7 Hz, 1 H), 8.10 (br d, J=8 Hz, 1 H), 8.85 (s, 1 H), 9.17 (v br m, 2 H); MS (ESI+) for $C_{64}H_{73}N_9O_{13}$ m/z 1176.6 (M+H)$^+$; HPLC retention time=4.90 min.

Step 3. Preparation of D-arginyl-2,6-dimethyl-L-tyrosyl-L-lysyl-L-phenylalaninamide

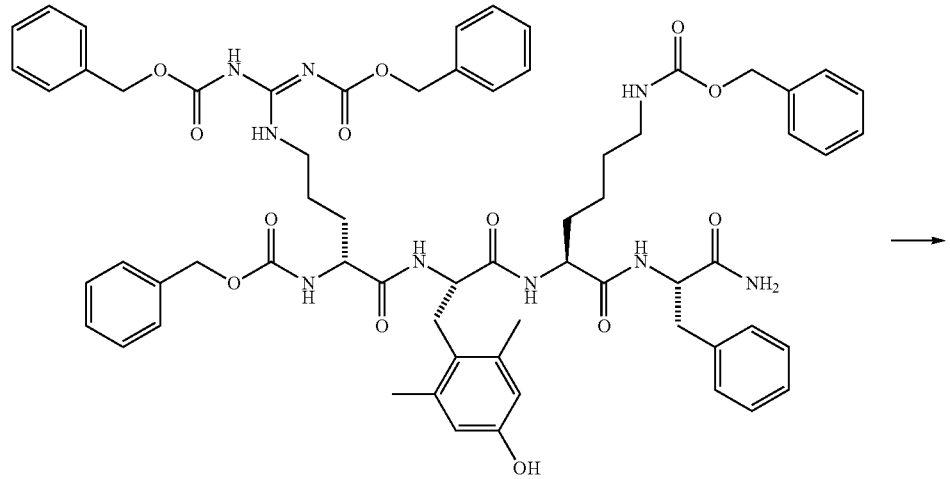

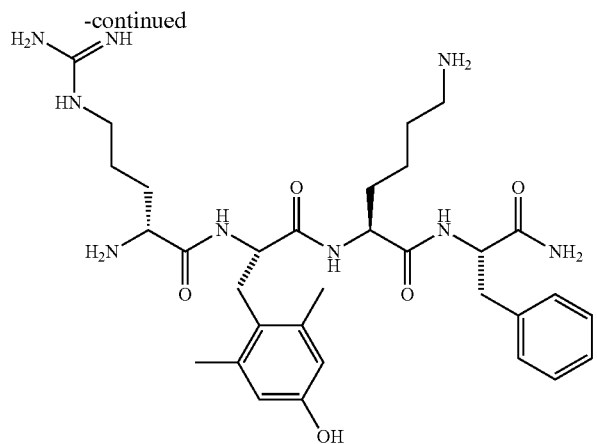

To a flask containing palladium (10 wt % on carbon powder, dry (Aldrich 520888), 0.020 g) and $N^2$-[(benzyloxy)carbonyl]-$N^5$-[{[(benzyloxy)carbonyl]amino}{[(benzyloxy)carbonyl]imino}methyl]-D-ornithyl-2,6-dimethyl-L-tyrosyl-$N^6$-{[(benzyl)oxy]carbonyl}-L-lysyl-L-phenylalaninamide (0.200 g, 0.17 mmol) was added methanol (9 mL) and acetic acid (0.039 ml, 0.68 mmol). The flask was subjected to 2 cycles of evacuation—hydrogen gas backfill and the mixture stirred under 1 atm of $H_2$ at 50° C. for 4 h. The mixture was cooled, filtered through Solka-Floc, and washed with additional methanol (25 mL). The combined washes were concentrated under reduced pressure and the residue lyophilized from water (20 mL) to afford the title compound (0.132 g, 95%) as a white amorphous powder. The compound was found to contain 22% w/w of acetate as determined by integration of the $^1$H NMR spectra. $^1$H NMR (400 MHz, $D_2O$) δ 1.05-1.28 (m, 4 H), 1.43-1.63 (m, 6 H), 1.79 (s, 8.8H, acetate), 2.09 (s, 6 H), 2.71-3.08 (m, 8H), 3.81 (t, J=6 Hz, 1 H), 4.16 (t, J=7 Hz, 1 H), 4.43 (t, J=7 Hz, 1 H), 4.59 (t, J=8 Hz, 1H), 6.43 (s, 2 H), 7.13-7.29 (m, 5 H); MS (ESI+) for $C_{32}H_{49}N_9O_5$ m/z 640.5 (M+H)$^+$; HPLC retention time=2.26 min.

Route 1B

Step 1. Preparation of $N^6$-[(benzyloxy)carbonyl]-$N^2$-(tert-butoxycarbonyl)-L-lysyl-L-phenylalaninamide

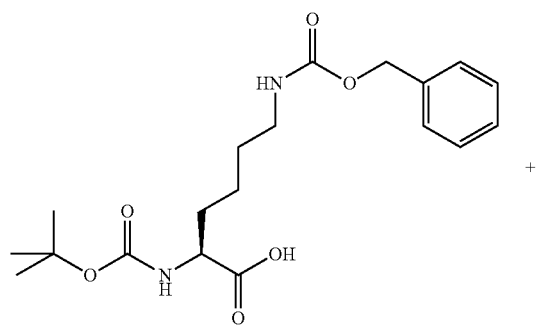

+

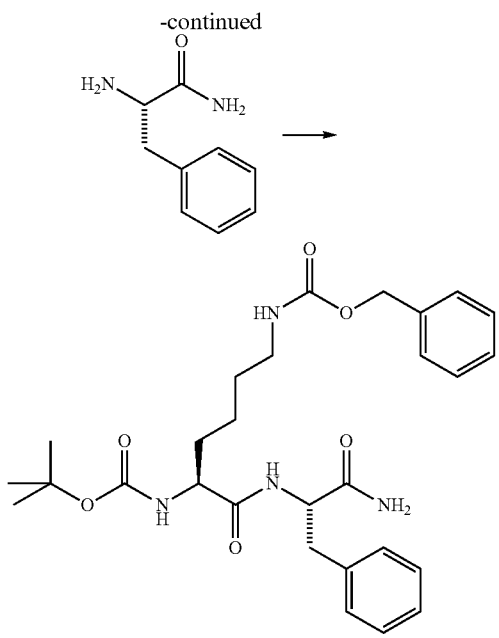

To mixture of L-phenylalaninamide hydrochloride (10.273 g, 51.19 mmol), $N^6$-[(benzyloxy)carbonyl]-$N^2$-(tert-butoxycarbonyl)-L-lysine (20.450 g, 53.75 mmol), and HOBt (22.8% $H_2O$, 9.731 g, 56.31 mmol) in DCM (200 mL) was added EDC (10.300 53.72 mmol) followed by triethylamine (7.488 mL, 53.72 mmol). After 16 h, the solution was concentrated under reduced pressure. The residue was dissolved in ethyl acetate (800 mL) and washed successively with sat aqueous $NaHCO_3$ (200 mL), brine (200 ml), 0.1 N aqueous HCl (200 mL), brine (200 mL), dried (anhydrous $Na_2SO_4$), filtered and concentrated. The solid was dissolved in ethyl acetate (500 mL) with heating (60° C.) and allowed to cool to ambient temperature with stirring. The solid isolated was by filtration and dried in vacuo to afford 25.5 g of a white solid (HPLC purity of 93 area % at 210 nm). Purification of 10.00 g of the solid by flash chromatography (1-3% methanol in DCM) afforded the title compound (9.42 g, adjusted yield 89%) as a white amorphous solid. $^1$H NMR (400 MHz, DMSO-$d_6$) δ 1.00-1.37 (m, 6 H), 1.37 (s, 9 H), 2.73-3.09 (m, 4 H), 3.67-3.80 (m, 1 H), 4.38-4.53 (m, 1 H), 5.01 (s, 2 H), 6.95 (d, J=8 Hz, 1 H), 7.08-7.45 (m, 13 H), 7.72 (d, J=8 Hz, 1 H); MS (ESI+) for $C_{28}H_{38}N_4O_6$ m/z 527.3 (M+H)$^+$; HPLC retention time=3.95 min.

Step 2. Preparation of N⁶-[(benzyloxy)carbonyl]-L-lysyl-L-phenylalaninamide trifluoroacetate

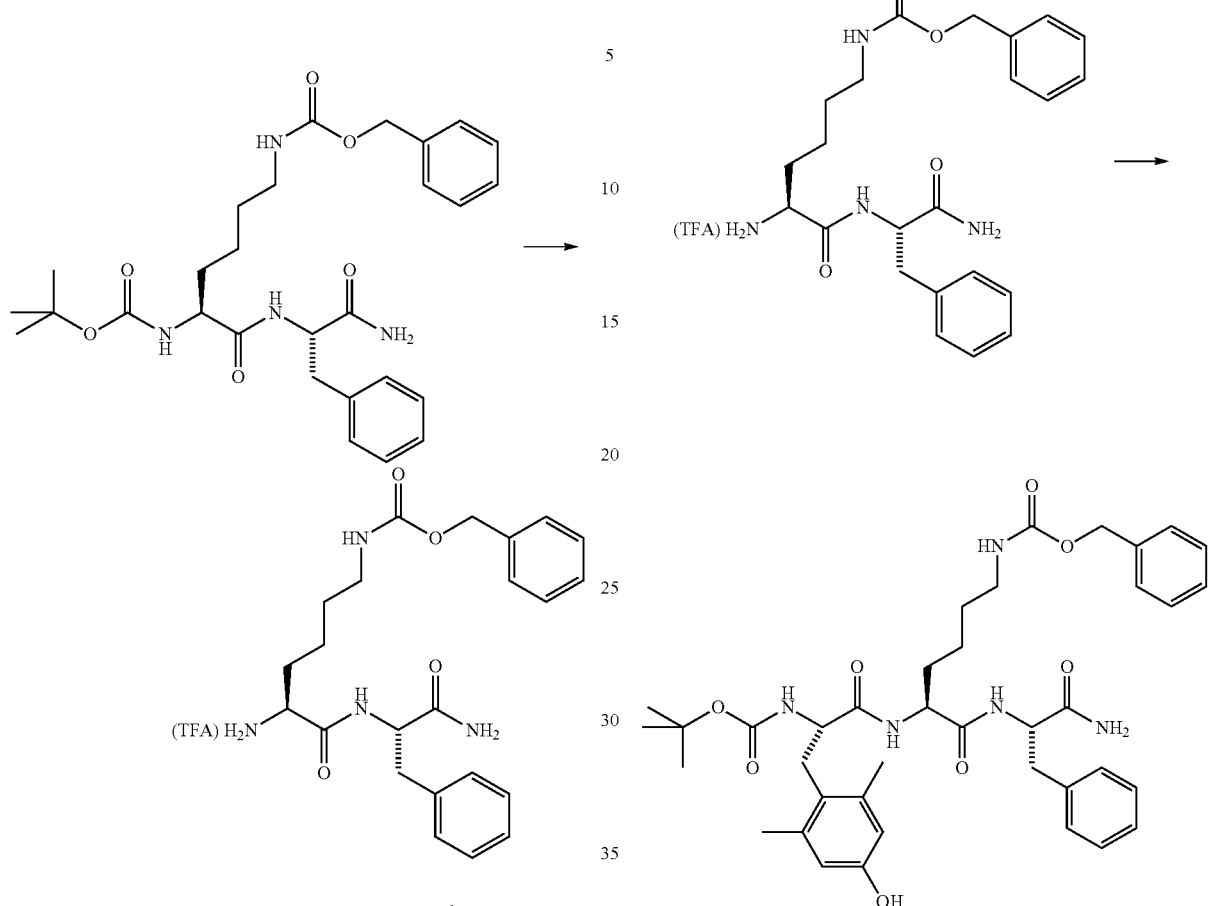

To a cooled (0-5° C.) suspension of N⁶-[(benzyloxy)carbonyl]-N²-(tert-butoxycarbonyl)-L-lysyl-L-phenylalaninamide (1.000 g, 1.90 mmol) in DCM (10 mL) was added trifluoroacetic acid (5.0 mL) providing complete dissolution. After 5 min, the ice bath was removed and the solution stirred at ambient temperature for 90 min. Volatiles were removed under reduced pressure and the residue concentrated from ethyl ether (2×25 mL). Drying in vacuo afforded the title compound (1.06 g) as a waxy solid containing excess TFA that was used without further purification. MS (ESI+) for $C_{23}H_{30}N_4O_4$ m/z 427.2 (M+H)⁺; HPLC retention time=2.92 min.

Step 3. Preparation of N-(tert-butoxycarbonyl)-2,6-dimethyl-L-tyrosyl-N⁶-[(benzyloxy)carbonyl]-L-lysyl-L-phenylalaninamide

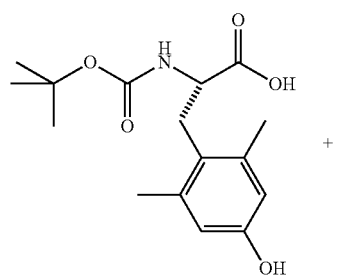

+

To a solution of N⁶-[(benzyloxy)carbonyl]-L-lysyl-L-phenylalaninamide trifluoroacetate (0.439 g, 0.95 mmol), HOBt (22.8% H₂O, 0.197 g, 1.14 mmol), N-(tert-butoxycarbonyl)-2,6-dimethyl-L-tyrosine (0.308 g, 1.00 mmol) and triethylamine (0.146 mL, 1.04 mmol) in THF (10 mL) was added EDC (0.218 g, 1.14 mmol). After 16 h, the reaction mixture was diluted with ethyl acetate (200 mL) and washed with sat aqueous NaHCO₃ (2×50 mL), brine (50 mL), aqueous 0.1 N HCl (2×50 mL), brine (50 mL), dried (anhydrous Na₂SO₄), filtered and concentrated under reduced pressure. The residue was purified by flash chromatography (1-3% methanol in DCM) to afford the title compound (0.260 g, 38%) as a white amorphous solid. ¹H NMR (400 MHz, DMSO-d₆) δ 1.01-1.66 (m, 6 H), 1.27 (s, 9 H), 2.16 (s, 6 H), 2.59-3.10 (m, 6 H), 3.98-4.10 (m, 1 H), 4.16-4.28 (m, 1 H), 4.35-4.47 (m, 1 H), 4.98 (s, 2 H), 6.34 (s, 2 H), 6.94 (br d, J=9 Hz, 1 H), 7.06 (br s, 1 H), 7.12-7.45 (m, 12 H), 7.69 (br d, J=8 Hz, 1 H), 7.98 (br d, J=8 Hz, 1 H), 8.88 (s, 1 H); MS (ESI+) for $C_{39}H_{51}N_5O_8$MS m/z 718.38 (M+H)⁺; HPLC retention time=4.08 min.

Step 4. Preparation of N²-[(benzyloxy)carbonyl]-N⁵-[{[(benzyloxy)carbonyl]amino}{[(benzyloxy)carbonyl]imino}methyl]-D-ornithyl-2,6-dimethyl-L-tyrosyl-N⁶-{[(benzyl)oxy]carbonyl}-L-lysyl-L-phenylalaninamide
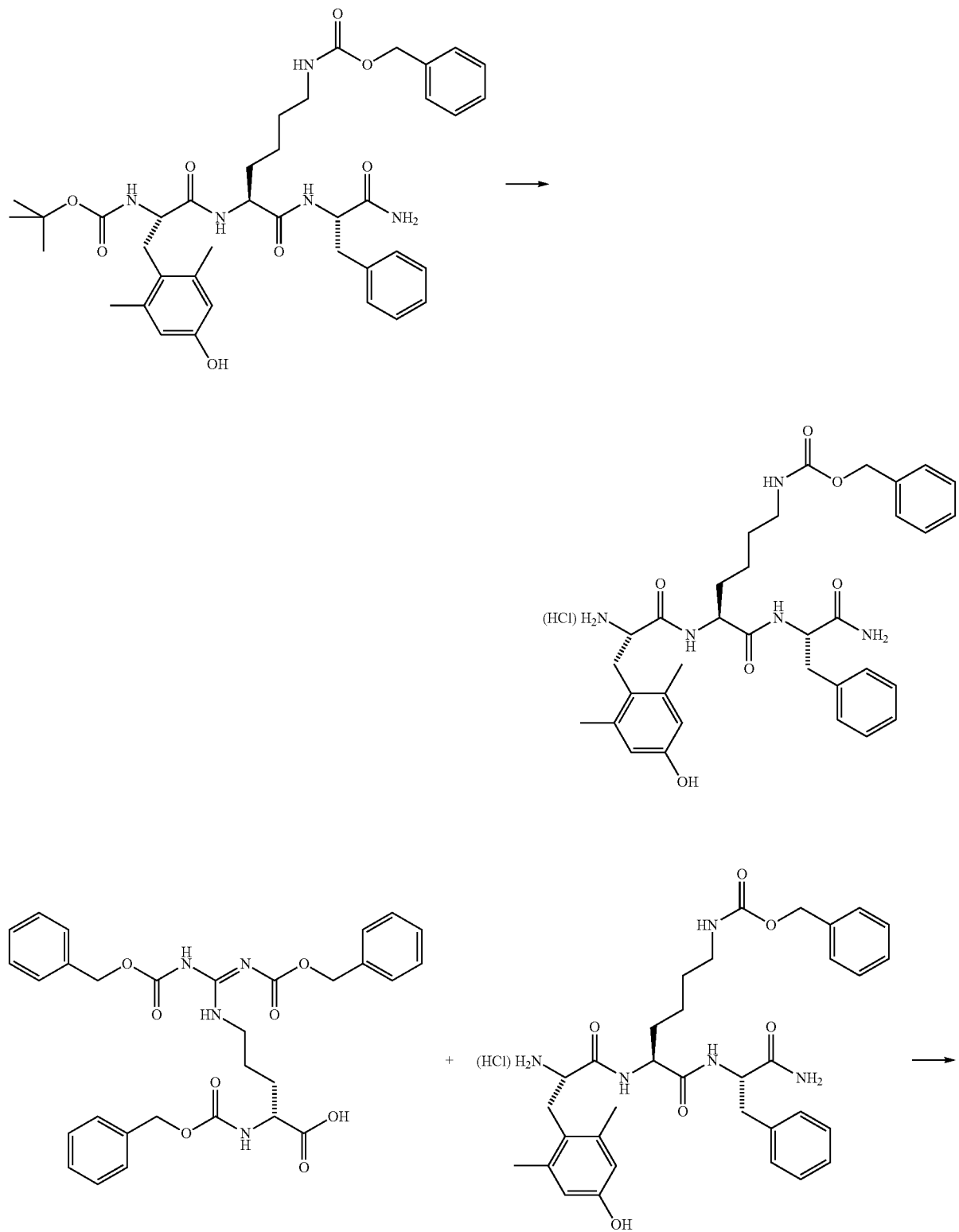

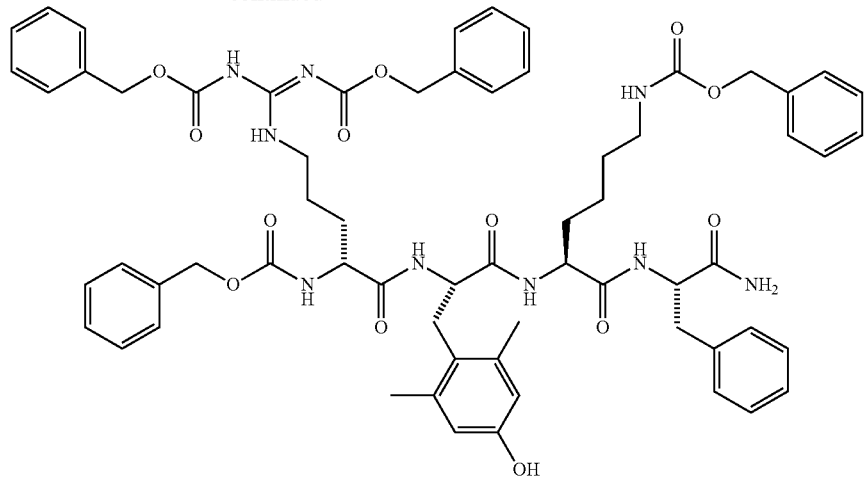

To a cooled (0-5° C.) solution of N-(tert-butoxycarbonyl)-2,6-dimethyl-L-tyrosyl-N⁶-[(benzyloxy)carbonyl]-L-lysyl-L-phenylalaninamide (0.260 g, 0.36 mmol) in DCM (2 mL) was added hydrogen chloride (4 M solution in 1,4-dioxane, 0.906 mL, 3.62 mmol After 5 min, the ice bath was removed and the solution stirred for 16 h at ambient temperature. Volatiles were removed under reduced pressure and the residue concentrated from ethyl acetate (2×50 ml) and ether (2×50 mL). Drying in vacuo afforded 2,6-dimethyl-L-tyrosyl-N⁶-[(benzyloxy)carbonyl]-L-lysyl-L-phenylalaninamide hydrochloride (224 mg) as a white amorphous solid which was used without further purification. MS (ESI+) for $C_{34}H_{43}N_5O_6$ m/z 618.3 (M+H)⁺; HPLC retention time=3.23 min.

To a mixture of 2,6-dimethyl-L-tyrosyl-N⁶-[(benzyloxy)carbonyl]-L-lysyl-L-phenylalaninamide hydrochloride (224 mg), N²-[(benzyloxy)carbonyl]-N⁵-[{[(benzyloxy)carbonyl]amino}{[(benzyloxy)carbonyl]imino}methyl]-D-ornithine (0.219 g, 0.38 mmol), HOBt (22.8% H₂O, 0.069 g, 0.40 mmol) and triethylamine (0.056 mL, 0.40 mmol) in THF (5 mL) was added EDC (0.083 g, 0.43 mmol). After 16 h, the mixture was diluted with ethyl acetate (200 mL) and washed with sat aqueous NaHCO₃ (2×50 mL), brine (50 mL), aqueous 0.1 N HCl (2×50 mL), brine (50 mL), dried (anhydrous Na₂SO₄), filtered and concentrated under reduced pressure. The residue was purified by flash chromatography (1-3% methanol in DCM) to afford the title compound (0.224 g, 53%) as a white amorphous solid. ¹H NMR (400 MHz, DMSO-d₆) δ 1.04-1.66 (m, 10 H), 2.12 (s, 6 H), 2.59-2.75 (m, 1H), 2.76-3.08 (m, 5 H), 3.70-3.88 (m, 2 H), 3.89-4.02 (m, 1 H), 4.08-4.21 (m, 1 H), 4.33-4.44 (m, 1 H), 4.44-4.57 (m, 1 H), 4.82-5.10 (m, 6 H), 5.20 (s, 2 H), 6.30 (s, 2 H), 7.02-7.48 (m, 29 H), 7.76 (br d, J=8 Hz, 1 H), 7.89 (br d, J=7 Hz, 1 H), 8.10 (br d, J=8 Hz, 1 H), 8.85 (s, 1 H), 9.17 (v br m, 2 H); MS (ESI+) for $C_{64}H_{73}N_9O_{13}$ m/z 1176.7 (M+H)⁺; HPLC retention time=4.90 min.

Step 5. Preparation of D-arginyl-2,6-dimethyl-L-tyrosyl-L-lysyl-L-phenylalaninamide

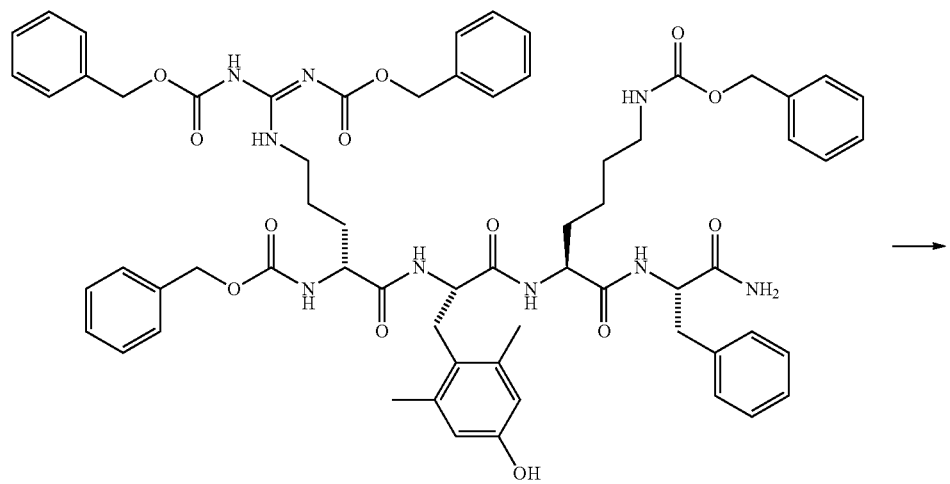

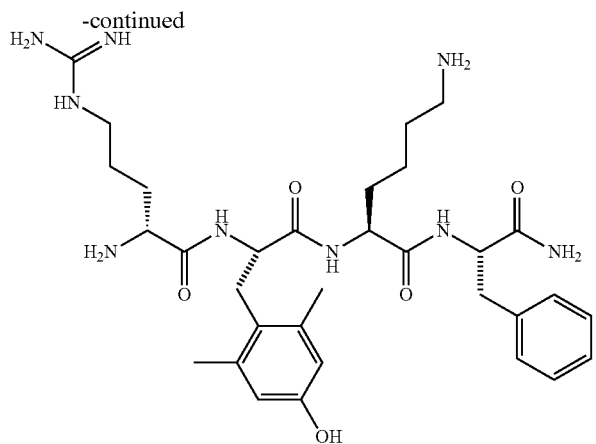

To a flask containing palladium (10 wt % on carbon powder, dry (Aldrich 520888), 0.022 g) and $N^2$-[(benzyloxy)carbonyl]-$N^5$-[{[(benzyloxy)carbonyl]amino}{[(benzyloxy)carbonyl]imino}methyl]-D-ornithyl-2,6-dimethyl-L-tyrosyl-$N^6$-{[(benzyl)oxy]carbonyl}-L-lysyl-L-phenylalaninamide (0.224 g, 0.19 mmol) was added methanol (8 mL) and acetic acid (0.043 ml, 0.76 mmol). The flask was subjected to 2 cycles of evacuation—hydrogen gas backfill and the mixture stirred under 1 atm of $H_2$ at 50° C. for 4 h. The mixture was cooled, filtered through Solka-Floc, and washed with additional methanol (25 mL). The combined washes were concentrated under reduced pressure and the residue lyophilized from water (20 mL) to afford the title compound (0.146 g, 94%) as a white amorphous powder. The compound was found to contain 21% w/w of acetate as determined by integration of the $^1$H NMR spectra. $^1$H NMR (400 MHz, $D_2O$) δ 1.05-1.28 (m, 4 H), 1.43-1.63 (m, 6 H), 1.79 (s, 8.3H, acetate), 2.09 (s, 6 H), 2.72-3.11 (m, 8H), 3.74 (t, J=6 Hz, 1 H), 4.16 (t, J=7 Hz, 1H), 4.43 (t, J=7 Hz, 1 H), 4.58 (t, J=8 Hz, 1H), 6.43 (s, 2 H), 7.12-7.32 (m, 5 H); MS (ESI+) for $C_{32}H_{49}N_9O_5$ m/z 640.3 (M+H)$^+$; HPLC retention time=2.24 min.

Route 1C

Step 1. Preparation of $N^6$-[(benzyloxy)carbonyl]-$N^2$-(tert-butoxycarbonyl)-L-lysyl-L-phenylalaninamide

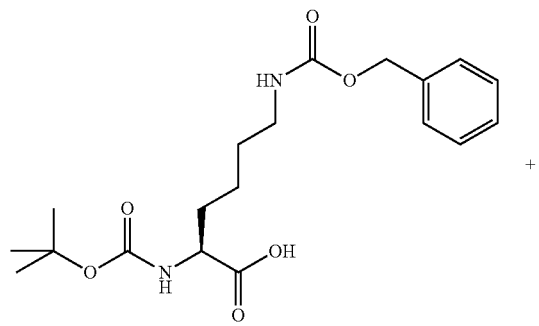

+

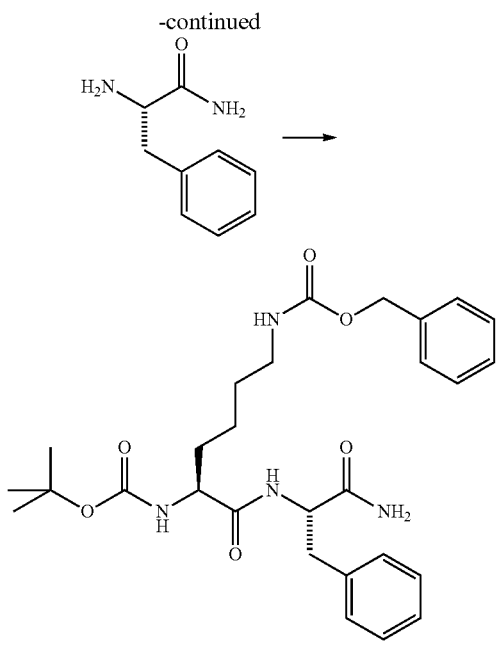

To a cooled (0-5° C.) solution of L-phenylalaninamide hydrochloride (1.000 g, 4.98 mmol), $N^6$-[(benzyloxy)carbonyl]-$N^2$-(tert-butoxycarbonyl)-L-lysine (1.953 g, 5.13 mmol), and HOBt (22.8% $H_2O$, 0.172 g, 1.00 mmol) in ethanol (7 mL) was added EDC (1.146 g, 5.98 mmol) followed by 4-methylmorpholine (1.096 mL, 9.97 mmol). After 5 min, the ice bath was removed and the mixture stirred at ambient temperature for 16 h. To the mixture was added water (21 mL) with vigorous stirring. After 10 min, solids were collected by filtration, washed with water (2×10 mL) and dried in vacuo. The solid was dissolved in hot (50° C.) ethanol (60 ml) and water (30 mL) and cooled to ambient temperature with stirring. The solids were collected by filtration, washed with water (2×30 mL) and dried in vacuo to afford the title compound (2.260 g, 86%) as a white amorphous solid. $^1$H NMR (DMSO-$d_6$) δ 1.00-1.33 (m, 6 H), 1.37 (s, 9 H), 2.70-3.10 (m, 4 H), 3.66-3.79 (m, 1 H), 4.36-4.53 (m, 1H), 5.00 (s, 2 H), 6.95 (br d, J=7 Hz, 1 H), 7.08-7.46 (m, 13 H), 7.72 (br d, J=8 Hz, 1 H); MS (ESI+) for $C_{28}H_{38}N_4O_6$ m/z 527.3 (M+H)$^+$; HPLC retention time=3.95 min.

Step 2. Preparation of N-(tert-butoxycarbonyl)-2,6-dimethyl-L-tyrosyl-$N^6$-[(benzyloxy)carbonyl]-L-lysyl-L-phenylalaninamide

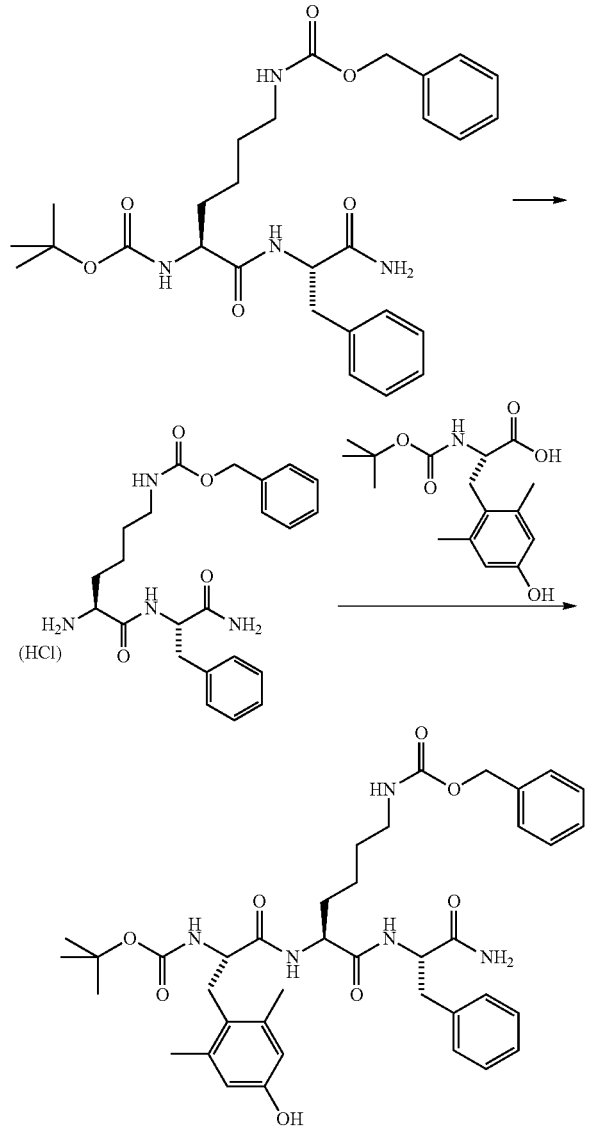

To a cooled (0-5° C.) suspension of $N^6$-[(benzyloxy)carbonyl]-$N^2$-(tert-butoxycarbonyl-L-lysyl-L-phenylalaninamide (2.200 g, 4.18 mmol) in DCM (40 mL)) was added hydrogen chloride (4 M solution in 1,4-dioxane, 10.444 mL, 41.78 mmol). After 5 min, the ice bath was removed and the solution stirred for 90 min at ambient temperature. Volatiles were removed under reduced pressure and the residue concentrated from DCM (2×25 ml) and ethyl acetate (25 mL) and dried in vacuo to afford $N^6$-[(benzyloxy)carbonyl]-L-lysyl-L-phenylalaninamide hydrochloride (1.330 g) as a white amorphous solid which was used without further purification. $^1$H NMR (400 MHz, DMSO-$d_6$) δ 1.22-1.46 (m, 4H), 1.62-1.82 (m, 2 H), 2.79-3.09 (m, 4 H), 3.63-3.81 (m, 1 H), 4.34-4.56 (m, 1 H), 5.01 (s, 2 H), 7.13 (br s, 1 H), 7.15-7.42 (m, 11 H), 7.60 (br s, 1 H), 8.12 (v br m, 3 H), 8.66 (d, J=8 Hz, 1 H); MS (ESI+) for $C_{23}H_{30}N_4O_4MS$ m/z 427.2 (M+H); HPLC retention time=2.91.

To a mixture of $N^6$-[(benzyloxy)carbonyl]-L-lysyl-L-phenylalaninamide hydrochloride (1.330 g, 4.18 mmol), 4-methylmorpholine (0.919 mL, 8.36 mmol), HOBt (22.8% $H_2O$, 0.144 g, 0.84 mmol) and N-(tert-butoxycarbonyl)-2,6-dimethyl-L-tyrosine (1.331 g, 4.30 mmol) in ethanol (50 mL) was added EDC (0.961 g, 5.01 mmol). After 16 h, water (150 mL) was added with vigorous stirring. After 10 min, the solids were collected by filtration, washed with water (2×15 mL) and dried in vacuo. The solid was dissolved in hot (50° C.) ethanol (80 ml) and water (50 mL) and cooled to ambient temperature with stirring. The solids were collected by filtration, washed with water (2×25 mL) and dried in vacuo to afford the title compound (2.680 g, 89%) as a white amorphous solid. $^1$H NMR (400 MHz, DMSO-$d_6$) δ 1.01-1.66 (m, 6 H), 1.27 (s, 9 H), 2.16 (s, 6 H), 2.61-3.090 (m, 6 H), 3.97-4.11 (m, 1 H), 4.17-4.30 (m, 1 H), 4.35-4.44 (m, 1 H), 4.98 (s, 2 H), 6.34 (s, 2 H), 6.94 (br d, J=9 Hz, 1 H), 7.06 (br s, 1 H), 7.13-7.44 (m, 12 H), 7.70 (br d, J=8 Hz, 1 H), 7.98 (br d, J=8 Hz, 1 H), 8.88 (s, 1H); MS (ESI+) for $C_{39}H_{51}N_5O_8MS$ m/z 718.4 (M+H)$^+$; HPLC retention time=4.08 min.

Step 3. Preparation of $N^2$-[(benzyloxy)carbonyl]-$N^5$-[{[(benzyloxy)carbonyl]amino}{[(benzyloxy)carbonyl]imino}methyl]-D-ornithyl-2,6-dimethyl-L-tyrosyl-$N^6$-{[(benzyl)oxy]carbonyl}-L-lysyl-L-phenylalaninamide

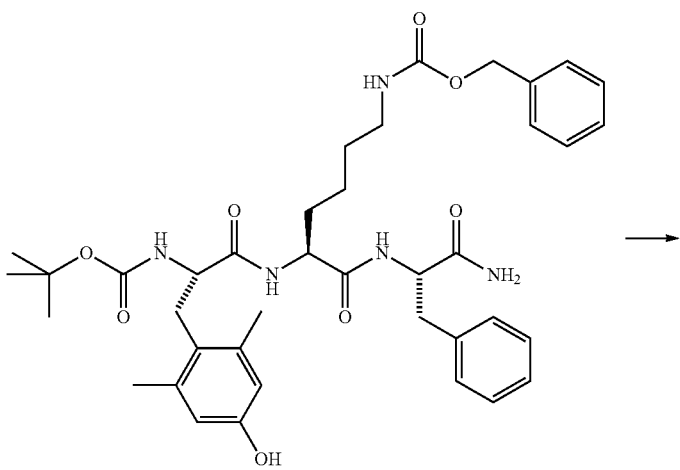

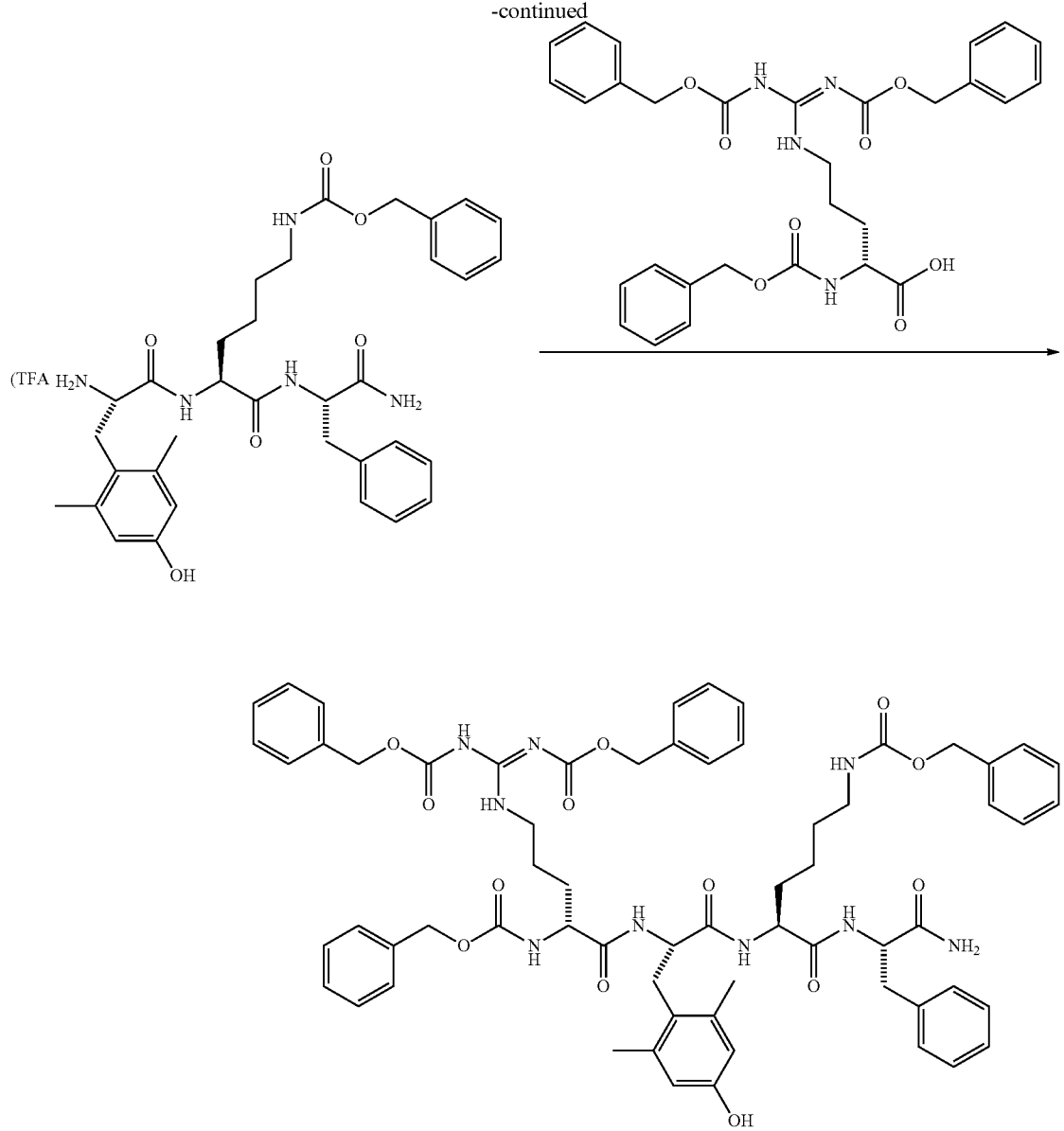

To a cooled (0-5° C.) mixture of N-(tert-butoxycarbonyl)-2,6-dimethyl-L-tyrosyl-N⁶-[(benzyloxy)carbonyl]-L-lysyl-L-phenylalaninamide (0.350 g, 0.49 mmol) in DCM (5 mL) was added TFA (2.5 mL). After 5 min, the ice bath was removed and the solution stirred at ambient temperature for 45 min. Volatiles were removed under reduced pressure and the residue concentrated from DCM (2×25 ml) and toluene (2×20 mL) and dried in vacuo to afford 2,6-dimethyl-L-tyrosyl-N⁶-[(benzyloxy)carbonyl]-L-lysyl-L-phenylalaninamide hydrochloride trifluoroacetate (0.355 g) as a white solid that was used without further purification. MS (ESI+) for $C_{34}H_{43}N_5O_6$ m/z 618.3 (M+H)⁺; HPLC retention time=3.22 min.

To solution of N²-[(benzyloxy)carbonyl]-N⁵-{[(benzyloxy)carbonyl]amino}{[(benzyloxy)carbonyl]imino}methyl]-D-ornithine (0.290 g, 0.50 mmol) in warm (30° C.) 2-propanol (5 mL) was added a mixture of 2,6-dimethyl-L-tyrosyl-N⁶-[(benzyloxy)carbonyl]-L-lysyl-L-phenylalaninamide hydrochloride trifluoroacetate (0.355 g, 0.49 mmol) in 2-propanol (5 mL) followed by 4-methylmorpholine (0.107 mL, 0.98 mmol) and HOBt (22.8% H₂O, 0.017 g, 0.10 mmol). The solution was allowed to cool to ambient temperature and EDC (0.112 g, 0.59 mmol) was added. After 16 h, water (30 mL) was added with vigorous stirring. After 20 min, solids were collected by filtration, washed with water (2×20 mL) and dried in vacuo. The solid was purified by flash chromatography (0-3% methanol in DCM) to afford the title compound (0.445 g, 78%) as a white amorphous solid. ¹H NMR (400 MHz, DMSO-d₆) δ 1.06-1.64 (m, 10 H), 2.12 (s, 6 H), 2.60-2.72 (m, 1 H), 2.76-3.06 (m, 5 H), 3.68-3.85 (m, 2 H), 3.88-4.02 (m, 1 H), 4.04-4.21 (m, 1 H), 4.33-4.44 (m, 1 H), 4.45-4.60 (m, 1 H), 4.86-5.08 (m, 6 H), 5.20 (s, 2 H), 6.30 (s, 2 H), 7.01-7.48 (m, 29 H), 7.75 (br d, J=8 Hz, 1 H), 7.89 (br d, J=8 Hz, 1 H), 8.10 (br d, J=8 Hz, 1 H), 8.85 (s, 1 H), 9.162 (v br m, 2 H); MS (ESI+) for $C_{64}H_{73}N_9O_{13}$ m/z 1176.6 (M+H)⁺; HPLC retention time=4.89 min.

Step 4. Preparation of D-arginyl-2,6-dimethyl-L-tyrosyl-L-lysyl-L-phenylalaninamide

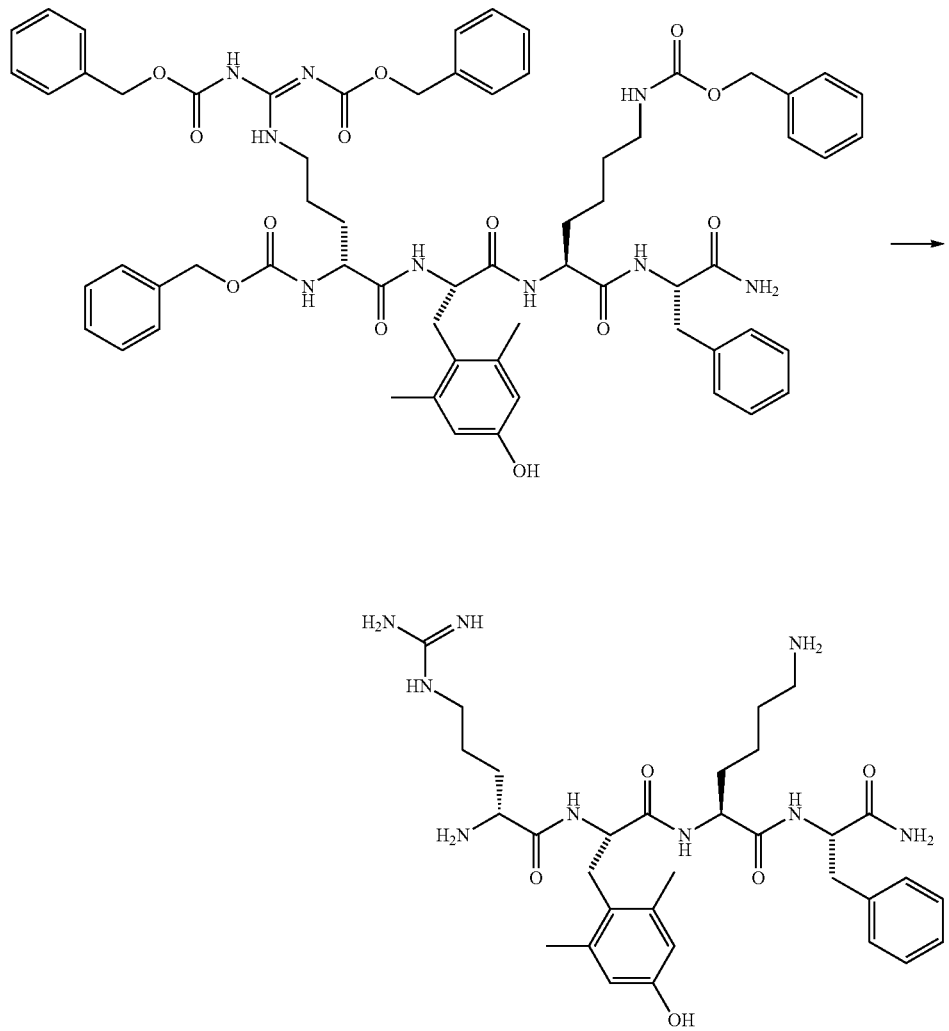

To a flask containing palladium (10 wt % on carbon powder, dry (Aldrich 520888), 0.020 g) and $N^2$-[(benzyloxy)carbonyl]-$N^5$-[{[(benzyloxy)carbonyl]amino}{[(benzyloxy)carbonyl]imino}methyl]-D-ornithyl-2,6-dimethyl-L-tyrosyl-$N^6$-{[(benzyl)oxy]carbonyl}-L-lysyl-L-phenylalaninamide (0.194 g, 0.17 mmol) was added methanol (7 mL) and acetic acid (0.038 ml, 0.66 mmol). The flask was subjected to 2 cycles of evacuation—hydrogen gas backfill and the mixture stirred under 1 atm of $H_2$ at 50° C. for 4 h. The mixture was cooled, filtered through Solka-Floc, and washed with additional methanol (25 mL). The combined washes were concentrated under reduced pressure and the residue lyophilized from water (20 mL) to afford the title compound (0.146 g, 92%) as a white amorphous powder. The compound was found to contain 21% w/w of acetate as determined by integration of the $^1$H NMR spectra. $^1$H NMR ($D_2O$) δ 1.06-1.26 (m, 4 H), 1.44-1.64 (m, 6 H), 1.79 (s, 8.4H, acetate), 2.09 (s, 6 H), 2.70-3.06 (m, 8 H), 3.79 (t, J=6 Hz, 1 H), 4.16 (t, J=7 Hz, 1 H), 4.43 (t, J=7 Hz, 1 H), 4.58 (t, J=8 Hz, 1 H), 6.42 (s, 2 H), 7.14-7.30 (m, 5 H); MS (ESI+) for $C_{32}H_{49}N_9O_5$ m/z 640.4 (M+H)$^+$; HPLC retention time=2.24 min.

Route 2A
Step 1. Preparation of N²-[(benzyloxy)carbonyl]-N⁵-[{[(benzyloxy)carbonyl]amino}{[(benzyloxy)carbonyl]imino}methyl]-D-ornithyl-O-benzyl-2,6-dimethyl-L-tyrosyl-N⁶-{[(benzyl)oxy]carbonyl}-L-lysyl-L-phenylalaninamide
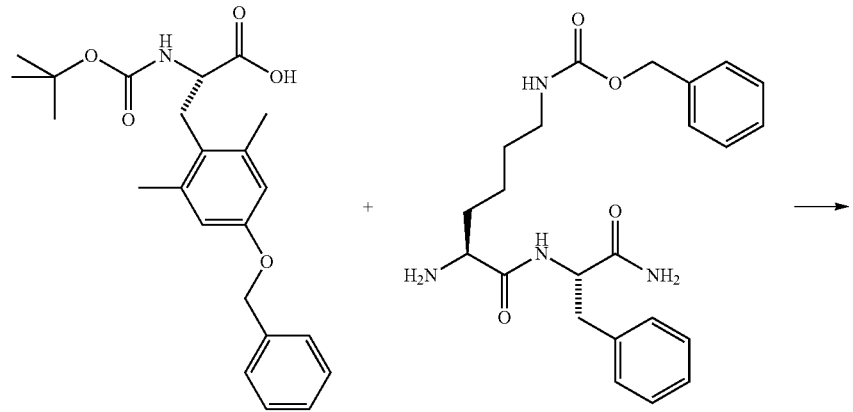
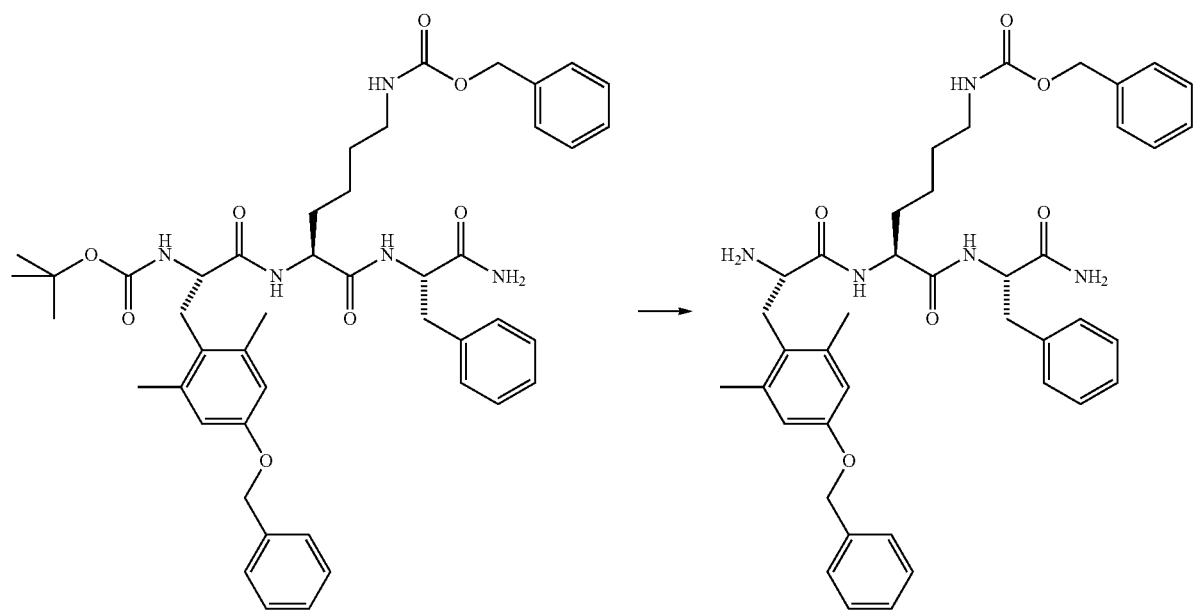

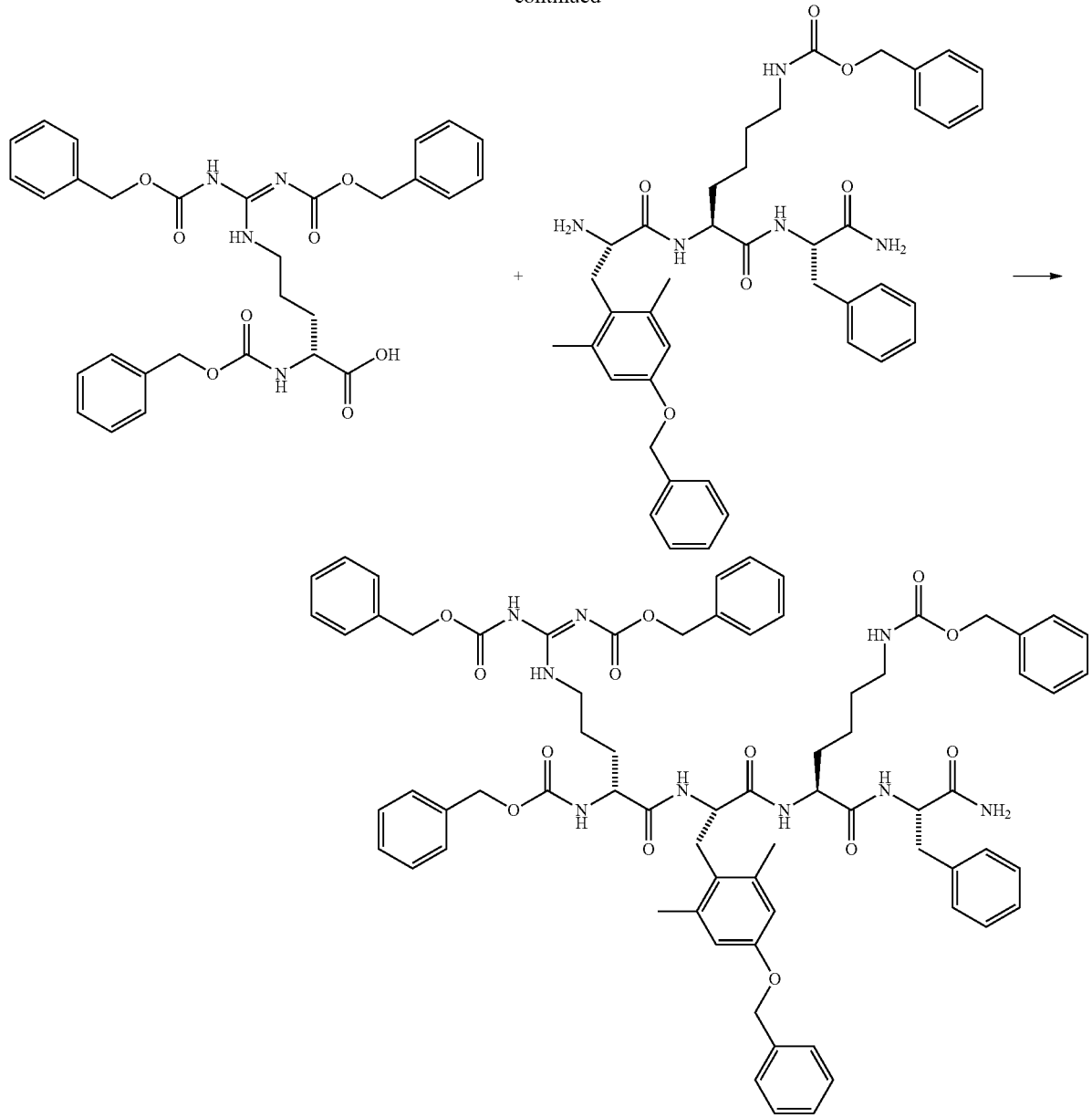

To a mixture of O-benzyl-N-(tert-butoxycarbonyl)-2,6-dimethyl-L-tyrosine (0.206 g, 0.52 mmol), $N^6$-[(benzyloxy)carbonyl]-L-lysyl-L-phenylalaninamide (Scheme 1A, 0.200 g, 0.47 mmol) and HOBt monohydrate (0.086 g, 0.56 mmol) in THF/2-MeTHF (1:1, 4.8 mL) was added EDC (0.108 g, 0.56 mmol). After 1 h, additional THF/2-MeTHF (1:1, 4.8 mL) was added and the reaction stirred at ambient temperature for 16 h. Aqueous $KHSO_4$ (5% w/w, 1.6 mL) was added and stirring continued for 45 min. The mixture was diluted with ethyl acetate (40 mL) and aqueous $KHSO_4$ (5% w/w, 5 mL), the layers separated and the organic layer washed with water (10 mL), aqueous $Na_2CO_3$ (5% w/w, 5 mL), water (10 mL) and concentrated. The residue was dried (50° C. in vacuo), suspended in THF (5 mL) and methanesulfonic acid (0.091 mL, 1.41 mmol) added. After 30 min the mixture was warmed to 50° C. for 1 h and additional THF (5 mL) added. The mixture was stirred at 50° C. for 3 h, allowed to cool to ambient temperature and stirred an additional 48 h. Additional methanesulfonic acid (0.091 mL, 1.41 mmol) was added and the mixture warmed to 50° C. for 4 h. The mixture was cooled to ambient temperature and triethylamine (0.556 mL, 3.99 mmol) was added followed by HOBt monohydrate (0.086 g, 0.56 mmol), $N^2$-[(benzyloxy)carbonyl]-$N^5$-[{[(benzyloxy)carbonyl]amino}{[(benzyloxy)carbonyl]imino}methyl]-D-ornithine (0.270 g, 0.47 mmol) and EDC (0.108 g, 0.56 mmol). After 16 h, aqueous $KHSO_4$ (5% w/w, 2.5 mL) was added and the mixture stirred for 30 min. Aqueous $Na_2CO_3$ (5% w/w, 2.5 ml) was added and mixture stirred for 90 min. The mixture was diluted with ethyl acetate (50 mL) and the layers separated. The organic layer was washed with sat aqueous $NaHCO_3$ (20 mL) and the precipitate present in the organic phase was collected by filtration and washed with water (10 mL), ethyl ether (10 mL). Drying (50° C. in vacuo) afforded the title compound (363 mg) as a white amorphous solid (HPLC purity of 91 area % at 210 nm). $^1$H NMR (400 MHz, DMSO-d$_6$) δ 1.06-1.64 (m, 10 H), 2.18 (s, 6 H), 2.64-3.05 (m, 6 H), 3.70-3.83 (m, 2 H), 3.92-4.00 (m, 1 H), 4.10-4.20 (m, 1 H), 4.35-4.47 (m, 1 H), 4.53-4.65 (m, 1 H), 4.88-5.06 (m, 8 H), 5.19 (s, 2 H), 6.53 (s, 2 H), 7.05-7.48 (m, 34 H), 7.78 (br d, J=8 Hz, 1 H), 7.92 (br d, J=8 Hz, 1 H), 8.14 (br d, J=9 Hz, 1 H), 9.17 (v br m, 2 H); MS (ESI+) for C$_{71}$H$_{79}$N$_9$O$_{13}$ m/z 1266.7 (M+H)$^+$; HPLC retention time=5.54 min.

Step 2. Preparation of D-arginyl-2,6-dimethyl-L-tyrosyl-L-lysyl-L-phenylalaninamide

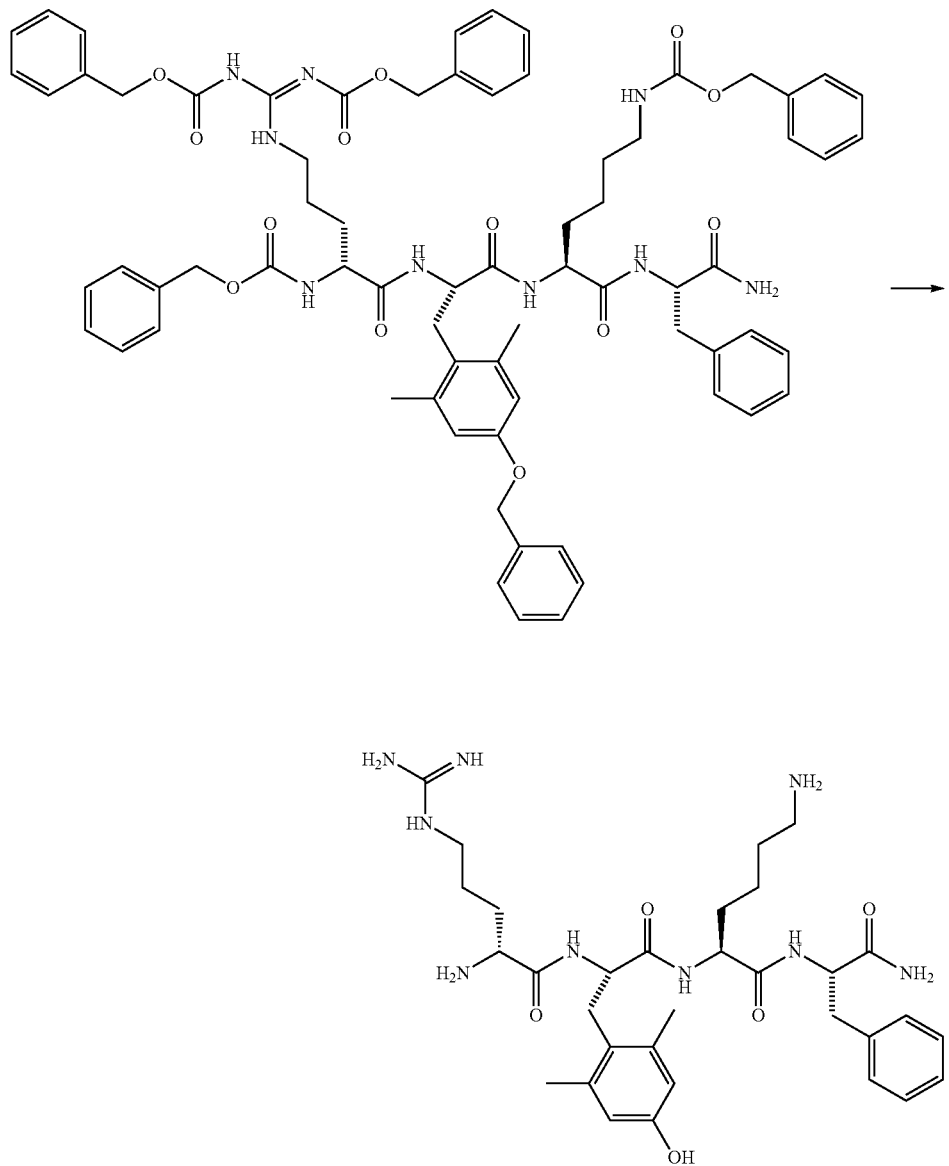

To a flask containing palladium (10 wt % on carbon powder, dry (Aldrich 520888), 0.020 g) and N$^2$-[(benzyloxy)carbonyl]-N$^5$-[{[(benzyloxy)carbonyl]amino}{[(benzyloxy)carbonyl]imino}methyl]-D-ornithyl-O-benzyl-2,6-dimethyl-L-tyrosyl-N$^6$-{[(benzyl)oxy]carbonyl}-L-lysyl-L-phenylalaninamide (0.100 g, 0.08 mmol) was added methanol (4 mL) and acetic acid (0.018 ml, 0.32 mmol). The flask was subjected to 2 cycles of evacuation—hydrogen gas backfill and the mixture stirred under 1 atm of H$_2$ at 50° C. for 4 h. The mixture was cooled, filtered through Solka-Floc, and washed with additional methanol (15 mL). The combined washes were concentrated under reduced pressure and the residue lyophilized from water (12 mL) to afford 59 mg of a solid (HPLC purity of 84 area % at 210 nm) that was further purified by CombiFlash chromatography [15.5 g RediSep C-18 Aq gold silica gel cartridge, solvent gradient: 100% water (0.1% TFA) to 100% acetonitrile (0.07% TFA)] and lyophilized to afford the title compound [26 mg, 34% (tris trifluoroacetate)] as a white amorphous solid. $^1$H NMR (400 MHz, D$_2$O) δ 1.05-1.28 (m, 4 H), 1.43-1.69 (m, 6 H), 2.10 (s, 6 H), 2.71-3.08 (m, 8 H), 3.89 (t, J=6 Hz, 1 H), 4.16 (t, J=7 Hz, 1 H), 4.40-4.46 (m, 1 H), 4.61 (t, J=8 Hz, 1 H), 6.43 (s, 2 H), 7.13-7.20 (m, 5 H); MS (ESI+) for C$_{32}$H$_{49}$N$_9$O$_5$ m/z 640.5 (M+H)$^+$; HPLC retention time=2.26 min.

Route 3A

Step 1. Preparation of N²-(tert-butoxycarbonyl)-N⁶-{[(2-chlorobenzyl)oxy]carbonyl}-L-lysyl-L-phenylalaninamide

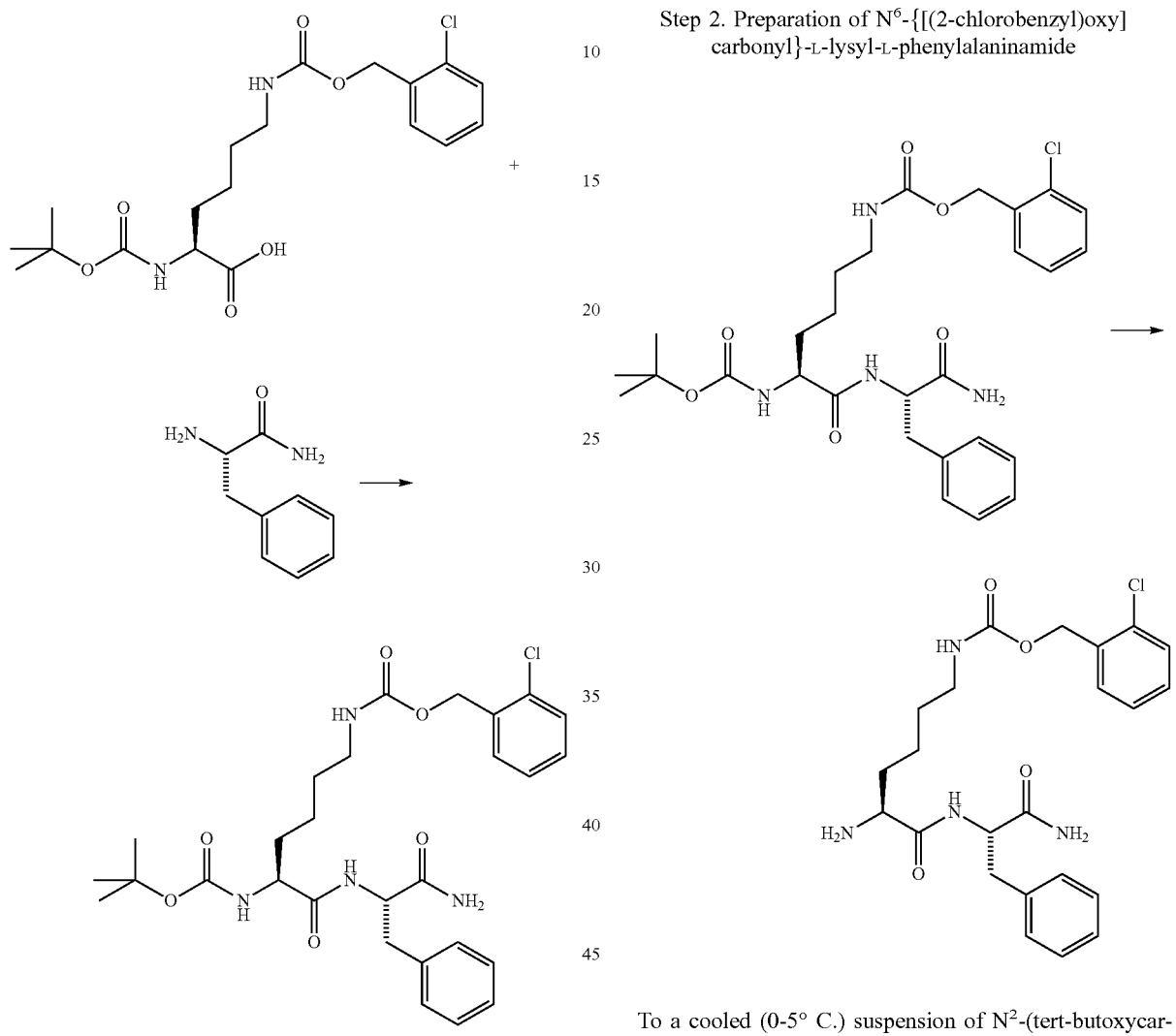

Step 2. Preparation of N⁶-{[(2-chlorobenzyl)oxy]carbonyl}-L-lysyl-L-phenylalaninamide To mixture of L-phenylalaninamide hydrochloride (1.20 g, 6.00 mmol), N²-(tert-butoxycarbonyl)-N⁶-{[(2-chlorobenzyl)oxy]carbonyl}-L-lysine (3.04 g, 7.32 mmol), and HOBt monohydrate (1.01 g, 6.60 mmol) in DCM (30 mL) was added BOP reagent (2.79 g, 6.30 mmol) followed by DIPEA (2.09 mL, 12.0 mmol). After 30 min, additional DCM (10 mL) was added to provide improved dissolution. After 16 h, the solution was concentrated under reduced pressure. The residue was dissolved in ethyl acetate (200 mL) and washed successively with sat aqueous NaHCO₃ (2×100 mL), brine (100 ml), 0.1 N aqueous HCl (2×100 mL), brine (100 mL), dried (anhydrous Na₂SO₄), filtered and concentrated. The solid was dissolved in ethyl acetate (150 mL) and hexanes (100 mL) with heating (60° C.) and allowed to cool to ambient temperature with stirring. The solid was collected by filtration, washed with hexanes (2×25 mL) and dried (50° C. in vacuo) to afford the title product (2.69 g, 80%) as a white amorphous solid. ¹H NMR (300 MHz, DMSO-d₆) δ 1.00-1.48 (m, 6 H), 1.36 (s, 9 H), 2.70-3.06 (m, 4 H), 3.68-3.80 (m, 1 H), 4.38-4.51 (m, 1 H), 5.08 (s, 2 H), 6.91 (br d, J=7 Hz, 1 H), 7.09 (br s, 1 H), 7.12-7.26 (m, 5 H), 7.27-7.42 (m, 4 H), 7.42-7.50 (m, 2 H), 7.69 (br d, J=8 Hz, 1 H); MS (ESI+) for $C_{28}H_{37}ClN_4O_6$ m/z 561.3 (M+H)⁺, HPLC retention time=4.16 min.

To a cooled (0-5° C.) suspension of N²-(tert-butoxycarbonyl)-N⁶-{[(2-chlorobenzyl)oxy]carbonyl}-L-lysyl-L-phenylalaninamide (1.500 g, 2.67 mmol) in DCM (10 mL) was added trifluoroacetic acid (5.0 mL) providing complete dissolution. After 5 min, the ice bath was removed and the solution stirred at ambient temperature for 45 min. Volatiles were removed under reduced pressure and the residue concentrated from ethyl ether (2×25 mL). The residue was partitioned between ethyl acetate (100 mL) and sat aqueous NaHCO₃ (100 mL), the layers separated and the aqueous layer extracted with ethyl acetate (2×100 mL). The organic extracts were combined, washed with brine (100 mL), dried (anhydrous Na₂SO₄), filtered and concentrated to afford the title compound (1.03 g, 84%) as a white amorphous powder. ¹H NMR (300 MHz, CDCl₃) δ 1.09-1.55 (m, 6 H), 2.79-3.05 (m, 4 H), 3.17-3.25 (m, 1 H), 3.42 (very br s, 2 H), 4.43-4.52 (m, 1H), 5.02 (s, 2 H), 7.09 (br s, 1 H), 7.13-7.41 (m, 8 H), 7.43-7.50 (m, 3 H), 8.08 (br d, J=8 Hz, 1 H); MS (ESI+) for $C_{23}H_{29}ClN_4O_4$ m/z 461.3 (M+H)⁺; HPLC retention time=3.16 min.

Step 3. Preparation of N-(tert-butoxycarbonyl)-2,6-dimethyl-L-tyrosyl-N⁶-{[(2-chlorobenzyl)oxy]carbonyl}-L-lysyl-L-phenylalaninamide

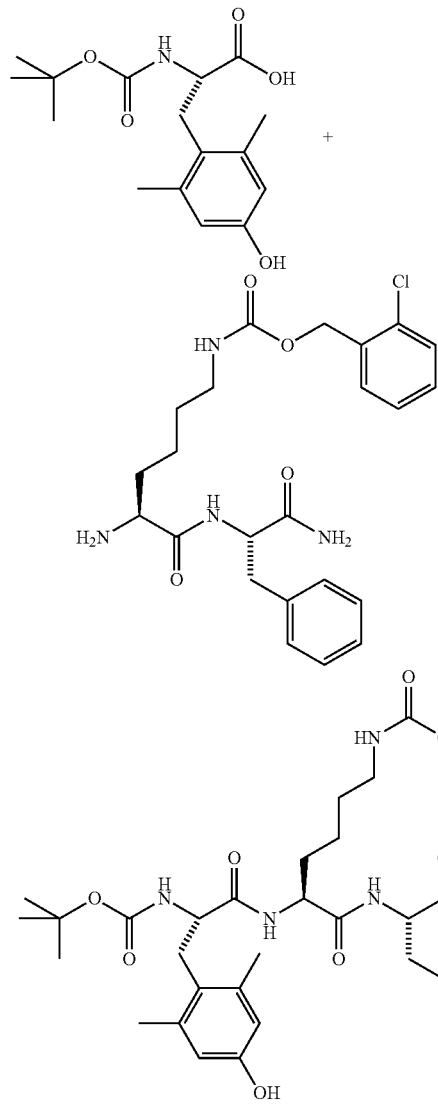

To a solution of N-(tert-butoxycarbonyl)-2,6-dimethyl-L-tyrosine (0.282 g, 0.91 mmol), HOBt monohydrate (0.159 g, 1.04 mmol), and N⁶-{[(2-chlorobenzyl)oxy]carbonyl}-L-lysyl-L-phenylalaninamide (0.400 g, 0.87 mmol) in THF (9 mL) was added EDC (0.200 g, 1.04 mmol). After 16 h, the reaction mixture was diluted with ethyl acetate (200 mL) and washed with sat aqueous NaHCO₃ (2×100 mL), brine (100 mL), aqueous 0.1 N HCl (2×100 mL), brine (100 mL), dried (anhydrous Na₂SO₄), filtered and concentrated under reduced pressure. The residue was purified by flash chromatography (1-4% methanol in DCM) to afford the title compound (0.521 g, 80%) as a white amorphous solid. $^1$H NMR (300 MHz, DMSO-d₆) δ 1.01-1.66 (m, 6 H), 1.27 (s, 9 H), 2.16 (s, 6 H), 2.60-3.05 (m, 6 H), 3.98-4.10 (m, 1 H), 4.17-4.28 (m, 1 H), 4.35-4.48 (m, 1 H), 5.06 (s, 2 H), 6.34 (s, 2 H), 6.90 (br d, J=9 Hz, 1 H), 7.03 (br s, 1 H), 7.13-7.39 (m, 9 H), 7.41-7.50 (m, 2 H), 7.68 (br d, J=7 Hz, 1 H), 7.94 (br d, J=8 Hz, 1 H), 8.45 (s, 1H); MS (ESI+) for C₃₉H₅₀ClN₅O₈ m/z 752.6 (M+H)⁺; HPLC retention time=4.25 min.

Step 4. Preparation of 2,6-dimethyl-L-tyrosyl-N⁶-{[(2-chlorobenzyl)oxy]carbonyl}-L-lysyl-L-phenylalaninamide

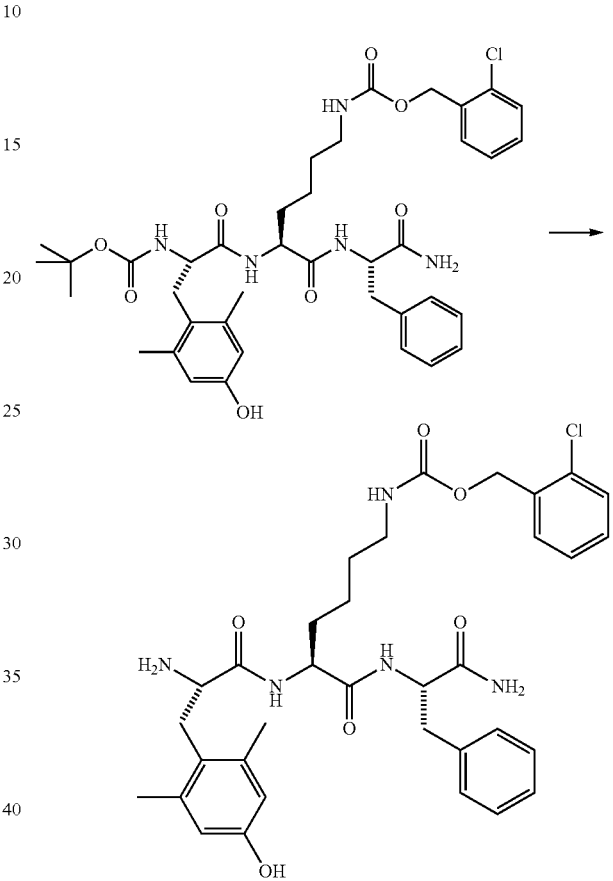

To a cooled (0-5° C.) suspension of N-(tert-butoxycarbonyl)-2,6-dimethyl-L-tyrosyl-N⁶-{[(2-chlorobenzyl)oxy]carbonyl}-L-lysyl-L-phenylalaninamide (0.521 g, 0.69 mmol) in DCM (10 mL) was added trifluoroacetic acid (5 mL) providing dissolution. After 5 min, the ice bath was removed and the solution stirred at ambient temperature for 45 min. Volatiles were removed under reduced pressure the solid evaporated from ethyl ether (2×50 mL). The solid was partitioned between DCM/2,2,2-trifluoroethanol (7:3, 200 mL) and sat aqueous NaHCO₃ (100 mL). The layers separated and the aqueous layer extracted with additional DCM/2,2,2-trifluoroethanol (7:3, 2×100 mL). The organic layers were combined and washed with brine (100 mL), dried (anhydrous Na₂SO₄), filtered and concentrated to afford the title compound (0.410 g, 91%) as a white amorphous solid. $^1$H NMR (400 MHz, CD₃OD) δ 1.23-1.31 (m, 2 H), 1.44-1.55 (m, 2 H), 1.56-1.81 (m, 2 H), 2.25 (s, 6 H), 2.71-2.77 (m, 1 H), 2.92-3.00 (m, 2 H), 3.11 (t, J=7 Hz, 2 H), 3.16-3.21 (m, 1 H), 3.55 (dd, J=8, 6 Hz, 1 H), 4.25 (dd, J=8, 6 Hz, 1 H), 4.59 (dd, J=9, 6 Hz, 1 H), 5.17 (s, 2 H), 6.47 (s, 2 H), 7.17-7.48 (m, 10 H); MS (ESI+) for C₃₄H₄₂ClN₅O₆ m/z 652.5 (M+H)⁺; HPLC retention time 3.40 min.

Step 5. Preparation of $N^5$-[amino(nitroimino)methyl]-$N^2$-(tert-butoxycarbonyl)-D-ornithyl-2,6-dimethyl-L-tyrosyl-$N^6$-{[(2-chlorobenzyl)oxy]carbonyl}-L-lysyl-L-phenylalaninamide

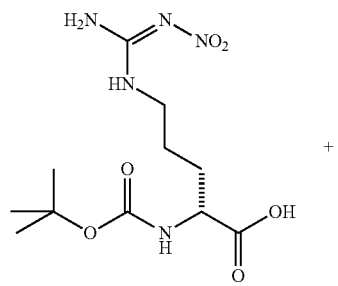

+

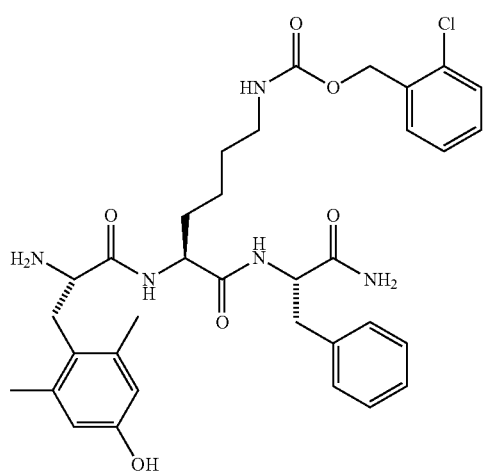

→

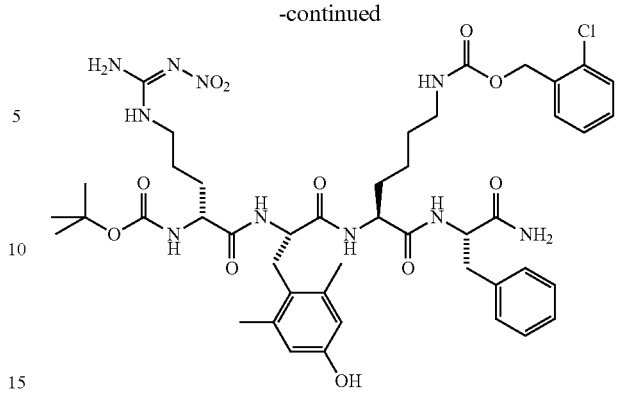

To a stirred solution of 2,6-dimethyl-L-tyrosyl-$N^6$-{[(2-chlorobenzyl)oxy]carbonyl}-L-lysyl-L-phenylalaninamide (0.210 g, 0.32 mmol) and $N^5$-[amino(nitroimino)methyl]-$N^2$-(tert-butoxycarbonyl)-D-ornithine (0.113 g, 0.35 mmol) in DMF (3 mL) was added HATU (0.135 g, 0.35 mmol) followed by DIPEA (0.112 mL, 0.64 mmol). After 16 h, volatiles were removed in vacuo and the residue purified by flash chromatography (1-4% MeOH in DCM) to afford the title compound (277 mg, 90%) as a tan solid. $^1$H NMR (400 MHz, DMSO-$d_6$) δ 1.16-1.29 (m, 8 H), 1.35 (s, 9 H), 1.45-1.61 (m, 2 H), 2.16 (s, 6 H), 2.65-3.17 (m, 8 H), 3.83-3.94 (m, 1 H), 4.08-4.21 (m, 1 H), 4.33-4.45 (m, 1 H), 4.48-4.60 (m, 1 H), 5.07 (s, 2 H), 6.31 (s, 2 H), 8.85 (br d, J=8 Hz, 1 H), 7.09 (s, 1 H), 7.13-7.54 (m, 11 H), 7.78 (br d, J=8 Hz, 1 H), 7.86-8.00 (m, 2 H), 8.44 (br m, 1 H), 8.87 (s, 1 H); MS (ESI+) for $C_{45}H_{61}ClN_{10}O_{11}$ m/z 953.5 (M+H)$^+$; HPLC retention time=3.97 min.

Step 6. Preparation of D-arginyl-2,6-dimethyl-L-tyrosyl-L-lysyl-L-phenylalaninamide

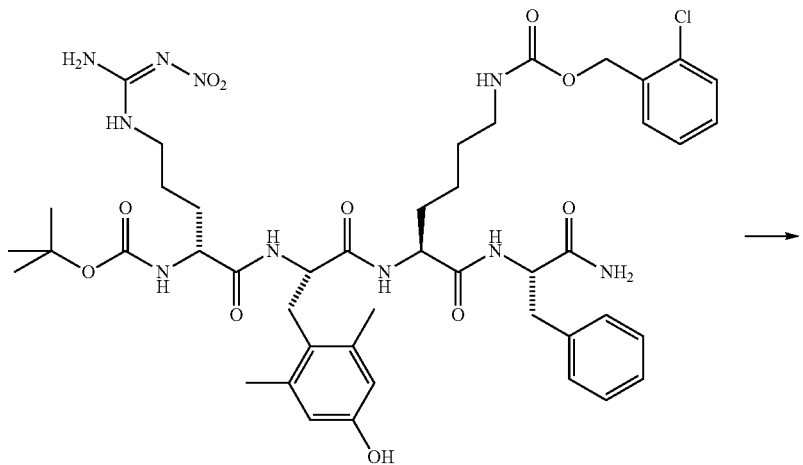

→

-continued

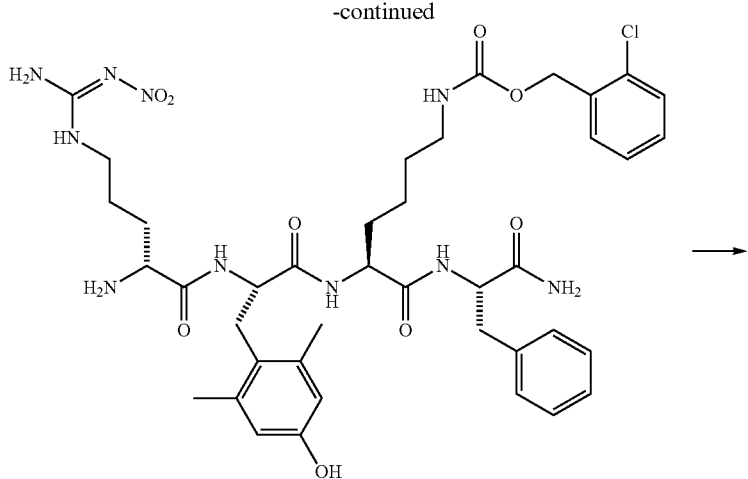

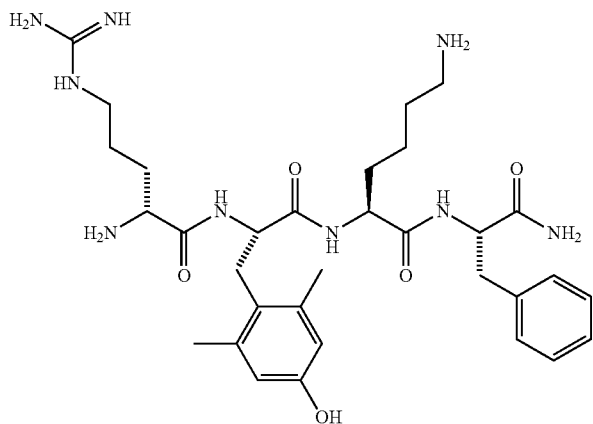

To a cooled (0-5° C.) solution of $N^5$-[amino(nitroimino)methyl]-$N^2$-(tert-butoxycarbonyl)-D-ornithyl-2,6-dimethyl-L-tyrosyl-$N^6$-{[(2-chlorobenzyl)oxy]carbonyl}-L-lysyl-L-phenylalaninamide (0.180 g, 0.19 mmol) in DCM (1 mL) was added TFA (0.5 mL). After 5 min, the ice bath was removed and the solution stirred for 45 min at ambient temperature. Volatiles were removed under reduced pressure and the residue concentrated from ethyl acetate (2×20 ml) and ether (2×10 mL). Drying in vacuo afforded $N^5$-amino(nitroimino)methyl-D-ornithyl-2,6-dimethyl-L-tyrosyl-$N^6$-{[(2-chlorobenzyl)oxy]carbonyl}-L-lysyl-L-phenylalaninamide trifluoroacetate (195 mg) as a gummy solid retaining excess TFA which was used without further purification. MS (ESI+) for $C_{40}H_{53}ClN_{10}O_9$ m/z 853.5 (M+H)$^+$; HPLC retention time=3.45 min.

To a flask containing $N^5$-amino(nitroimino)methyl-D-ornithyl-2,6-dimethyl-L-tyrosyl-$N^6$-{[(2-chlorobenzyl)oxy]carbonyl}-L-lysyl-L-phenylalaninamide trifluoroacetate (195 mg) and palladium (10 wt % on carbon powder, dry (Aldrich 520888), 0.018 g) was added methanol (5 mL) and acetic acid (0.032 ml, 0.57 mmol). The flask was subjected to 2 cycles of evacuation—hydrogen gas backfill and the mixture stirred under 1 atm of $H_2$ at 50° C. for 7 h and ambient temperature for 12 h. The mixture was cooled, filtered through Solka-Floc, and washed with additional methanol (15 mL). The combined washes were concentrated under reduced pressure and the residue lyophilized from water (20 mL) to afford 0.175 g of a gummy solid (HPLC purity of 95 area % at 210 nm). Purification of 76 mg of the solid by CombiFlash chromatography [15.5 g RediSep C-18 Aq gold silica gel cartridge, solvent gradient: 100% water (0.1% TFA) to 100% acetonitrile (0.07% TFA)] and lyophilization afforded the title compound [56 mg, adjusted yield of 67% (tris trifluoroacetate)] as a white amorphous solid. $^1$H NMR (400 MHz, $D_2O$) δ 1.05-1.28 (m, 4H), 1.43-1.69 (m, 6 H), 2.10 (s, 6 H), 2.72-3.12 (m, 8 H), 3.87 (t, J=6 Hz, 1 H), 4.16 (t, J=7 Hz, 1 H), 4.40-4.46 (m, 1 H), 4.60 (t, J=8 Hz, 1 H), 6.43 (s, 2 H), 7.13-7.20 (m, 5 H); MS (ESI+) for $C_{32}H_{49}N_9O_5$ m/z 640.5 (M+H)$^+$; HPLC retention time=2.26 min.

Route 4A

Step 1. Preparation of N²-[(benzyloxy)carbonyl]-N⁵-[{[(benzyloxy)carbonyl]amino}{[(benzyloxy)carbonyl]imino}methyl]-D-ornithyl-2,6-dimethyl-L-tyrosyl-N⁶-{[(2-chlorobenzyl)oxy]carbonyl}-L-lysyl-L-phenylalaninamide

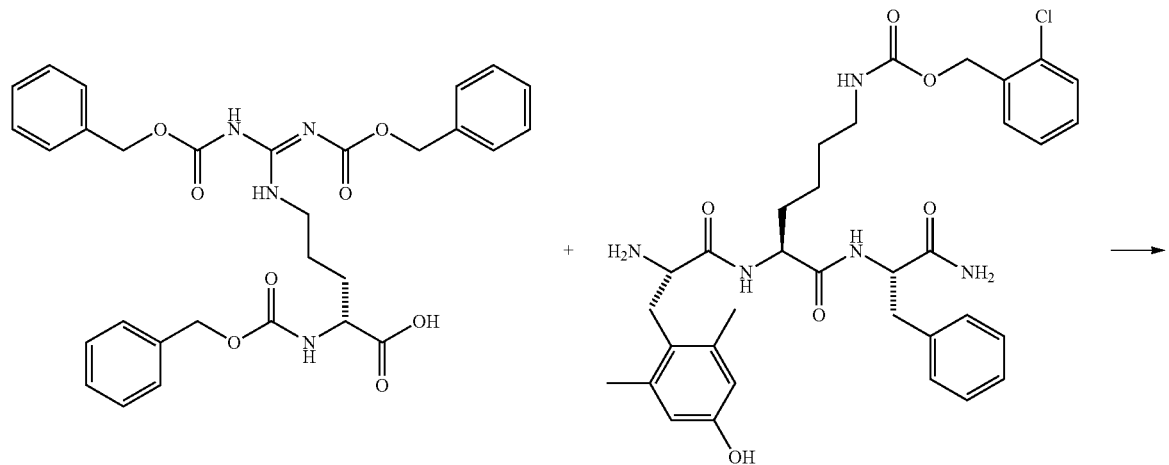

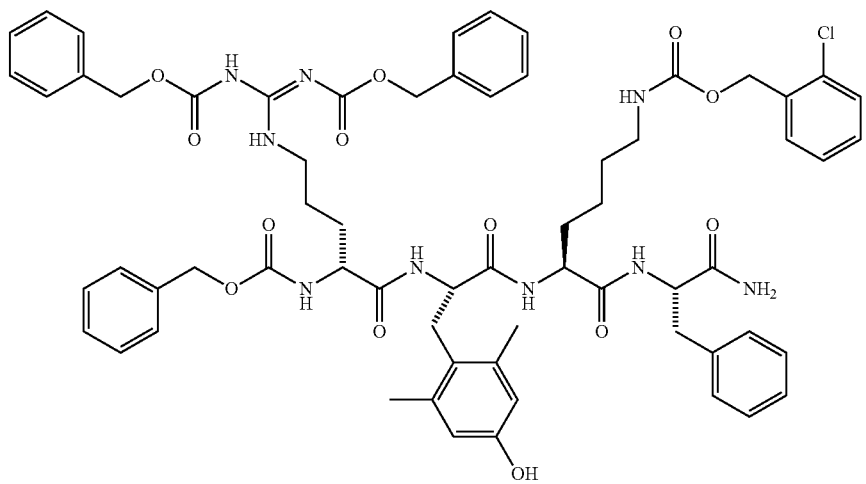

To a solution of 2,6-dimethyl-L-tyrosyl-N⁶-{[(2-chlorobenzyl)oxy]carbonyl}-L-lysyl-L-phenylalaninamide (Scheme 3A, 0.200 g, 0.31 mmol) and N²-[(benzyloxy)carbonyl]-N⁵-[{[(benzyloxy)carbonyl]amino}{[(benzyloxy)carbonyl]imino}methyl]-D-ornithine (0.194 g, 0.34 mmol) in DMF (3 mL) was added HATU (0.128 g, 0.34 mmol) and DIPEA (0.107 mL, 0.61 mmol). After 16 h, the reaction mixture was diluted with ethyl acetate (200 mL) and washed with sat aqueous NaHCO₃ (2×100 mL), brine (100 mL), aqueous 0.1 N HCl (2×100 mL), brine (100 mL), dried (anhydrous Na₂SO₄), filtered and concentrated under reduced pressure. The residue was purified by flash chromatography (1-2% methanol in DCM) to afford the title compound (0.278 g, 73%) as an amorphous white solid. $^1$H NMR (400 MHz, DMSO-$d_6$) δ 1.09-1.60 (m, 10 H), 2.12 (s, 6 H), 2.60-3.05 (m, 6 H), 3.72-3.84 (m, 2 H), 3.91-3.99 (m, 1 H), 4.11-4.17 (m, 1 H), 4.35-4.43 (m, 1 H), 4.45-4.57 (m, 1 H), 4.89-5.09 (m, 6 H), 5.20 (s, 2 H), 6.30 (s, 2 H), 7.06-7.49 (m, 28 H), 7.75 (br d, J=8 Hz, 1 H), 7.89 (br d, J=8 Hz, 1 H), 8.10 (br d, J=8 Hz, 1 H), 8.85 (s, 1 H), 9.16 (br s, 2 H); MS (ESI+) for $C_{64}H_{72}ClN_9O_{13}$ m/z 1210.7 (M+H)⁺; HPLC retention time 5.03 min.

Step 2. Preparation of D-arginyl-2,6-dimethyl-L-tyrosyl-L-lysyl-L-phenylalaninamide

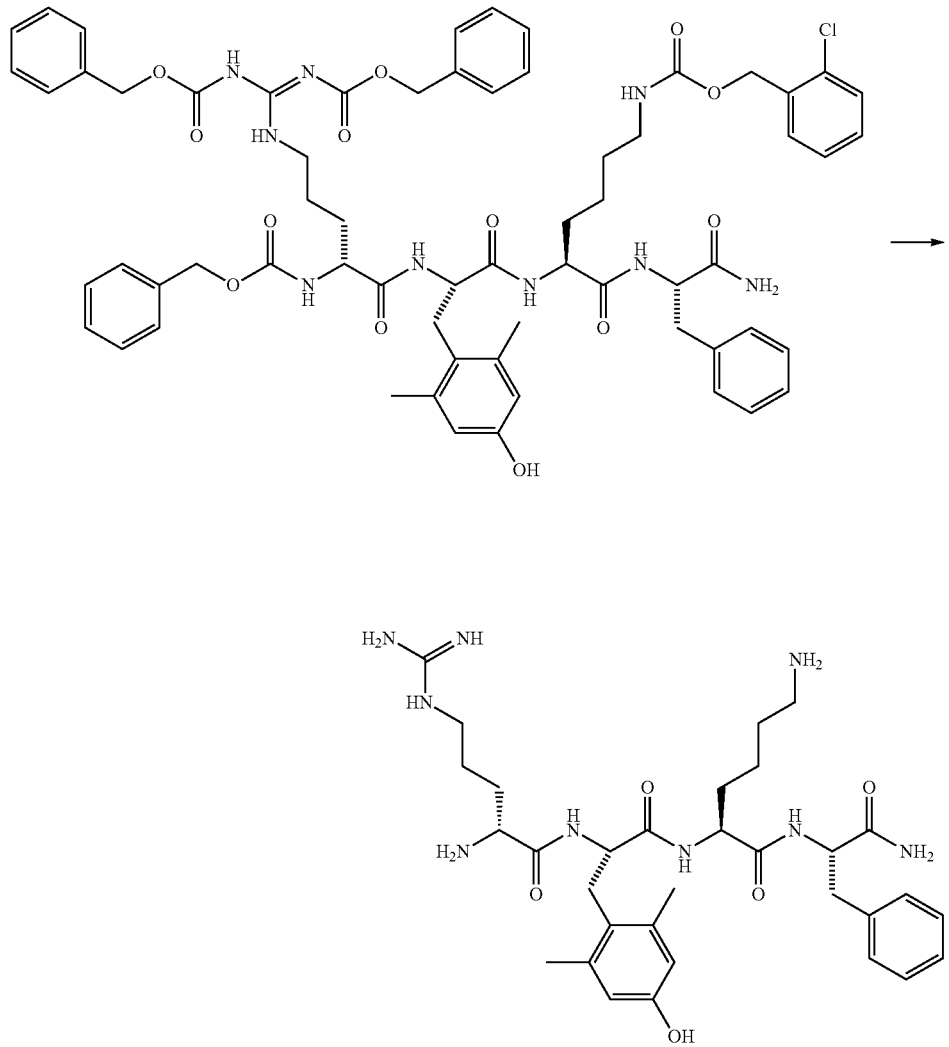

To a flask containing palladium (10 wt % on carbon powder, dry (Aldrich 520888), 0.015 g) and $N^2$-[(benzyloxy)carbonyl]-$N^5$-[{[(benzyloxy)carbonyl]amino}{[(benzyloxy)carbonyl]imino}methyl]-D-ornithyl-2,6-dimethyl-L-tyrosyl-$N^6$-{[(2-chlorobenzyl)oxy]carbonyl}-L-lysyl-L-phenylalaninamide (0.150 g, 0.124 mmol) was added methanol (5 mL) and acetic acid (0.028 ml, 0.50 mmol). The flask was subjected to 2 cycles of evacuation—hydrogen gas backfill and the mixture stirred under 1 atm of $H_2$ at 50° C. for 4 h. The mixture was cooled, filtered through Solka-Floc, and washed with additional methanol (50 mL). The combined washes were concentrated under reduced pressure and the residue lyophilized from water (20 mL) to afford the title compound (0.093 g, 99%) as a white amorphous powder. The compound was found to contain 16% w/w of acetate as determined by integration of the $^1H$ NMR spectra. $^1H$ NMR (400 MHz, $D_2O$) δ 1.05-1.30 (m, 4 H), 1.43-1.67 (m, 6 H), 1.80 (s, 6H, acetate), 2.10 (s, 6 H), 2.71-3.08 (m, 8 H), 3.82 (t, J=6 Hz, 1 H), 4.16 (t, J=7 Hz, 1 H), 4.43 (t, J=7 Hz, 1 H), 4.59 (t, J=8 Hz, 1 H), 6.43 (s, 2 H), 7.13-7.29 (m, 5 H); MS (ESI+) for $C_{32}H_{49}N_9O_5$ m/z 640.4 (M+H)$^+$; HPLC retention time=2.25 min.

Example 4

Wittig Route to Boc-DMT-OH

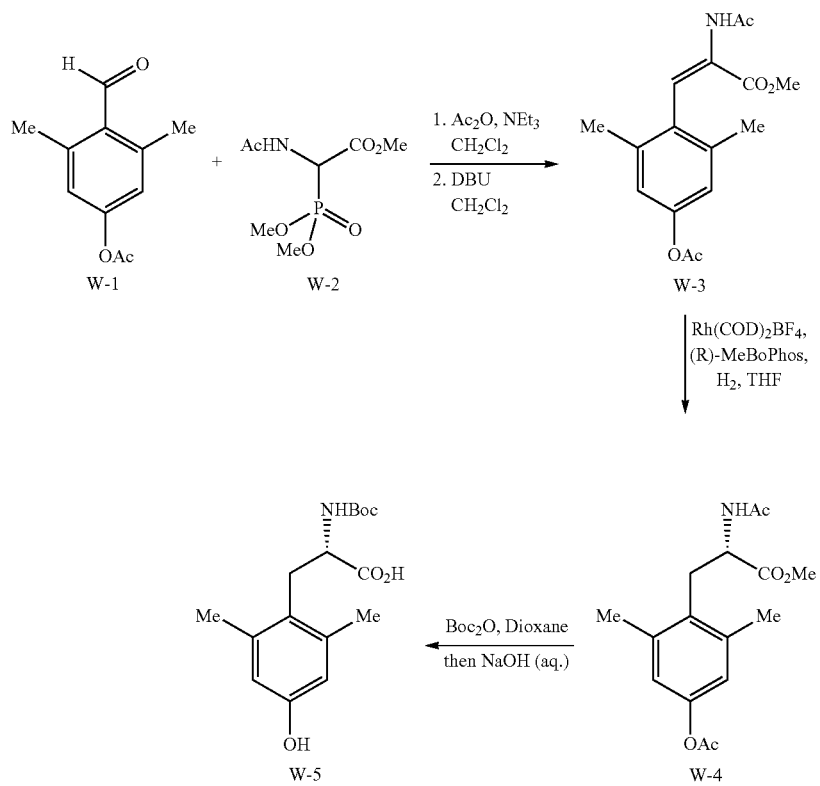

Preparation of Acetylated Wittig Reagent (W-2)

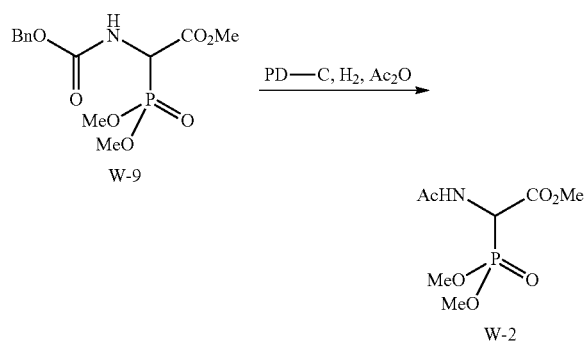

In a double glass jacketed hydrogenation autoclave 7.5 g Palladium/C 10% (dry) were treated with a soln. of 682 g N-Benzyloxycarbonyl-dimethoxyphosphorglycinate methylester (2.06 mol) in 2.1 kg THF. 252 g Acetic anhydride (2.47 nol) were added. The mixture was subjected to a H2-Atmosphere of 3 bars under vigorous stirring at a mantle temperature of 22° C., resulting to an internal temperature of 22-25° C. during hydrogenation. After 21 h the catalyst was removed by filtration (2 GF$_6$ Glass fibre filters) and washed with 280 g THF. The filtrate was concentrated under reduced pressure (50° C. Bath-temperature) by co-evaporation with three times 2.7 L DIPE to a residual volume of 1.3 L resulting in crystallization of the product. 2.5 L DIPE were added and the suspension was stirred at 50° C. for 30 min. The suspension was cooled to 23° C. The product was collected by filtration and washed twice with DIPE (0.8 L) and dried in vacuo to afford 460 g (93%) of the desired product as a colourless solid. Product purity was analyzed by thin layer chromatography (TLC) and no side products were observed. NMR and MS analysis will be performed and are expected to show peak data and ions (respectively) consistent with the indicated structures.

Preparation of N-Acetyl-α-dehydro-DMT(Ac)—OMe (W-3)

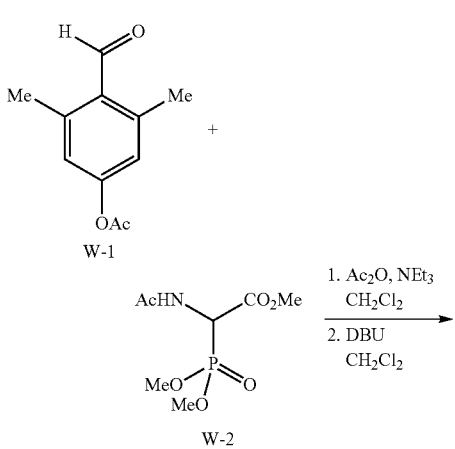

-continued

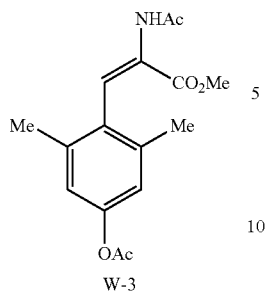

W-3

A double glass jacketed glass vessel was charged with 2,6-dimethyl-4-hydroxybenzaldehyde (262 g, 1.75 mol) and CH$_2$Cl$_2$ (1.0 kg). Triethylamine (229 g, 2.26 mol) was added followed by the slow addition of Ac$_2$O (231.0 g, 2.263 mol) at MT=10° C. in order that the internal temperature (IT) did not rise above 30° C. The resulting soln. was stirred at IT=22° C. for 1 h when HPLC showed the full conversion of the phenolic aldehyde to its acetate. DBU (996.0 g, 6.54 mol) was added to the reaction mixture followed by the slow addition of N—Ac-Gly(PO(OMe)$_2$)-OMe (W-2; 500 g) in CH$_2$Cl$_2$ (1.0 kg) over the course of 5 h. After the addition was finished stirring was continued at an IT=22° C. for an additional 18 h. AcOH (392.8 g, 6.54 mol) was added to the reaction mixture maintaining IT below 30° C. The reaction mixture was washed twice with a 5% aq. soln. of citric acid (2 Liters ("L") each) followed by four washes with water (1 L each). The organic layer was stripped from the solvent under reduced pressure down to a volume of ca. 1 l. EtOAc (1.2 L) was added and the solvent was stripped again to a volume of 1 L. EtOAc (6.2 kg) and the soln. was filtered through a pad of silica gel (500 g). The silica gel was washed with additional EtOAc (3.0 kg) and the combined EtOAc washes were evaporated under reduced pressure to a volume of ca. 2 L. Isopropyl ether (IPE; 2 L) was added at 22° C. and the resulting suspension was stirred for 1.5 h. Filtration, washing with IPE (1.5 L) and drying of the precipitate for 18 h at MT=30° C. gave the product (274.4 g, 52%) as a colourless solid. No deacetylated product was formed under these conditions and the dehydro amino acid W-3 was isolated in a purity of >98%. NMR and MS analysis will be performed and are expected to show peak data and ions (respectively) consistent with the indicated structures.

Asymmetric hydrogenation to N-Acetyl-L-DMT(Ac)—OMe (W-4)

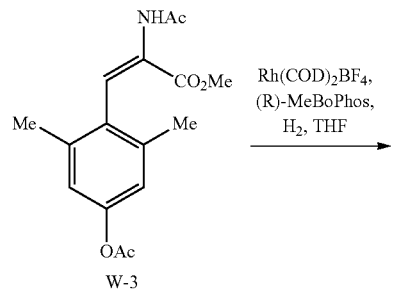

-continued

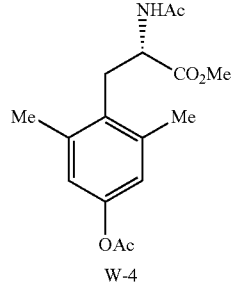

W-4

In a double glass jacketed hydrogenation autoclave N-Acetyl-a-dehydro-DMT(Ac)—OMe (250 g, 0.82 mol) was dissolved in THF (2.18 kg) under a N$_2$ atmosphere. In a separate vessel, Rh(COD)BF$_4$ and (R)-MeBoPhos in THF (0.74 kg) were stirred under a N$_2$ atmosphere for 1 h at 22° C. The resulting reddish soln. was transferred to the autoclave vessel. The reaction soln. was stirred at IT=22° C. under a 2.5 bar H$_2$ atmosphere. After 30 h when HPLC-analysis of the reaction mixture showed that less than 0.1% of the starting material was left, the atmosphere was changed to nitrogen and the reaction mixture was evaporated at reduced pressure until ca. 1 L of reaction mixture was left. EtOAc (1 L) was added and the solvent was evaporated again under reduced pressure until a volume of ca. 1 L remained in the reaction vessel. EtOAc (1.5l) was added again and the soln. as filtered through a pad of neutral Alox (820 g). The Alox was washed with additional EtOAc (1.3 L) and the combined EtOAc soln. was evaporated under reduced pressure until a volume of 1 L reaction mixture was left. IPE (3.3 L) was added at IT=22° C. The resulting suspension was stirred for 2 h, filtered and the precipitate was washed with IPE (1.6 L). The precipitate was dried under reduced pressure at MT=30° C. for 18 h to give the product as colourless solid (212.1 g, 84% uncorrected). The product was crystallized from EtOAc/IPE and was isolated in a yield of about 84% and an HPLC purity of >99.0%. NMR and MS analysis will be performed and are expected to show peak data and ions (respectively) consistent with the indicated structures.

Bocylation to Afford Boc-DMT-OH (W-5)

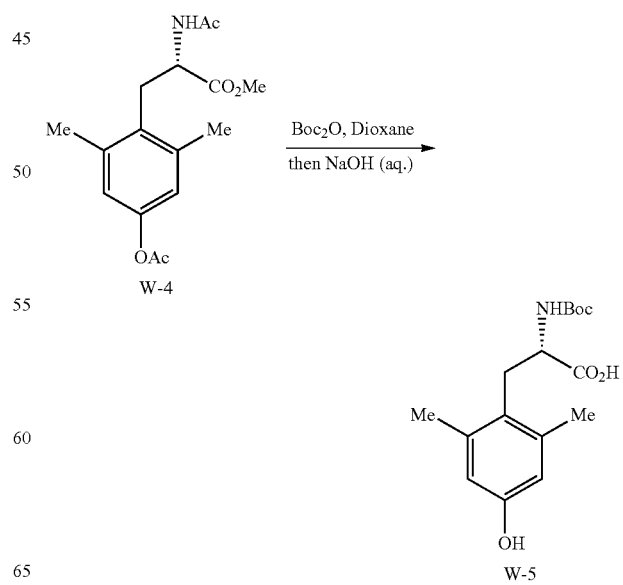

A double glass jacketed glass vessel was charged with N—Ac-L-DMT(Ac)—OMe (W-4; 158.08 g, 0.514 mol) followed by DMAP (11.94 g, 97.7 mmol) and THF (925 g). The resulting soln. was cooled to IT=5° C. A soln. of Boc$_2$O (287.4 g, 1.32 mol) in THF (337 g) was added at such a rate that IT=10° C. was not exceeded. The resulting soln. was stirred at 22° C. for 16 h. A 5M aq. NaOH soln. (660 ml) was added slowly at such a rate that IT stayed below 22° C. The biphasic emulsion was stirred for an additional 7 h. Then the product-containing aqueous layer was separated and treated with a 6N aq. HCl soln. (0.5 L). EtOAc (0.7 L) was added, followed by a 20% aq. NaHSO$_4$ soln. (1.3 L), so that the resulting pH of the aqueous soln. was 2-3. After extraction, the organic layer was separated from the aqueous layer and washed four times with H$_2$O (0.4 L). The organic layer was concentrated under reduced pressure to a volume of ca. 0.35l. Hexane (0.7 L) was added and the resulting suspension was stirred for 1.5 h at 22°. Filtration, washing of the precipitate with IPE (3×0.1 L) and drying of the product under reduced pressure at MT=30° C. for 18 h gave the product as an off-white solid (117.04 g, 74%). NMR and MS analysis will be performed and are expected to show peak data and ions (respectively) consistent with the indicated structures.

All patents, patent applications, provisional applications, and publications referred to or cited herein are incorporated by reference in their entirety, including all figures and tables, to the extent they are not inconsistent with the explicit teachings of this specification.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Other embodiments are set forth within the following claims:

What is claimed is:

1. A process comprising combining a compound of formula VIII

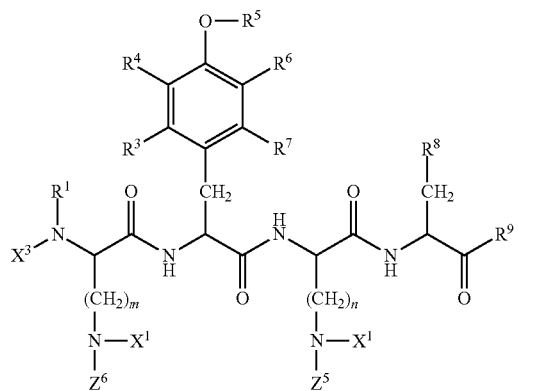

with a hydrogen source and a transition metal catalyst to form a compound of formula I

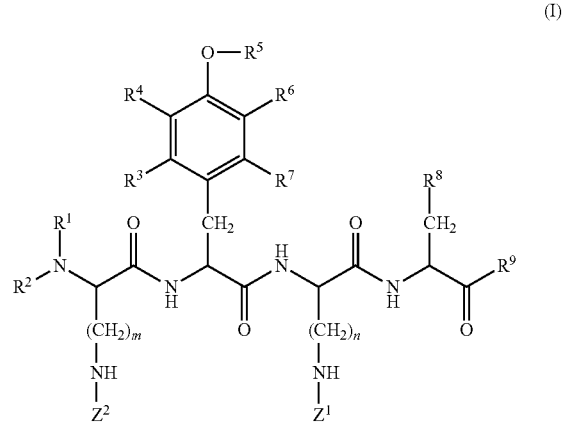

or a pharmaceutically acceptable salt thereof, wherein
$R^1$ and $R^2$ are each independently hydrogen
$R^3$ and $R^7$ are each independently methyl;
$R^4$ and $R^6$ are each independently hydrogen;
$R^5$ is hydrogen R⁸ is

[structure: phenyl ring with R¹⁰, R¹¹, R¹², R¹³, R¹⁴ substituents]

where R¹⁰, R¹¹, R¹², R¹³, and R¹⁴ are each independently hydrogen;
R⁹ is NH₂;
n is 4;
m is 3;
X¹ is H on the residue with Z⁶ and is 2-chlorobenzyloxycarbonyl on the residue with Z⁵;
X³ is benzyloxycarbonyl;
Z¹ is hydrogen;
Z² is —C(NH)—NH₂;
Z⁵ is hydrogen; and
Z⁶ is —C(N—X⁴)—NH—X² wherein X² and X⁴ are each independently benzyloxycarbonly.

2. The process of claim 1, wherein the compound of formula VIII is formed by a process comprising combining a compound of formula VI (VI)
[structure]

with a compound of formula VII (VII)
[structure]

under conditions to form the compound of formula VIII.

3. The process according to claim 2, wherein forming a compound of formula VI comprises
combining a compound of formula III (III)
[structure]

with a compound of formula IV (IV)
[structure]

under conditions to form a compound of formula V, (V)
[structure]

and
combining the compound of formula V (V)
[structure]

with a cleaving acid to produce a compound of formula VI

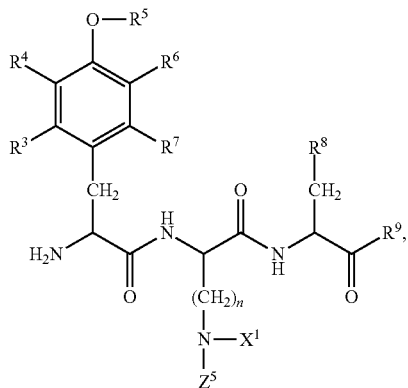

wherein
Y$^1$ is tert-butoxycarbonyl.

4. The process of claim 1, wherein
the hydrogen source comprises hydrogen gas, formic acid, formate salts, diimide, cyclohexene, cyclohexadiene, or combinations of any two or more thereof; and
the transition metal catalyst comprises Co, Ir, Mo, Ni, Pt, Pd, Rh, Ru, W, or combinations of any two or more thereof.

5. The process of claim 4, wherein the transition metal catalyst further comprises a support material, optionally wherein the support material comprises carbon, carbonate salts, silica, silicon, silicates, alumina, clay, or mixtures of any two or more thereof.

6. The process of claim 5, wherein the transition metal catalyst comprises Pd on carbon or Pd on silicon.

7. The process of claim 4, further comprising a solvent, optionally wherein the solvent comprises methanol (CH$_3$OH), ethanol (EtOH), isopropanol (iPrOH), trifluorethanol (TFE), butanol (BuOH), methylene chloride (CH$_2$Cl$_2$), chloroform (CHCl$_3$), benzotrifluoride (BTF; PhCF$_3$), tetrahydrofuran (THF), 2-methyltetrahydrofuran (2Me-THF), dimethoxyethane (DME), dioxane, ethyl acetate, isopropyl acetate, acetone, methylethyl ketone, methyl isobutyl ketone, dimethylformamide (DMF), dimethylacetamide (DMA), acetonitrile (CH$_3$CN), proprionitrile (CH$_3$CH$_2$CN), benzonitrile (PhCN), dimethyl sulfoxide, sulfolane, water, or mixtures of any two or more thereof.

8. The process of claim 2, wherein the conditions to form the compound of formula VIII comprise a coupling agent, where the coupling agent comprises (7-azabenzotriazol -1-yloxy)tripyrrolidinophosphonium hexafluorophosphate (PyAOP), O-benzotriazol-1-yl -N,N,N',N'-bis(pentamethylene)uronium hexafluorophosphate, O-(benzotriazol-1-yl) -N,N,N',N'-bis(tetramethylene)uronium hexafluorophosphate, (benzotriazol-1-yloxy)dipiperidinocarbenium hexafluorophosphate, (benzotriazol-1-yloxy)tripyrrolidinophosphonium hexafluorophosphate (PyBOP), (benzotriazol-1-yloxy)tris(dimethylamino)phosphonium hexafluorophosphate (BOP), O-(benzotriazol-1-yl)-N,N,N',N'-tetramethyluronium tetrafluoroborate (TBTU), bromotripyrrolidinophosphonium hexafluorophosphate, Bromotris(dimethylamino)phosphonium hexafluorophosphate, O-(6-chlorobenzotriazol -1-yl)-N,N,N',N'-tetramethyluronium tetrafluoroborate (TCTU), O-(6-chlorobenzotriazol -1-yl)-N,N,N',N'-tetramethyluronium hexafluorophosphate (HCTU), 2-chloro-1,3-dimethylimidazolidinium hexafluorophosphate, 2-chloro-1,3-dimethylimidazolidinium tetrafluoroborate, 2-chloro-1,3-dimethylimidazolidinium chloride, chlorodipyrrolidinocarbenium hexafluorophosphate, chloro-N,N,N',N'-tetramethylformamidinium hexafluorophosphate, chlorotripyrrolidinophosphonium hexafluorophosphate, (1-cyano-2-ethoxy-2-oxoethylidenaminooxy)dimethylamino -morpholino-carbenium hexafluorophosphate (COMU), dipyrrolidino(N-succinimidyloxy)carbenium hexafluorophosphate, O -[(ethoxycarbonyl)cyanomethylenamino]-N,N,N',N'-tetramethyluronium hexafluorophosphate, fluoro-N,N,N',N'-bis(tetramethylene) formamidinium hexafluorophosphate, fluoro-N,N,N',N'-bis(tetramethylene)formamidinium hexafluorophosphate, 1-hydroxybenzotriazole (HOBT), 1-hydroxy-7-azabenzotriazole (HOAT), 1-[bis(dimethylamino)methylene]-1H-1,2,3-triazolo[4,5-b]pyridinium 3-oxid hexafluorophosphate (HATU), N,N,N',N'-tetramethyl-O-(1H-benzotriazol-1-yl) uranium hexafluorophosphate (HBTU), 1-[(dimethylamino) (morpholino)methylene]-1H -[1,2,3]triazolo[4,5-b]pyridine-1-ium 3-oxide hexafluorophosphate (HDMA), O-(5-norbornene-2,3-dicarboximido)-N,N,N',N'-tetramethyluronium tetrafluoroborate, S-(1-oxido-2-pyridyl)-N,N,N',N'-tetramethylthiuronium hexafluorophosphate, O-(2-oxo -1(2H)pyridyl)-N,N,N',N'-tetramethyluronium tetrafluoroborate, N,N,N',N'-tetramethyl -O—(N-succinimidyl)uronium hexafluorophosphate, N,N'-dicyclohexylcarbodiimide (DCC), N,N'-diisopropylcarbodiimide, 1-ethyl-3-(3-dimethylaminopropyl)carbodiimide (EDC), 1-[3-(dimethylamino)propyl]-3-ethylcarbodiimide methiodide (EDC-MeI), propane phosphonic acid anhydride (T3P), N,N'-di-tert-butylcarbodiimide, N-cyclohexyl -N'-(2-morpholinoethyl)carbodiimide methyl-p-toluenesulfonate, 2-ethoxy-1-ethoxycarbonyl-1,2-dihydroquinoline, 1,1'-carbonyldiimidazole, 1,1'-carbonyldi(1,2,4-triazole), bis(4-nitrophenyl) carbonate, 4-nitrophenyl chloroformate, di(N-succinimidyl) carbonate, 1-(2-mesitylenesulfonyl)-3-nitro-1H-1,2,4-triazole, or a combination of any two or more thereof.

9. The process of any of claims 8, wherein the conditions to form the compound of formula VIII further comprise a solvent.

10. The process of claim 9, wherein the solvent comprises methanol (CH$_3$OH), ethanol (EtOH), isopropanol (iPrOH), trifluorethanol (TFE), butanol (BuOH), methylene chloride (CH$_2$Cl$_2$), chloroform (CHCl$_3$), benzotrifluoride (BTF; PhCF$_3$), tetrahydrofuran (THF), 2-methyltetrahydrofuran (2Me-THF), dimethoxyethane (DME), dioxane, ethyl acetate, isopropyl acetate, acetone, methylethyl ketone, methyl isobutyl ketone, dimethylformamide (DMF), dimethylacetamide (DMA), acetonitrile (CH$_3$CN), propionitrile (CH$_3$CH$_2$CN), benzonitrile (PhCN), dimethyl sulfoxide, sulfolane, water, or a mixture of any two or more thereof.

11. The process of claim 3, wherein the conditions to form the compound of formula V comprise a coupling agent, where the coupling agent comprises (7-azabenzotriazol -1-yloxy)tripyrrolidinophosphonium hexafluorophosphate (PyAOP), O-benzotriazol-1-yl -N,N,N',N'-bis(pentamethylene)uronium hexafluorophosphate, O-(benzotriazol-1-yl) -N,N,N',N'-bis(tetramethylene)uronium hexafluorophosphate, (benzotriazol-1-yloxy)dipiperidinocarbenium hexafluorophosphate, (benzotriazol-1-yloxy)tripyrrolidinophosphonium hexafluorophosphate (PyBOP), (benzotriazol-1-yloxy)tris(dimethylamino)phosphonium hexafluorophosphate (BOP), O-(benzotriazol-1-yl)-N,N,N',N'-tetramethyluronium tetrafluoroborate (TBTU), bromotripyrrolidinophosphonium hexafluorophosphate, Bromotris(dimethylamino)phosphonium hexafluorophosphate, O-(6-chlorobenzotriazol-1-yl)-N,N,N',N'-tetramethyluronium tetrafluoroborate (TCTU), O-(6-chlorobenzotriazol-1-yl)-N,N,N',N'-tetramethyluronium hexafluorophosphate (HCTU), 2-chloro-1,3-dimethylimidazolidinium hexafluorophosphate, 2-chloro-1,3-dimethylimidazolidinium tetrafluoroborate, 2-chloro-1,3-dimethylimidazolidinium chloride, chlorodipyrrolidinocarbenium hexafluorophosphate, chloro-N,N,N',N'-tetramethylformamidinium hexafluorophosphate, chlorotripyrrolidinophosphonium hexafluorophosphate, (1-cyano-2-ethoxy-2-oxoethylidenaminooxy)dimethylamino-morpholino-carbenium hexafluorophosphate (COMU), dipyrrolidino(N-succinimidyloxy)carbenium hexafluorophosphate, O-[(ethoxycarbonyl)cyanomethylenamino]-N,N,N',N'-tetramethyluronium hexafluorophosphate, fluoro-N,N,N',N'-bis(tetramethylene)formamidinium hexafluorophosphate, fluoro-N,N,N',N'-bis(tetramethylene)formamidinium hexafluorophosphate, 1-hydroxybenzotriazole (HOBT), 1-hydroxy-7-azabenzotriazole (HOAT), 1-[bis(dimethylamino)methylene]-1H-1,2,3-triazolo[4,5-b]pyridinium 3-oxid hexafluorophosphate (HATU), N,N,N',N'-tetramethyl-O-(1H-benzotriazol-1-yl)uronium hexafluorophosphate (HBTU), 1-[(dimethylamino)(morpholino)methylene]-1H-[1,2,3]triazolo[4,5-b]pyridine-1-ium 3-oxide hexafluorophosphate (HDMA), O-(5-norbornene-2,3-dicarboximido)-N,N,N',N'-tetramethyluronium tetrafluoroborate, S-(1-oxido-2-pyridyl)-N,N,N',N'-tetramethylthiuronium hexafluorophosphate, 0-(2-oxo-1(2H)pyridyl)-N,N,N',N'-tetramethyluronium tetrafluoroborate, N,N,N',N'-tetramethyl-O—(N-succinimidyl)uronium hexafluorophosphate, N,N'-dicyclohexylcarbodiimide (DCC), N,N'-diisopropylcarbodiimide, 1-ethyl-3-(3-dimethylaminopropyl)carbodiimide (EDC), 1-[3-(dimethylamino)propyl]-3-ethylcarbodiimide methiodide (EDC-MeI), propane phosphonic acid anhydride (T3P), N,N'-di-tert-butylcarbodiimide, N-cyclohexyl-N'-(2-morpholinoethyl)carbodiimide methyl-p-toluenesulfonate, 2-ethoxy-1-ethoxycarbonyl-1,2-dihydroquinoline, 1,1'-carbonyldiimidazole, 1,1'-carbonyldi(1,2,4-triazole), bis(4-nitrophenyl) carbonate, 4-nitrophenyl chloroformate, di(N-succinimidyl) carbonate, 1-(2-mesitylenesulfonyl)-3-nitro-1H-1,2,4-triazole, or combinations of any two or more thereof.

12. The process of claim 11, wherein the conditions to form the compound of formula VIII further comprise a solvent, optionally wherein the solvent comprises methanol ($CH_3OH$), ethanol (EtOH), isopropanol (iPrOH), trifluoroethanol (TFE), butanol (BuOH), methylene chloride ($CH_2Cl_2$), chloroform ($CHCl_3$), benzotrifluoride (BTF; $PhCF_3$), tetrahydrofuran (THF), 2-methyltetrahydrofuran (2Me-THF), dimethoxyethane (DME), dioxane, ethyl acetate, isopropyl acetate, acetone, methylethyl ketone, methyl isobutyl ketone, dimethylformamide (DMF), dimethylacetamide (DMA), acetonitrile ($CH_3CN$), proprionitrile ($CH_3CH_2CN$), benzonitrile (PhCN), dimethyl sulfoxide, sulfolane, water, or a mixture of any two or more thereof.

13. The process of claim 3, wherein the cleaving acid used to produce a compound of formula VI comprises a halogen acid, a carboxylic acid, a phosphonic acid, a phosphoric acid, a sulfinic acid, a sulfonic acid, a sulfuric acid, a sulfamic acid, a boric acid, a boronic acid, an acid resin, or combinations of any two or more thereof.

14. The process of claim 3, wherein the cleaving acid used to produce a compound of formula VI comprises hydrofluoric acid, hydrochloric acid (HCl), hydrobromic acid, hydroiodic acid, acetic acid (AcOH), fluoroacetic acid, trifluoroacetic acid (TFA), chloroacetic acid, benzoic acid, phosphoric acid, methanesulfonic acid, benzenesulfonic acid, p-toluene sulfonic acid, trifluoromethanesulfonic acid, sulfuric acid, or combinations of any two or more thereof.

15. The process of claim 3, wherein combining with the cleaving acid occurs at a temperature from about −40° C. to about 150° C.

16. The process of claim 3, wherein combining with the cleaving acid further comprises a protic solvent, a polar aprotic solvent, or a mixture of the two.

17. The process of claim 3, wherein combining with the cleaving acid further comprises methanol ($CH_3OH$), ethanol (EtOH), isopropanol (iPrOH), trifluorethanol (TFE), butanol (BuOH), methylene chloride ($CH_2Cl_2$), chloroform ($CHCl_3$), benzotrifluoride (BTF; $PhCF_3$), tetrahydrofuran (THF), 2-methyltetrahydrofuran (2Me-THF), dimethoxyethane (DME), dioxane, ethyl acetate, isopropyl acetate, acetone, methylethyl ketone, methyl isobutyl ketone, dimethylformamide (DMF), dimethylacetamide (DMA), acetonitrile ($CH_3CN$), proprionitrile ($CH_3CH_2CN$), benzonitrile (PhCN), dimethyl sulfoxide, sulfolane, water, or mixtures of any two or more thereof.

* * * * *